(12) United States Patent
Docherty et al.

(10) Patent No.: US 12,023,346 B1
(45) Date of Patent: *Jul. 2, 2024

(54) COMPOSITIONS AND METHODS FOR TREATING EPILEPSY

(71) Applicant: POVIVA CORP, Carson City, NV (US)

(72) Inventors: John Docherty, Port Perry (CA); Christopher Andrew Bunka, Kelowna (CA)

(73) Assignee: POVIVA CORP, Carson City, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/225,244

(22) Filed: Jul. 24, 2023

(51) Int. Cl.
| | | |
|---|---|---|
| *A61K 31/00* | (2006.01) | |
| *A61K 47/28* | (2006.01) | |
| *A61K 47/36* | (2006.01) | |
| *A61K 47/44* | (2017.01) | |
| *A61P 25/08* | (2006.01) | |

(52) U.S. Cl.
CPC ............ *A61K 31/658* (2023.05); *A61K 47/28* (2013.01); *A61K 47/36* (2013.01); *A61K 47/44* (2013.01); *A61P 25/08* (2018.01)

(58) Field of Classification Search
CPC ...... A61K 31/658; A61K 47/28; A61K 47/36; A61K 47/44; A61P 25/08
See application file for complete search history.

(56) References Cited

U.S. PATENT DOCUMENTS

| | | | |
|---|---|---|---|
| 9,949,937 B2 * | 4/2018 | Guy | .................. A61K 31/5517 |
| 9,956,183 B2 | 5/2018 | Guy et al. | |
| 9,956,184 B2 | 5/2018 | Guy et al. | |
| 9,956,185 B2 | 5/2018 | Guy et al. | |
| 9,956,186 B2 | 5/2018 | Guy et al. | |
| 10,092,525 B2 | 10/2018 | Guy et al. | |
| 10,111,840 B2 | 10/2018 | Guy et al. | |
| 10,137,095 B2 | 11/2018 | Guy et al. | |
| 10,603,288 B2 | 3/2020 | Guy et al. | |
| 10,709,671 B2 | 7/2020 | Guy et al. | |
| 10,709,673 B2 | 7/2020 | Guy | |
| 10,709,674 B2 | 7/2020 | Guy et al. | |
| 10,849,860 B2 | 12/2020 | Guy et al. | |
| 10,918,608 B2 | 2/2021 | Guy et al. | |
| 10,966,939 B2 | 4/2021 | Guy et al. | |
| 11,065,209 B2 | 7/2021 | Guy et al. | |
| 11,096,905 B2 | 8/2021 | Guy et al. | |
| 11,154,516 B2 | 10/2021 | Guy et al. | |
| 11,207,292 B2 | 12/2021 | Guy et al. | |
| 11,311,498 B2 | 4/2022 | Guy et al. | |
| 11,357,741 B2 | 6/2022 | Guy et al. | |
| 11,400,055 B2 | 8/2022 | Guy et al. | |
| 11,446,258 B2 | 9/2022 | Guy et al. | |
| 11,633,369 B2 | 4/2023 | Guy et al. | |
| 2018/0289665 A1 | 10/2018 | Turner et al. | |
| 2020/0046007 A1 | 2/2020 | Denniston | |
| 2021/0330683 A1* | 10/2021 | Docherty | ............. A61K 31/496 |

FOREIGN PATENT DOCUMENTS

| | | |
|---|---|---|
| GB | 2532281 A | 4/2016 |
| WO | 2020236802 A1 | 11/2020 |

OTHER PUBLICATIONS

Shimadzu, Online publication. First Edition: Feb. 2018, accessed Oct. 28, 2023 via https://www.shimadzu.eu/sites/shimadzu.seg/files/018_cbd_hemp_oil_b.pdf (Year: 2018).*
Pharm Sci Asia, 2018; 45 (4), 195-204 (Year: 2018).*
Arzimanoglou, Epleptic Disord 2020; 22 (1): 1-14 (Year: 2020).*
Devinsky O. et al., "Cannabidiol: Pharmacology and potential therapeutic role in epilepsy and other neuropsychiatric disorders," Epilepsia. Jun. 2014; 55(6):791-802.
Devinsky O. et al., "Randomized, dose-ranging safety trial of cannabidiol in Dravet syndrome<" Neurology 2018; vol. 90, No. 4 Apr. 3, 2018; e1204-e1211.
Devinsky O. et al., "Trial of Cannabidiol for Drug-Resistant Seizures in the Dravet Syndrome," N Engl J Med 2017, 376:2011-2020; May 25, 2017.
Patel K et al. Erlotinib-Valpoic Acid Liquisolid Formulation: Evaluating Oral Bioavailability and Cytotoxicity in Erlotinib-Resistant Non-small Cell Lung Cancer Cells AAPS Pharm Sci Tech (2019)20: 135.
Samanta D "Cannabidiol" A Review of Clinical Efficacy and Safety in Epilepsy, Pediatric Neurology 96 (2019) 24-29.
Scalia S et al. "Supercritical Fluid Extraction of Bile Acids from Bovine Bile Raw Materials," Chromatographia vol. 48 No. 11/12, Dec. 1998.

* cited by examiner

*Primary Examiner* — Susanna Moore
*Assistant Examiner* — Luisalberto Gonzalez
(74) *Attorney, Agent, or Firm* — FisherBroyles LLP; Anthony J DoVale

(57) ABSTRACT

Disclosed herein are compositions and methods for delivering compositions to a subject in need of treatment for epilepsy. The disclosed compositions are orally delivered. Further disclosed are kits comprising the disclosed compositions as part of a method of delivering cannabidiol and CBD-containing compositions to subjects in need of treatment for epilepsy.

13 Claims, 3 Drawing Sheets

1

COMPOSITIONS AND METHODS FOR TREATING EPILEPSY

FIELD

Disclosed herein are compositions and methods for delivering compositions to a subject in need of treatment for epilepsy. The disclosed compositions are orally delivered. Further disclosed are kits comprising the disclosed compositions as part of a method of delivering cannabidiol and CBD-containing compositions to subjects in need of treatment for epilepsy.

BRIEF DESCRIPTION OF THE FIGURES

FIG. 2 indicates that the plasma alanine transaminase concentration remained effectively unchanged over time.

FIG. 4 shows the plasma total bilirubin concentrations for CBD and placebo. FIG. 4 indicates that the plasma total bilirubin concentration remained effectively unchanged over time.

FIG. 5 indicates that the plasma gamma-glutamyl transferase concentration remained effectively unchanged over time.

FIG. 6 indicates that the plasma aspartate transaminase concentration remained effectively unchanged over time.

DETAILED DESCRIPTION OF THE DISCLOSURE

Figure 1:
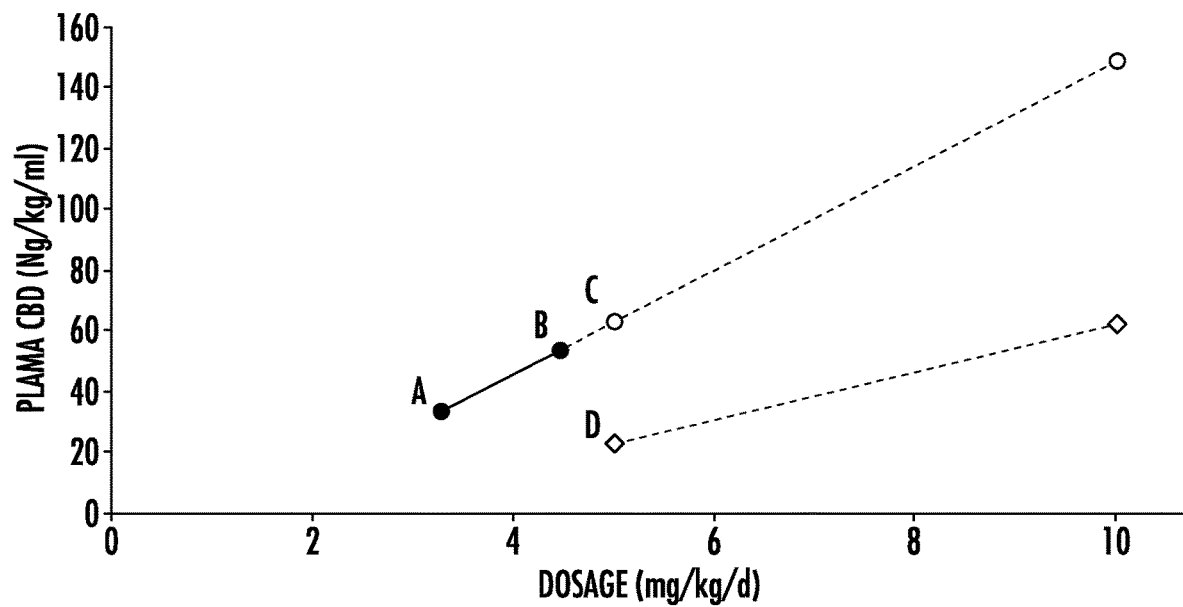
FIG. 1 compares the results of the cannabidiol steady state testing performed by Devinsky (see, Devinsky, O et al., "Randomized, dose-ranging safety trial of cannabidiol in Dravet syndrome," *Neurology* 2018, 90; e1204-e1211) versus the disclosed steady state testing of a disclosed composition in humans at two times. The black line connects the two steady state points obtained in the present test. The black dotted line extrapolates the results of the present data to the Devinsky point at approximately 5 mg/kg/day showing achievement of a pre-dose, steady state cannabidiol blood plasma level greater than 60 ng/mL vs about 22 ng/mL achieved by Devinsky.

The materials, compounds, compositions, articles, and methods described herein may be understood more readily by reference to the following detailed description of specific aspects of the disclosed subject matter and the Examples included therein.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

All percentages, ratios and proportions herein are by weight, unless otherwise specified. All temperatures are in degrees Celsius (°C) unless otherwise specified.

The terms "a" and "an" are defined as one or more unless this disclosure explicitly requires otherwise.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, an apparatus that "comprises," "has," "includes" or "contains" one or more elements possesses those one or more elements, but is not limited to possessing only those elements. Likewise, a method that "comprises," "has," "includes" or "contains" one or more steps possesses those one or more steps, but is not limited to possessing only those one or more steps.

Any embodiment of any of the disclosed methods or compositions can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

As used herein, the term "subject" refers to a human or an animal that would benefit from being administered with the disclosed compositions described in the present application, such as those suffering from, without limitation one or more forms of epilepsy.

As used herein, the terms "treat," "treating," "treatment," and the like refer to reducing or ameliorating a disorder and/or symptoms associated therewith. It will be appreciated that, although not precluded, treating epilepsy does not require that the epilepsy, condition or symptoms associated epilepsy be completely eliminated.

As used herein, the terms "prevent," "preventing," "prevention," "prophylactic treatment" and the like are encompassed within the term "treating," and refer to reducing the probability of developing a disorder or condition in a subject, who does not have, but is at risk of or susceptible to developing a disorder or condition.

As used herein, "pharmaceutically acceptable" means physiologically tolerable, for either human or veterinary applications. In addition, "pharmaceutically acceptable" is meant a material that is not biologically or otherwise undesirable, i.e., the material may be administered to a subject without causing any undesirable biological effects or interacting in a deleterious manner with any of the other components of the pharmaceutical composition in which it is contained. Essentially, the pharmaceutically acceptable material is nontoxic to the recipient. The carrier would naturally be selected to minimize any degradation of the active ingredient and to minimize any adverse side effects in the subject, as would be well known to one of skill in the art. For a discussion of pharmaceutically acceptable carriers and other components of pharmaceutical compositions, see, e.g., Remington's Pharmaceutical Sciences, 18th ed., Mack Publishing Company, 1990.

The term "pharmaceutical composition" is defined herein as a composition which is approved by a regulatory body, for example, the Food and Drug Administration (FDA), European Medicines Agency (EMA), Japanese Pharmaceutical and Food Safety Bureau (PFSB), and the like.

The term "over-the-counter" or "OTC" or "non-pharmaceutical" is defined herein as disclosed compositions that can be bought and sold without a prescription.

The feature or features of one embodiment may be applied to other embodiments, even though not described or illustrated, unless expressly prohibited by this disclosure or the nature of the embodiments.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the described invention, the preferred methods and materials are now described. All publications mentioned herein are incorporated herein by reference to disclose and describe the methods and/or materials in connection with which the publications are cited.

Cannabidiol

Cannabidiol (CBD) is a non-psychoactive component of *Cannabis sativa*. It is one of the main components that make up extracts of cannabis plants. Although CBD oil is a term of commerce, the amount of cannabidiol present in the CBD oils varies depending upon the method of extraction.

In general, CBD oil (the extract of *Cannabis sativa*) is defined in part by the following which are currently recognized guidelines for the contents and quality of CBD oil:

Full-spectrum CBD products generally contain the full range of terpenes and cannabinoids present in the source plant (including any trace amounts of THC), which boosts the so called entourage effect when consumed. This is the crudest form of CBD oil.

Broad-spectrum CBD products generally contain some other cannabinoids beyond CBD and all or most of the terpenes present in the source plant, but most or all of the THC has been stripped away. Typically the amount of THC is less than about 0.5%, however, any extracted cannabidiol in the form of CBD and/or hemp oil contains less than about 0.15% by weight of THC. This form is typically used in over-the-counter applications and is frequently known as CBD "tincture." This tincture is typically marketed with an eye dropper for application under the tongue.

Isolate is pure CBD with virtually all other compounds removed. Isolate CBD products have their own unique benefits, but they do not offer the same entourage effect that full- or broad-spectrum CBD products can. This is nearly chemically pure cannabidiol (generally at least about 98%-99% cannabidiol) in the form of a powder rather than liquid oil, which is suitable for many applications including "proof of concept" testing in a pre-pharmaceutical setting as well as in pharmaceutical preparations when manufactured according to pharmaceutical standards. For the purposes of the present disclosure cannabidiol refers to the isolate having greater than about 98% by weight of 2-[(1R,6R)-6-Isopropenyl-3-methylcyclohex-2-en-1-yl]-5-pentylbenzene-1,3-diol. In addition, the cannabidiol used to formulate the disclosed pharmaceutical compositions comprise less than about 0.15% of Δ9-tetrahydrocannabinol (THC).

The terms "Full-spectrum CBD" is defined as above. The term "CBD" or "CBD oil" is the "Broad-spectrum CBD" as defined above. Those skilled in the art of formulating cannabidiol recognize that pharmaceutical compositions require cannabidiol be present in the pure form. Therefore, CBD, CBD oil, etc. would only be suitable for non-prescription or over-the-counter formulations.

According to the present disclosure the base compositions can comprise CBD oil. What is meant herein by the term "CBD oil" is the cannabidiol-containing extract from the hemp plant *Cannabis sativa*. The CBD oil useful for preparing the disclosed compositions can be extracts which are crude extracts containing less than about 80% by weight of cannabidiol. As used herein CBD oil comprising less than about 80% by weight of cannabidiol is referred to a "crude CBD oil." When using lower percentage extracts the formulator will necessarily adjust the amount of CBD oil present in the disclosed compositions to ensure adequate delivery of the desired amount of cannabidiol.

In one embodiment, the compositions comprise a "hemp distillate" comprising from about 80% to about 92% by weight of cannabidiol. In a still further embodiment isolated, pure cannabidiol can be used in the present compositions. When the hemp distillate comprising from 80% to about 92% by weight cannabidiol is used, the term "CBD oil" applies. In some descriptions of the "CBD oil" this ingredient can be referred to as a "CBD resin." All CBD oil compositions contain CBD oil having less than 0.3% by weight of tetrahydrocannabinol (THC). COMPOSITIONS The various aspects of the disclosed compositions and methods relate to compositions comprising cannabidiol. Cannabidiol has the chemical name 2-[(1R,6R)-6-Isopropenyl-3-methylcyclohex-2-en-1-yl]-5-pentylbenzene-1,3-diol. The disclosed compositions of this aspect comprise CBD oil containing from about 80% to about 92% by weight of cannabidiol. In addition, CBD oil extracts containing about 98% by weight or greater cannabidiol comprises less than about 0.15% THC.

One Aspect of the Disclosed Compositions

In one aspect the disclosed compositions comprise:
a) from about 5% to about 20% by weight of CBD oil containing from about 88% to about 91% by weight of cannabidiol;
b) from about 15% to about 40% by weight of high oleic acid sunflower oil;
c) from about 5% to about 15% by weight of one or more bile salts; and
d) from about 35% to about 75% by weight of one or more carriers.

In one embodiment the disclosed compositions comprise:
a) from about 5% to about 20% by weight of CBD oil containing from about 88% to about 91% by weight of cannabidiol;
b) from about 15% to about 40% by weight of high oleic acid sunflower oil;
c) from about 7% to about 12% by weight of one or more bile salts wherein the salts contain from about 45% to about 55% by weight of cholic acid, deoxycholic acid, taurocholate, glycocholic acid, and mixtures thereof; and
d) from about 40% to about 70% by weight of one or more carriers chosen from gum Arabic, tapioca starch, tapioca flour, silicon dioxide, mannitol, colloidal silicon dioxide, microcrystalline cellulose, and mixture thereof.

In one iteration of this embodiment the disclosed compounds comprise:
a) from about 10% to about 30% by weight of CBD oil containing from about 88% to about 91% by weight of cannabidiol;
b) from about 20% to about 30% by weight of high oleic acid sunflower oil;
c) from about 7% to about 12% by weight of one or more bile salts wherein the salts contain from about 45% to about 55% by weight of cholic acid, deoxycholic acid, taurocholate, glycocholic acid, and mixtures thereof; and
d) from about 40% to about 70% by weight of tapioca starch, colloidal silicon dioxide, microcrystalline cellulose, and mixture thereof.

In a further embodiment the disclosed compositions, comprise:
a) from about 10% to about 20% by weight of CBD oil containing from about 88% to about 91% by weight of cannabidiol;
b) from about 22% to about 28% by weight of high oleic acid sunflower oil;
c) from about 8% to about 11% by weight of one or more bile salts wherein the salts contain from about 45% to about 55% by weight of cholic acid, deoxycholic acid, taurocholate, glycocholic acid, and mixtures thereof; and
d) from about 45% to about 55% by weight of one or more carriers chosen from gum Arabic, tapioca starch, tapioca flour, silicon dioxide, mannitol, colloidal silicon dioxide, and mixture thereof.

In one iteration of this embodiment the disclosed compositions, comprise:
a) from about 10% to about 20% by weight of CBD oil containing from about 88% to about 91% by weight of cannabidiol;
b) from about 22% to about 28% by weight of high oleic acid sunflower oil;
c) from about 8% to about 11% by weight of one or more bile salts wherein the salts contain from about 45% to about 55% by weight of cholic acid, deoxycholic acid, taurocholate, glycocholic acid, and mixtures thereof; and
d) from about 45% to about 55% by weight of tapioca starch, colloidal silicon dioxide, and mixture thereof.

In one non-limiting example of this iteration includes the disclosed compositions, comprising:
a) about 13.4% by weight of CBD oil containing from about 88% to about 91% by weight of cannabidiol;
b) about 26.8% by weight of high oleic acid sunflower oil;
c) about 10% by weight of one or more bile salts; and
d) about 25.4% % by weight of tapioca starch and 24.4% by weight of colloidal silicon dioxide.

The disclosed compositions can comprise from about 5% to about 20% by weight of CBD oil containing from about 88% to about 91% by weight of cannabidiol. In one embodiment, the composition can comprise from about 10% to about 30% by weight of cannabidiol. In another embodiment, the composition can comprise from about 10% to about 20% by weight of cannabidiol. For example, the amount of cannabidiol can be, for example 5%, 6%, 7%, 8%, 9%, 10%, 11%, 12%, 13%, 14%, 15%, 16%, 17%, 18%, 19%, or 20% of CBD oil containing from about 88% to about 91% by weight of cannabidiol.

This aspect of the disclosed compositions comprises from about 15% to about 40% by weight of high oleic acid sunflower oil. In one embodiment the compositions comprise from about 20% to about 30% by weight of high oleic acid sunflower oil. In another embodiment the compositions comprise from about 22% to about 28% by weight of high oleic acid sunflower oil.

The disclosed compositions can comprise from about 15% to about 40% by weight of high oleic acid sunflower oil, for example, 15%, 16%, 17%, 18%, 19%, 20%, 21%, 22%, 23%, 24%, 25% 26%, 27%, 28%, 29%, 30%, 31%, 32%, 33%, 34%, 35%, 36%, 37%, 38%, 39%, or 40%, by weight of high oleic acid sunflower oil.

In one aspect the disclosed compositions for use in treating epilepsy, comprise:
a) from about 30 mg to about 135 mg of CBD oil containing from about 88% to about 91% by weight of cannabidiol;
b) from about 60 mg to about 270 mg by weight of high oleic acid sunflower oil;
c) from about 25 mg to about 100 mg by weight of one or more bile salts wherein the salts contain from about 45% to about 55% by weight of cholic acid, deoxycholic acid, taurocholate, glycocholic acid, and mixtures thereof; and
d) from 120 mg to about 500 mg by weight of one or more carriers.

In one iteration of this aspect the disclosed compositions for use in treating epilepsy, comprise:
a) from about 30 mg to about 87 mg of CBD oil containing from about 88% to about 91% by weight of cannabidiol;
b) from about 60 mg to about 174 mg by weight of high oleic acid sunflower oil;
c) from about 25 mg to about 65 mg by weight of one or more bile salts wherein the salts contain from about 45% to about 55% by weight of cholic acid, deoxycholic acid, taurocholate, glycocholic acid, and mixtures thereof; and
d) from about 120 mg to about 324 mg by weight of one or more carriers.

In one aspect the disclosed compositions for use in treating epilepsy, comprise:
a) from about 30 mg to about 87 mg of CBD oil containing from about 88% to about 91% by weight of cannabidiol;
b) from about 60 mg to about 174 mg by weight of high oleic acid sunflower oil;
c) from about 25 mg to about 65 mg by weight of one or more bile salts wherein the salts contain from about 45% to about 55% by weight of cholic acid, deoxycholic acid, taurocholate, glycocholic acid, and mixtures thereof, and
d) from about 120 mg to about 324 mg by weight of tapioca starch, colloidal silicon dioxide, and mixture thereof.

In one iteration of this aspect the disclosed compositions for use in treating epilepsy, comprise:
a) from about 67 mg to about 87 mg of CBD oil containing from about 88% to about 91% by weight of cannabidiol;
b) from about 134 mg to about 174 mg by weight of high oleic acid sunflower oil;
c) from about 50 mg to about 65 mg by weight of one or more bile salts wherein the salts contain from about 45% to about 55% by weight of cholic acid, deoxycholic acid, taurocholate, glycocholic acid, and mixtures thereof, and
d) from about 250 mg to about 324 mg by weight of one or more carriers.

In one aspect the disclosed compositions for use in treating epilepsy, comprise:
a) from about 67 mg to about 87 mg of CBD oil containing from about 88% to about 91% by weight of cannabidiol;
b)
b) from about 134 mg to about 174 mg by weight of high oleic acid sunflower oil;
c) from about 50 mg to about 65 mg by weight of one or more bile salts wherein the salts contain from about 45% to about 55% by weight of cholic acid, deoxycholic acid, taurocholate, glycocholic acid, and mixtures thereof; and
d) from about 250 mg to about 324 mg by weight of tapioca starch, colloidal silicon dioxide, and mixture thereof.

In one embodiment of this aspect the disclosed compositions for use in treating epilepsy, comprise:
a) from about 30 mg to about 135 mg of CBD oil containing from about 88% to about 91% by weight of cannabidiol;
b) from about 60 mg to about 270 mg by weight of high oleic acid sunflower oil;
c) from about 25 mg to about 100 mg by weight of one or more bile salts wherein the salts contain from about 45% to about 55% by weight of cholic acid, deoxycholic acid, taurocholate, glycocholic acid, and mixtures thereof; and
d) from about 120 mg to about 500 mg by weight of one or more carriers.

In one iteration of this embodiment the disclosed compositions for use in treating epilepsy, comprise:
a) from about 30 mg to about 135 mg of CBD oil containing from about 88% to about 91% by weight of cannabidiol;
b) from about 60 mg to about 270 mg by weight of high oleic acid sunflower oil;
c) from about 25 mg to about 100 mg by weight of one or more bile salts wherein the salts contain from about 45% to about 55% by weight of cholic acid, deoxycholic acid, taurocholate, glycocholic acid, and mixtures thereof; and
d) from about 120 mg to about 500 mg by weight of tapioca starch, colloidal silicon dioxide, and mixture thereof.

In one embodiment of this aspect the disclosed compositions for use in treating epilepsy, comprise:
a) from about 67 mg to about 135 mg of CBD oil containing from about 88% to about 91% by weight of cannabidiol;
b) from about 134 mg to about 270 mg by weight of high oleic acid sunflower oil;
c) from about 50 mg to about 100 mg by weight of one or more bile salts wherein the salts contain from about 45% to about 55% by weight of cholic acid, deoxycholic acid, taurocholate, glycocholic acid, and mixtures thereof; and
d) from about 250 mg to about 500 mg by weight of one or more carriers In one iteration of this embodiment the disclosed compositions for use in treating epilepsy, comprise:
a) from about 67 mg to about 135 mg of CBD oil containing from about 88% to about 91% by weight of cannabidiol;
b) from about 134 mg to about 270 mg by weight of high oleic acid sunflower oil;
c) from about 50 mg to about 100 mg by weight of one or more bile salts wherein the salts contain from about 45% to about 55% by weight of cholic acid, deoxycholic acid, taurocholate, glycocholic acid, and mixtures thereof; and
d) from about 250 mg to about 500 mg by weight of tapioca starch, colloidal silicon dioxide, and mixture thereof.

In one embodiment of this aspect the disclosed compositions for use in treating epilepsy, comprise:
a) from about 87 mg to about 135 mg of CBD oil containing from about 88% to about 91% by weight of cannabidiol;
b) from about 174 mg to about 270 mg by weight of high oleic acid sunflower oil;
c) from about 65 mg to about 100 mg by weight of one or more bile salts wherein the salts contain from about 45% to about 55% by weight of cholic acid, deoxycholic acid, taurocholate, glycocholic acid, and mixtures thereof; and
d) from about 324 mg to about 500 mg by weight of one or more carriers In one iteration of this embodiment the disclosed compositions for use in treating epilepsy, comprise:
a) from about 87 mg to about 135 mg of CBD oil containing from about 88% to about 91% by weight of cannabidiol;
b) from about 174 mg to about 270 mg by weight of high oleic acid sunflower oil;
c) from about 65 mg to about 100 mg by weight of one or more bile salts wherein the salts contain from about 45% to about 55% by weight of cholic acid, deoxycholic acid, taurocholate, glycocholic acid, and mixtures thereof; and
d) from about 324 mg to about 500 mg by weight of tapioca starch, colloidal silicon dioxide, and mixture thereof.

In one non-limiting example, the disclosed compositions comprise:
a) about 30 mg by weight of CBD oil containing from about 88% to about 91% by weight of cannabidiol;
b) about 60 mg by weight of high oleic acid high oleic acid sunflower oil;
c) about 25 mg by weight of one or more bile salts wherein the salts contain from about 45% to about 55% by weight of cholic acid, deoxycholic acid, taurocholate, glycocholic acid, and mixtures thereof; and
d) about 63.4 mg by weight of tapioca starch and 61.1 mg by weight of colloidal silicon dioxide.

In a further non-limiting example, the disclosed compositions comprise:
a) about 67 mg by weight of CBD oil containing from about 88% to about 91% by weight of cannabidiol;
b) about 134 mg by weight of high oleic acid sunflower oil;
c) about 50 mg by weight of one or more bile salts wherein the salts contain from about 45% to about 55% by weight of cholic acid, deoxycholic acid, taurocholate, glycocholic acid, and mixtures thereof; and
d) about 127 mg by weight of tapioca starch and about 122 mg by weight of colloid silicon dioxide.

In another non-limiting example, the disclosed compositions comprise:
  a) about 87 mg by weight of CBD oil containing from about 88% to about 91% by weight of cannabidiol;
  b) about 174 mg by weight of high oleic acid sunflower oil;
  c) about 65 mg by weight of one or more bile salts wherein the salts contain from about 45% to about 55% by weight of cholic acid, deoxycholic acid, taurocholate, glycocholic acid, and mixtures thereof; and
  d) about 165 mg by weight of tapioca starch and about 159 mg by weight of colloidal silicon dioxide.

In a still further non-limiting example, the disclosed compositions comprise:
  a) about 135 mg of CBD oil containing from about 88% to about 91% by weight of cannabidiol;
  b) about 270 mg by weight of high oleic acid sunflower oil;
  c) about 100 mg by weight of one or more bile salts wherein the salts contain from about 45% to about 55% by weight of cholic acid, deoxycholic acid, taurocholate, glycocholic acid, and mixtures thereof; and
  d) about 255 mg by weight of tapioca starch and about 245 mg by weight colloidal silicon dioxide.

The disclosed compositions can comprise from about 30 mg to about 135 mg of CBD oil containing from about 88% to about 91% by weight of cannabidiol. In another embodiment, the composition comprises from about 30 mg to about 87 mg by weight of CBD oil containing from about 88% to about 91% by weight of cannabidiol. In a further embodiment, the composition comprises from about 67 mg to about 135 mg by weight of CBD oil containing from about 88% to about 91% by weight of cannabidiol. In a yet further embodiment, the composition comprises from about 87 mg to about 135 mg by weight of CBD oil containing from about 88% to about 91% by weight of cannabidiol.

The composition can comprise from about 30 to about 135 mg by weight of CBD oil containing from about 88% to about 91% by weight of cannabidiol, for example, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg. 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, 99 mg, 100 mg, 101 mg, 102, mg, 103, mg, 104 mg, 105 mg, 106 mg, 107 mg, 108 mg, 109 mg, 110 mg, 111 mg, 112 mg, 113 mg, 114 mg, 115 mg, 116 mg, 117 mg, 118 mg, 119 mg, 120 mg, 121 mg, 122 mg, 123 mg, 124 mg, 125 mg, 126 mg, 127 mg, 128 mg, 129 mg, 130 mg by weight of CBD oil containing from about 88% to about 91% by weight of cannabidiol.

The disclosed compositions can comprise from about 60 mg to about 270 mg by weight of high oleic acid sunflower oil. In one embodiment, the composition comprises from about 60 mg to about 174 mg by weight of high oleic acid sunflower oil. In another embodiment, the composition comprises from about 134 mg to about 174 mg by weight of high oleic acid sunflower oil. In a further embodiment, the composition comprises from about 60 mg to about 215 mg by weight of high oleic acid sunflower oil. In a yet further embodiment, the composition comprises from about 134 mg to about 270 mg by weight of high oleic acid sunflower oil.

The disclosed compositions can comprise from about 60 mg to about 270 mg by weight of high oleic acid sunflower oil, for example, 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg. 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, 99 mg, 100 mg, 101 mg, 102, mg, 103, mg, 104 mg, 105 mg, 106 mg, 107 mg, 108 mg, 109 mg, 110 mg, 111 mg, 112 mg, 113 mg, 114 mg, 115 mg, 116 mg, 117 mg, 118 mg, 119 mg, 120 mg, 121 mg, 122 mg, 123 mg, 124 mg, 125 mg, 126 mg, 127 mg, 128 mg, 129 mg, 130 mg, 131 mg, 132 mg, 133 mg, 134 mg, 135 mg, 136 mg, 137 mg, 138 mg, 139 mg, 140 mg, 141 mg, 142 mg, 143 mg, 144 mg, 145 mg, 146 mg, 147 mg, 148 mg, 149 mg, 150 mg, 151 mg, 152 mg, 153 mg, 154 mg, 155 mg, 156 mg, 157 mg, 158 mg, 159 mg, 160 mg, 161 mg, 162 mg, 163 mg, 164 mg, 165 mg, 166 mg, 167 mg, 168 mg, 169 mg, 170 mg, 171 mg, 172 mg, 173 mg, 174 mg, 175 mg, 167 mg, 177 mg, 178 mg, 179 mg, 180 mg, 181 mg, 182 mg, 183 mg, 184 mg, 185 mg, 186 mg, 187 mg, 188 mg, 189 mg, 190 mg, 191 mg, 192 mg, 193 mg, 194 mg, 195 mg, 196 mg, 197 mg, 198 mg, 199 mg, 200 mg, 201 mg, 202 mg, 203 mg, 204 mg, 205 mg, 206 mg, 207 mg, 208 mg, 209 mg, 210 mg, 211 mg, 212 mg, 213 mg, 214 mg, 215 mg, 216 mg, 217 mg, 218 mg, 219 mg, 220 mg, 221 mg, 222 mg, 223 mg, 224 mg, 225 mg, 226 mg, 227 mg, 228 mg, 229 mg, 230 mg, 231 mg, 232 mg, 233 mg, 234 mg, 235 mg, 236 mg, 237 mg, 238 mg, 239 mg, 240 mg, 241 mg, 242 mg, 243 mg, 244 mg, 245 mg, 246 mg, 247 mg, 248 mg, 249 mg, 250 mg, 251 mg, 252 mg, 253 mg, 254 mg, 255 mg, 256 mg, 257 mg, 258 mg, 259 mg, 260 mg, 261 mg, 262 mg, 263 mg, 264 mg, 265 mg, 266 mg, 267 mg, 268 mg, 269 mg, or 270 mg, by weight of high oleic acid sunflower oil.

According to this aspect the ratio of CBD oil containing from about 88% to about 92% by weight of cannabidiol to high oleic acid sunflower oil is from about 1:1 to about 1:3. For example, the ratio of CBD oil containing from about 88% to about 92% by weight of cannabidiol to high oleic acid sunflower oil can be 1:1, 1:1.1, 1:1.2, 1:1.3, 1:1.4, 1:1.5, 1:1.6, 1:1.7, 1:1.8, 1:1.9, 1:2, 1:2.1, 1:2.2, 1:2.3, 1:2.4, 1:2.5, 1:2.6, 1:2.7, 1:2.8, 1:2.9, or 1:3.

The disclosed compositions of this aspect are free flowing solids comprising no water or moisture. In general, the compositions are dried by any means necessary before being formed into capsules, pellets, pills, and the like. Depending upon the end use, the formulator may reconstitute the composition in an aqueous carrier. In that case the further addition of an emulsifier, which is typically added by the user, may be necessary.

In one embodiment the one or more carriers are not organic or inorganic acids that can lead to decarboxylation of the sodium bicarbonate, especially if reconstituted by the formulator as an aqueous solution.

In this aspect the disclosed compositions are free flowing solids comprising no water or moisture. In general, the compositions are dried by any means necessary before being formed into capsules, pellets, pills, and the like. Depending upon the end use, the formulator may reconstitute the composition in an aqueous carrier. In that case the further addition of an emulsifier, added by the user may be necessary.

The following Table 1 provides non-limiting examples of this aspect of the disclosed compositions.

TABLE 1

| Ingredients (mg) | 1 | 2 | 3 | 4 | 5 |
|---|---|---|---|---|---|
| CBD oil[1] | 33.5 | 67 | 87.1 | 107.2 | 134 |
| High oleic acid sunflower oil | 67 | 134 | 174.2 | 214.4 | 268 |
| Bile salts | 25 | 50 | 65 | 80 | 100 |
| Tapioca starch | 63.4 | 126.8 | 164.84 | 202.9 | 253.6 |
| Aeroperl ™ 300 | 61.1 | 122.2 | 158.86 | 195.5 | 244.4 |
| Total | 250 | 500 | 650 | 800 | 1000 |

[1]CBD Oil contains from about 88% to about 91% by weight of cannabidiol.

Another Aspect of the Disclosed Compositions

Another aspect of the present disclosure relates to compositions comprising:
  a) from about 5% to about 25% by weight of CBD oil containing from about 88% to about 91% by weight of cannabidiol;
  b) from about 5% to about 60% by weight of one or more edible oils;
  c) from about 0.1% to about 1% by weight of bile salts containing from about 45% to about 55% by weight of cholic acid, deoxycholic acid, taurocholate; glycocholic acid, and mixtures thereof;
  d) from about 10% to about 20% by weight of sodium bicarbonate; and
  e) the balance a carrier.

In one embodiment of this aspect the compositions, comprise:
  a) from about 5% to about 25% by weight of CBD oil containing from about 88% to about 91% by weight of cannabidiol;
  b) from about 5% to about 60% by weight of one or more edible oils;
  c) from about 0.1% to about 1% by weight of bile salts containing from about 45% to about 55% by weight of cholic acid, deoxycholic acid, taurocholate; glycocholic acid, and mixtures thereof;
  d) from about 10% to about 20% by weight of sodium bicarbonate; and
  e) from about 30% to about 85% by weight of gum Arabic.

In one iteration of this embodiment the compositions comprise:
  a) from about 5% to about 25% by weight of CBD oil containing from about 88% to about 91% by weight of cannabidiol;
  b) from about 5% to about 60% by weight of high oleic acid sunflower oil;
  c) from about 0.1% to about 1% by weight of bile salts containing from about 45% to about 55% by weight of cholic acid, deoxycholic acid, taurocholate; glycocholic acid, and mixtures thereof;
  d) from about 10% to about 20% by weight of sodium bicarbonate; and
  e) from about 30% to about 85% by weight gum Arabic.

In another iteration of this embodiment the compositions comprise:
  a) from about 5% to about 25% by weight of CBD oil containing from about 88% to about 91% by weight of cannabidiol;
  b) from about 5% to about 60% by weight of high oleic acid coconut oil;
  c) from about 0.1% to about 1% by weight of bile salts containing from about 45% to about 55% by weight of cholic acid, deoxycholic acid, taurocholate; glycocholic acid, and mixtures thereof;
  d) from about 10% to about 20% by weight of sodium bicarbonate; and
  e) from about 30% to about 85% by weight gum Arabic.

In a further iteration of this embodiment the compositions comprise:
  a) from about 5% to about 25% by weight of CBD oil containing from about 88% to about 91% by weight of cannabidiol;
  b) from about 5% to about 60% by weight of high oleic acid sesame oil;
  c) from about 0.1% to about 1% by weight of bile salts containing from about 45% to about 55% by weight of cholic acid, deoxycholic acid, taurocholate; glycocholic acid, and mixtures thereof;
  d) from about 10% to about 20% by weight of sodium bicarbonate; and
  e) from about 30% to about 85% by weight gum Arabic.

In another embodiment of this aspect the compositions, comprise:
  a) from about 10% to about 20% by weight of CBD oil containing from about 88% to about 91% by weight of cannabidiol;
  b) from about 10% to about 40% by weight of one or more edible oils;
  c) from about 0.5% to about 1% by weight of bile salts containing from about 45% to about 55% by weight of cholic acid, deoxycholic acid, taurocholate; glycocholic acid, and mixtures thereof;
  d) from about 10% to about 20% by weight of sodium bicarbonate; and
  e) from about 30% to about 85% by weight of gum Arabic.

In one iteration of this embodiment the compositions comprise:
  a) from about 10% to about 20% by weight of CBD oil containing from about 88% to about 91% by weight of cannabidiol;
  b) from about 10% to about 40% by weight of high oleic acid sunflower oil;
  c) from about 0.5% to about 1% by weight of bile salts containing from about 45% to about 55% by weight of cholic acid, deoxycholic acid, taurocholate; glycocholic acid, and mixtures thereof;
  d) from about 10% to about 20% by weight of sodium bicarbonate; and
  e) from about 40% to about 70% by weight of gum Arabic.

In one iteration of this embodiment the compositions comprise:
  a) from about 10% to about 20% by weight of CBD oil containing from about 88% to about 91% by weight of cannabidiol;
  b) from about 10% to about 40% by weight of coconut oil;
  c) from about 0.5% to about 1% by weight of bile salts containing from about 45% to about 55% by weight of cholic acid, deoxycholic acid, taurocholate; glycocholic acid, and mixtures thereof;
  d) from about 10% to about 20% by weight of sodium bicarbonate; and
  e) from about 40% to about 70% by weight of gum Arabic In one iteration of this embodiment the compositions comprise:
a) from about 10% to about 20% by weight of CBD oil containing from about 88% to about 91% by weight of cannabidiol;
b) from about 10% to about 40% by weight of sesame oil;
c) from about 0.5% to about 1% by weight of bile salts containing from about 45% to about 55% by weight of cholic acid, deoxycholic acid, taurocholate; glycocholic acid, and mixtures thereof;
d) from about 10% to about 20% by weight of sodium bicarbonate; and
e) from about 40% to about 70% by weight of gum Arabic In one embodiment of this aspect the compositions, comprise:
a) from about 15% to about 20% by weight of CBD oil containing from about 88% to about 91% by weight of cannabidiol;
b) from about 15% to about 40% by weight of one or more edible oils;
c) from about 0.5% to about 1% by weight of bile salts containing from about 45% to about 55% by weight of cholic acid, deoxycholic acid, taurocholate; glycocholic acid, and mixtures thereof;
d) from about 12% to about 17% by weight of sodium bicarbonate; and
e) from about 40% to about 80% by weight of gum Arabic.

In one iteration of this embodiment the compositions comprise:
a) from about 15% to about 20% by weight of CBD oil containing from about 88% to about 91% by weight of cannabidiol;
b) from about 15% to about 40% by weight of high oleic acid sunflower oil;
c) from about 0.5% to about 1% by weight of bile salts containing from about 45% to about 55% by weight of cholic acid, deoxycholic acid, taurocholate; glycocholic acid, and mixtures thereof;
d) from about 12% to about 17% by weight of sodium bicarbonate; and
e) from about 40% to about 70% by weight of gum Arabic.

In one iteration of this embodiment the compositions comprise:
a) from about 15% to about 20% by weight of CBD oil containing from about 88% to about 91% by weight of cannabidiol;
b) from about 15% to about 40% by weight of coconut oil;
c) from about 0.5% to about 1% by weight of bile salts containing from about 45% to about 55% by weight of cholic acid, deoxycholic acid, taurocholate; glycocholic acid, and mixtures thereof;
d) from about 12% to about 17% by weight of sodium bicarbonate; and
e) from about 40% to about 70% by weight of gum Arabic.

In one iteration of this embodiment the compositions comprise:
a) from about 15% to about 20% by weight of CBD oil containing from about 88% to about 91% by weight of cannabidiol;
b) from about 15% to about 40% by weight of sesame oil;
c) from about 0.5% to about 1% by weight of bile salts containing from about 45% to about 55% by weight of cholic acid, deoxycholic acid, taurocholate; glycocholic acid, and mixtures thereof;
d) from about 12% to about 17% by weight of sodium bicarbonate; and
e) from about 40% to about 70% by weight of gum Arabic.

In another embodiment of this aspect the compositions, comprise:
a) from about 10% to about 20% by weight of CBD oil containing from about 88% to about 91% by weight of cannabidiol;
b) from about 10% to about 40% by weight of one or more edible oils;
c) from about 0.5% to about 1% by weight of bile salts containing from about 45% to about 55% by weight of cholic acid, deoxycholic acid, taurocholate; glycocholic acid, and mixtures thereof;
d) from about 10% to about 20% by weight of sodium bicarbonate; and
e) from about 30% to about 75% by weight gum Arabic.

In one iteration of this embodiment the compositions comprise:
a) from about 10% to about 20% by weight of CBD oil containing from about 88% to about 91% by weight of cannabidiol;
b) from about 10% to about 40% by weight of high oleic acid sunflower oil;
c) from about 0.5% to about 1% by weight of bile salts containing from about 45% to about 55% by weight of cholic acid, deoxycholic acid, taurocholate; glycocholic acid, and mixtures thereof;
d) from about 10% to about 20% by weight of sodium bicarbonate; and
e) from about 40% to about 70% by weight of gum Arabic.

In a further iteration of this embodiment the compositions comprise:
a) from about 10% to about 20% by weight of CBD oil containing from about 88% to about 91% by weight of cannabidiol;
b) from about 10% to about 40% by weight of coconut oil;
c) from about 0.5% to about 1% by weight of bile salts containing from about 45% to about 55% by weight of cholic acid, deoxycholic acid, taurocholate; glycocholic acid, and mixtures thereof;
d) from about 10% to about 20% by weight of sodium bicarbonate; and
e) from about 40% to about 70% by weight of gum Arabic.

In another iteration of this embodiment the compositions comprise:
a) from about 10% to about 20% by weight of CBD oil containing from about 88% to about 91% by weight of cannabidiol;
b) from about 10% to about 40% by weight of sesame oil;
c) from about 0.5% to about 1% by weight of bile salts containing from about 45% to about 55% by weight of cholic acid, deoxycholic acid, taurocholate; glycocholic acid, and mixtures thereof;
d) from about 10% to about 20% by weight of sodium bicarbonate; and
e) from about 40% to about 70% by weight of gum Arabic.

In one embodiment of this aspect the compositions, comprise:
a) from about 15% to about 20% by weight of CBD oil containing from about 88% to about 91% by weight of cannabidiol;

b) from about 15% to about 40% by weight of high oleic acid sunflower oil;
c) from about 0.5% to about 1% by weight of bile salts containing from about 45% to about 55% by weight of cholic acid, deoxycholic acid, taurocholate; glycocholic acid, and mixtures thereof;
d) from about 12% to about 17% by weight of sodium bicarbonate; and
e) from about 40% to about 80% by weight of gum Arabic.

In one iteration of this embodiment the compositions comprise:
a) from about 15% to about 20% by weight of CBD oil containing from about 88% to about 91% by weight of cannabidiol;
b) from about 15% to about 40% by weight of high oleic acid sunflower oil;
c) from about 0.5% to about 1% by weight of bile salts containing from about 45% to about 55% by weight of cholic acid, deoxycholic acid, taurocholate; glycocholic acid, and mixtures thereof;
d) from about 12% to about 17% by weight of sodium bicarbonate; and
e) from about 40% to about 80% by weight of gum Arabic.

In one iteration of this embodiment the compositions comprise:
a) from about 15% to about 20% by weight of CBD oil containing from about 88% to about 91% by weight of cannabidiol;
b) from about 15% to about 40% by weight of coconut oil;
c) from about 0.5% to about 1% by weight of bile salts containing from about 45% to about 55% by weight of cholic acid, deoxycholic acid, taurocholate; glycocholic acid, and mixtures thereof;
d) from about 12% to about 17% by weight of sodium bicarbonate; and
e) from about 40% to about 80% by weight of gum Arabic In one iteration of this embodiment the compositions comprise:
a) from about 15% to about 20% by weight of CBD oil containing from about 88% to about 91% by weight of cannabidiol;
b) from about 15% to about 40% by weight of sesame oil;
c) from about 0.5% to about 1% by weight of bile salts containing from about 45% to about 55% by weight of cholic acid, deoxycholic acid, taurocholate; glycocholic acid, and mixtures thereof;
d) from about 12% to about 17% by weight of sodium bicarbonate; and
e) the balance from about 40% to about 80% by weight of gum Arabic In another aspect of the disclosed compositions, the compositions, comprise:
a) from about 5% to about 25% by weight of CBD oil containing from about 88% to about 91% by weight of cannabidiol;
b) from about 5% to about 60% by weight of one or more edible oils;
c) from about 0.1% to about 1% by weight of bile salts containing from about 45% to about 55% by weight of cholic acid, deoxycholic acid, taurocholate; glycocholic acid, and mixtures thereof;
d) from about 10% to about 20% by weight of sodium bicarbonate; and
e) the balance a carrier.

In one embodiment of this aspect the compositions, comprise:
a) from about 5% to about 25% by weight of CBD oil containing from about 88% to about 91% by weight of cannabidiol;
b) from about 5% to about 60% by weight of one or more edible oils chosen from sunflower oil, coconut oil, canola oil, palm oil, soybean oil, corn oil, safflower oil, and peanut oil;
c) from about 0.1% to about 1% by weight of bile salts containing from about 45% to about 55% by weight of cholic acid, deoxycholic acid, taurocholate; glycocholic acid, and mixtures thereof;
d) from about 10% to about 20% by weight of sodium bicarbonate; and
e) from about 30% to about 85% by weight of gum Arabic.

In one iteration of this embodiment the compositions comprise:
a) from about 5% to about 25% by weight of CBD oil containing from about 88% to about 91% by weight of cannabidiol;
b) from about 5% to about 60% by weight of sunflower oil;
c) from about 0.1% to about 1% by weight of bile salts containing from about 45% to about 55% by weight of cholic acid, deoxycholic acid, taurocholate; glycocholic acid, and mixtures thereof;
d) from about 10% to about 20% by weight of sodium bicarbonate; and
e) from about 30% to about 85% by weight gum Arabic.

In one iteration of this embodiment the compositions comprise:
a) from about 5% to about 25% by weight of CBD oil containing from about 88% to about 91% by weight of cannabidiol;
b) from about 5% to about 60% by weight of coconut;
c) from about 0.1% to about 1% by weight of bile salts containing from about 45% to about 55% by weight of cholic acid, deoxycholic acid, taurocholate; glycocholic acid, and mixtures thereof;
d) from about 10% to about 20% by weight of sodium bicarbonate; and
e) from about 30% to about 85% by weight gum Arabic.

In one iteration of this embodiment the compositions comprise:
a) from about 5% to about 25% by weight of CBD oil containing from about 88% to about 91% by weight of cannabidiol;
b) from about 5% to about 60% by weight of sesame oil;
c) from about 0.1% to about 1% by weight of bile salts containing from about 45% to about 55% by weight of cholic acid, deoxycholic acid, taurocholate; glycocholic acid, and mixtures thereof;
d) from about 10% to about 20% by weight of sodium bicarbonate; and
e) from about 30% to about 85% by weight gum Arabic.

In another embodiment of this aspect the compositions, comprise:
a) from about 10% to about 20% by weight of CBD oil containing from about 88% to about 91% by weight of cannabidiol;
b) from about 10% to about 40% by weight of one or more edible oils chosen from sunflower oil, coconut oil, canola oil, palm oil, soybean oil, corn oil, safflower oil, and peanut oil;

c) from about 0.5% to about 1% by weight of bile salts containing from about 45% to about 55% by weight of cholic acid, deoxycholic acid, taurocholate; glycocholic acid, and mixtures thereof;
d) from about 10% to about 20% by weight of sodium bicarbonate; and
e) from about 30% to about 85% by weight of a carrier chosen from mannitol, colloidal silicon dioxide, tapioca starch, gum Arabic, and mixtures thereof.

In one iteration of this embodiment the compositions comprise:
a) from about 10% to about 20% by weight of CBD oil containing from about 88% to about 91% by weight of cannabidiol;
b) from about 10% to about 40% by weight of sunflower oil;
c) from about 0.5% to about 1% by weight of bile salts containing from about 45% to about 55% by weight of cholic acid, deoxycholic acid, taurocholate; glycocholic acid, and mixtures thereof;
d) from about 10% to about 20% by weight of sodium bicarbonate; and
e) from about 30% to about 85% by weight of gum Arabic.

In one iteration of this embodiment the compositions comprise:
a) from about 10% to about 20% by weight of CBD oil containing from about 88% to about 91% by weight of cannabidiol;
b) from about 10% to about 40% by weight of coconut oil;
c) from about 0.5% to about 1% by weight of bile salts containing from about 45% to about 55% by weight of cholic acid, deoxycholic acid, taurocholate; glycocholic acid, and mixtures thereof;
d) from about 10% to about 20% by weight of sodium bicarbonate; and
e) from about 30% to about 85% by weight of gum Arabic.

In one iteration of this embodiment the compositions comprise:
a) from about 10% to about 20% by weight of CBD oil containing from about 88% to about 91% by weight of cannabidiol;
b) from about 10% to about 40% by weight of sesame oil;
c) from about 0.5% to about 1% by weight of bile salts containing from about 45% to about 55% by weight of cholic acid, deoxycholic acid, taurocholate; glycocholic acid, and mixtures thereof;
d) from about 10% to about 20% by weight of sodium bicarbonate; and
e) from about 30% to about 85% by weight of gum Arabic.

In a further embodiment of this aspect the compositions, comprise:
a) from about 15% to about 20% by weight of CBD oil containing from about 88% to about 91% by weight of cannabidiol;
b) from about 15% to about 40% by weight of one or more edible oils chosen from sunflower oil, coconut oil, canola oil, palm oil, soybean oil, corn oil, safflower oil, and peanut oil;
c) from about 0.5% to about 1% by weight of bile salts containing from about 45% to about 55% by weight of cholic acid, deoxycholic acid, taurocholate; glycocholic acid, and mixtures thereof;
d) from about 12% to about 17% by weight of sodium bicarbonate; and
e) from about 40% to about 80% by weight of gum Arabic.

In one iteration of this embodiment the compositions comprise:
a) from about 15% to about 20% by weight of CBD oil containing from about 88% to about 91% by weight of cannabidiol;
b) from about 15% to about 40% by weight of sunflower oil;
c) from about 0.5% to about 1% by weight of bile salts containing from about 45% to about 55% by weight of cholic acid, deoxycholic acid, taurocholate; glycocholic acid, and mixtures thereof;
d) from about 12% to about 17% by weight of sodium bicarbonate; and
e) from about 40% to about 80% by weight of a carrier chosen from mannitol (Partek-M™ Mannitol), colloidal silicon dioxide (Aeroperl™ 300), and mixtures thereof.

In one iteration of this embodiment the compositions comprise:
a) from about 15% to about 20% by weight of CBD oil containing from about 88% to about 91% by weight of cannabidiol;
b) from about 15% to about 40% by weight of coconut oil;
c) from about 0.5% to about 1% by weight of bile salts containing from about 45% to about 55% by weight of cholic acid, deoxycholic acid, taurocholate; glycocholic acid, and mixtures thereof;
d) from about 12% to about 17% by weight of sodium bicarbonate; and
e) from about 40% to about 80% by weight of gum Arabic In one iteration of this embodiment the compositions comprise:
a) from about 15% to about 20% by weight of CBD oil containing from about 88% to about 91% by weight of cannabidiol;
b) from about 15% to about 40% by weight of sesame oil;
c) from about 0.5% to about 1% by weight of bile salts containing from about 45% to about 55% by weight of cholic acid, deoxycholic acid, taurocholate; glycocholic acid, and mixtures thereof;
d) from about 12% to about 17% by weight of sodium bicarbonate; and
e) from about 40% to about 80% by weight of gum Arabic.

The disclosed compositions of this aspect comprise from about 5% to about 25% by weight of CBD oil. In one embodiment the disclosed compositions can comprise from about 10% to about 20% by weight of CBD oil. In one embodiment, the composition can comprise from about 15% to about 20% by weight of CBD oil. In another embodiment, the composition can comprise from about 10% to about 15% by weight of CBD oil. In a further embodiment, the composition can comprise from about 12% to about 17% by weight of CBD oil.

For example, the amount of CBD oil can be, for example, 5%, 6%, 7%, 8%, 9%, 10%, 11%, 12%, 13%, 14%, 15%, 16%, 17%, 18%, 19%, 20%, 21%, 22%, 23%, 24%, or 25%.

The disclosed composition of this aspect can comprise from about 5% to about 60% by weight of one or more edible oils. In one embodiment, the compositions comprise from about 10% to about 40% by weight of one or more edible oils. In one embodiment, the compositions comprise from about 15% to about 40% by weight of one or more edible oils. In one embodiment, the compositions comprise from about 20% to about 30% by weight of one or more edible oils. In one embodiment, the compositions comprise from about 25% to about 35% by weight of one or more edible oils. The disclosed composition of this aspect can comprise from about 0.5% to about 60% by weight of one or more edible oils, for example 5%, 6%, 7%, 8%, 9%, 10%, 11%, 12%, 13%, 14%, 15%, 16%, 17%, 18%, 19%, 20%, 21%, 22%, 23%, 24%, 25% 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, or 60% by weight, or any fractional amount thereof, of one or more sunflower oil.

In a yet further aspect the disclosed compositions, comprise:
- a) from about 5 mg to about 32 mg by weight of CBD oil containing from about 88% to about 91% by weight of cannabidiol;
- b) from about 10 mg to about 65 mg by weight of one or more edible oils chosen from sunflower oil, coconut oil, canola oil, palm oil, soybean oil, corn oil, safflower oil, peanut oil, and mixtures thereof;
- c) from about 75 mg to about 300 mg by weight of bile salts containing from about 45% to about 55% by weight of cholic acid, deoxycholic acid, taurocholate; glycocholic acid, and mixtures thereof;
- d) from about 35 mg to about 150 mg by weight of sodium bicarbonate; and
- e) from about 110 mg to about 465 mg of a carrier.

In one embodiment of this aspect the disclosed compositions, comprise:
- a) from about 5 mg to about 32 mg by weight of CBD oil containing from about 88% to about 91% by weight of cannabidiol;
- b) from about 10 mg to about 65 mg by weight of one or more edible oils chosen from sunflower oil, coconut oil, canola oil, palm oil, soybean oil, corn oil, safflower oil, peanut oil, and mixtures thereof;
- c) from about 75 mg to about 300 mg by weight of bile salts containing from about 45% to about 55% by weight of cholic acid, deoxycholic acid, taurocholate; glycocholic acid, and mixtures thereof;
- d) from about 35 mg to about 150 mg by weight of sodium bicarbonate; and
- e) from about 110 mg to about 465 mg of gum Arabic.

In one iteration of this embodiment the disclosed compositions, comprise:
- a) from about 5 mg to about 32 mg by weight of CBD oil containing from about 88% to about 91% by weight of cannabidiol;
- b) from about 10 mg to about 65 mg by weight high oleic acid sunflower oil;
- c) from about 75 mg to about 300 mg by weight of bile salts containing from about 45% to about 55% by weight of cholic acid, deoxycholic acid, taurocholate; glycocholic acid, and mixtures thereof;
- d) from about 35 mg to about 150 mg by weight of sodium bicarbonate; and
- e) from about 110 mg to about 465 mg of gum Arabic.

In one iteration of this embodiment the disclosed compositions, comprise:
- a) from about 5 mg to about 32 mg by weight of CBD oil containing from about 88% to about 91% by weight of cannabidiol;
- b) from about 10 mg to about 65 mg by weight of coconut oil;
- c) from about 75 mg to about 300 mg by weight of bile salts containing from about 45% to about 55% by weight of cholic acid, deoxycholic acid, taurocholate; glycocholic acid, and mixtures thereof;
- d) from about 35 mg to about 150 mg by weight of sodium bicarbonate; and
- e) from about 110 mg to about 465 mg of gum Arabic.

In one iteration of this embodiment the disclosed compositions, comprise:
- a) from about 5 mg to about 32 mg by weight of CBD oil containing from about 88% to about 91% by weight of cannabidiol;
- b) from about 10 mg to about 65 mg by weight of sesame oil;
- c) from about 75 mg to about 300 mg by weight of bile salts containing from about 45% to about 55% by weight of cholic acid, deoxycholic acid, taurocholate; glycocholic acid, and mixtures thereof;
- d) from about 35 mg to about 150 mg by weight of sodium bicarbonate; and
- e) from about 110 mg to about 465 mg of gum Arabic.

In one iteration of this embodiment the disclosed compositions, comprise:
- a) from about 10 mg to about 32 mg by weight of CBD oil containing from about 88% to about 91% by weight of cannabidiol;
- b) from about 20 mg to about 65 mg by weight of one or more edible oils chosen from sunflower oil, coconut oil, canola oil, palm oil, soybean oil, corn oil, safflower oil, peanut oil, and mixtures thereof;
- c) from about 120 mg to about 300 mg by weight of bile salts containing from about 45% to about 55% by weight of cholic acid, deoxycholic acid, taurocholate; glycocholic acid, and mixtures thereof;
- d) from about 60 mg to about 150 mg by weight of sodium bicarbonate; and
- e) from about 180 mg to about 465 mg by weight of gum Arabic.

In one iteration of this embodiment the disclosed compositions, comprise:
- a) from about 10 mg to about 32 mg by weight of CBD oil containing from about 88% to about 91% by weight of cannabidiol;
- b) from about 20 mg to about 65 mg by weight of high oleic acid sunflower oil;
- c) from about 120 mg to about 300 mg by weight of bile salts containing from about 45% to about 55% by weight of cholic acid, deoxycholic acid, taurocholate; glycocholic acid, and mixtures thereof;
- d) from about 60 mg to about 150 mg by weight of sodium bicarbonate; and
- e) from about 180 mg to about 465 mg by weight of gum Arabic.

In one iteration of this embodiment the disclosed compositions, comprise:
- a) from about 10 mg to about 32 mg by weight of CBD oil containing from about 88% to about 91% by weight of cannabidiol;
- b) from about 20 mg to about 65 mg by weight of coconut oil;
- c) from about 120 mg to about 300 mg by weight of bile salts containing from about 45% to about 55% by weight of cholic acid, deoxycholic acid, taurocholate; glycocholic acid, and mixtures thereof;
- d) from about 60 mg to about 150 mg by weight of sodium bicarbonate; and
- e) from about 180 mg to about 465 mg by weight of gum Arabic.

In one iteration of this embodiment the disclosed compositions, comprise:
- a) from about 10 mg to about 32 mg by weight of CBD oil containing from about 88% to about 91% by weight of cannabidiol;
- b) from about 20 mg to about 65 mg by weight of sesame oil;
- c) from about 120 mg to about 300 mg by weight of bile salts containing from about 45% to about 55% by weight of cholic acid, deoxycholic acid, taurocholate; glycocholic acid, and mixtures thereof;
- d) from about 60 mg to about 150 mg by weight of sodium bicarbonate; and
- e) from about 180 mg to about 465 mg by weight of gum Arabic.

In a further iteration of this embodiment the disclosed compositions, comprise:
- a) from about 16 mg to about 32 mg by weight of CBD oil containing from about 88% to about 91% by weight of cannabidiol;
- b) from about 35 mg to about 65 mg by weight of one or more edible oils chosen from sunflower oil, coconut oil, canola oil, palm oil, soybean oil, corn oil, safflower oil, peanut oil, and mixtures thereof;
- c) from about 180 mg to about 300 mg by weight of bile salts containing from about 45% to about 55% by weight of cholic acid, deoxycholic acid, taurocholate; glycocholic acid, and mixtures thereof;
- d) from about 90 mg to about 150 mg by weight of sodium bicarbonate; and
- e) from about 270 mg to about 465 mg by weight of gum Arabic.

In a further iteration of this embodiment the disclosed compositions, comprise:
- a) from about 16 mg to about 32 mg by weight of CBD oil containing from about 88% to about 91% by weight of cannabidiol;
- b) from about 35 mg to about 65 mg by weight of high oleic acid sunflower oil;
- c) from about 180 mg to about 300 mg by weight of bile salts containing from about 45% to about 55% by weight of cholic acid, deoxycholic acid, taurocholate; glycocholic acid, and mixtures thereof;
- d) from about 90 mg to about 150 mg by weight of sodium bicarbonate; and
- e) from about 270 mg to about 465 mg by weight of gum Arabic.

In a further iteration of this embodiment the disclosed compositions, comprise:
- a) from about 16 mg to about 32 mg by weight of CBD oil containing from about 88% to about 91% by weight of cannabidiol;
- b) from about 35 mg to about 65 mg by weight of coconut oil;
- c) from about 180 mg to about 300 mg by weight of bile salts containing from about 45% to about 55% by weight of cholic acid, deoxycholic acid, taurocholate; glycocholic acid, and mixtures thereof;
- d) from about 90 mg to about 150 mg by weight of sodium bicarbonate; and
- e) from about 270 mg to about 465 mg by weight of gum Arabic.

In a further iteration of this embodiment the disclosed compositions, comprise:
- a) from about 16 mg to about 32 mg by weight of CBD oil containing from about 88% to about 91% by weight of cannabidiol;
- b) from about 35 mg to about 65 mg by weight of sesame oil;
- c) from about 180 mg to about 300 mg by weight of bile salts containing from about 45% to about 55% by weight of cholic acid, deoxycholic acid, taurocholate; glycocholic acid, and mixtures thereof;
- d) from about 90 mg to about 150 mg by weight of sodium bicarbonate; and
- e) from about 270 mg to about 465 mg by weight of gum Arabic.

In a further iteration of this embodiment the disclosed compositions comprise:
- a) from about 23 mg to about 32 mg by weight of CBD oil containing from about 88% to about 91% by weight of cannabidiol;
- b) from about 46 mg to about 65 mg by weight of one or more edible oils chosen from sunflower oil, coconut oil, canola oil, palm oil, soybean oil, corn oil, safflower oil, peanut oil, and mixtures thereof;
- c) from about 240 mg to about 300 mg by weight of bile salts containing from about 45% to about 55% by weight of cholic acid, deoxycholic acid, taurocholate; glycocholic acid, and mixtures thereof;
- d) from about 120 mg to about 150 mg by weight of sodium bicarbonate; and
- e) from about 365 mg to about 465 mg by weight of gum Arabic.

In another iteration of this embodiment the disclosed compositions comprise:
- a) from about 23 mg to about 32 mg by weight of CBD oil containing from about 88% to about 91% by weight of cannabidiol;
- b) from about 46 mg to about 65 mg by weight of high oleic acid sunflower oil;
- c) from about 240 mg to about 300 mg by weight of bile salts containing from about 45% to about 55% by weight of cholic acid, deoxycholic acid, taurocholate; glycocholic acid, and mixtures thereof;
- d) from about 120 mg to about 150 mg by weight of sodium bicarbonate; and
- e) from about 365 mg to about 465 mg by weight of gum Arabic.

In a yet further iteration of this embodiment the disclosed compositions comprise:
- a) from about 23 mg to about 32 mg by weight of CBD oil containing from about 88% to about 91% by weight of cannabidiol;
- b) from about 46 mg to about 65 mg by weight of coconut oil;
- c) from about 240 mg to about 300 mg by weight of bile salts containing from about 45% to about 55% by weight of cholic acid, deoxycholic acid, taurocholate; glycocholic acid, and mixtures thereof;
- d) from about 120 mg to about 150 mg by weight of sodium bicarbonate; and
- e) from about 365 mg to about 465 mg by weight of gum Arabic.

In a still further iteration of this embodiment the disclosed compositions comprise:
- a) from about 23 mg to about 32 mg by weight of CBD oil containing from about 88% to about 91% by weight of cannabidiol;
- b) from about 46 mg to about 65 mg by weight of sesame oil;
- c) from about 240 mg to about 300 mg by weight of bile salts containing from about 45% to about 55% by weight of cholic acid, deoxycholic acid, taurocholate; glycocholic acid, and mixtures thereof;
d) from about 120 mg to about 150 mg by weight of sodium bicarbonate; and
e) from about 365 mg to about 465 mg by weight of gum Arabic.

In a yet still further iteration of this embodiment the disclosed compositions, comprise:
a) from about 10 mg to about 23 mg by weight of CBD oil containing from about 88% to about 91% by weight of cannabidiol;
b) from about 20 mg to about 46 mg by weight of one or more edible oils chosen from sunflower oil, coconut oil, canola oil, palm oil, soybean oil, corn oil, safflower oil, peanut oil, and mixtures thereof;
c) from about 120 mg to about 240 mg by weight of bile salts containing from about 45% to about 55% by weight of cholic acid, deoxycholic acid, taurocholate; glycocholic acid, and mixtures thereof;
d) from about 120 mg to about 150 mg by weight of sodium bicarbonate; and
e) from about 180 mg to about 365 mg by weight of gum Arabic.

In a yet still further iteration of this embodiment the disclosed compositions, comprise:
a) from about 10 mg to about 23 mg by weight of CBD oil containing from about 88% to about 91% by weight of cannabidiol;
b) from about 20 mg to about 46 mg by weight of high oleic acid sunflower oil;
c) from about 120 mg to about 240 mg by weight of bile salts containing from about 45% to about 55% by weight of cholic acid, deoxycholic acid, taurocholate; glycocholic acid, and mixtures thereof;
d) from about 120 mg to about 150 mg by weight of sodium bicarbonate; and
e) from about 180 mg to about 365 mg by weight of gum Arabic.

In a yet still further iteration of this embodiment the disclosed compositions, comprise:
a) from about 10 mg to about 23 mg by weight of CBD oil containing from about 88% to about 91% by weight of cannabidiol;
b) from about 20 mg to about 46 mg by weight of coconut oil;
c) from about 120 mg to about 240 mg by weight of bile salts containing from about 45% to about 55% by weight of cholic acid, deoxycholic acid, taurocholate; glycocholic acid, and mixtures thereof;
d) from about 120 mg to about 150 mg by weight of sodium bicarbonate; and
e) from about 180 mg to about 365 mg by weight of gum Arabic.

In a yet still further iteration of this embodiment the disclosed compositions, comprise:
a) from about 10 mg to about 23 mg by weight of CBD oil containing from about 88% to about 91% by weight of cannabidiol;
b) from about 20 mg to about 46 mg by weight of sesame oil;
c) from about 120 mg to about 240 mg by weight of bile salts containing from about 45% to about 55% by weight of cholic acid, deoxycholic acid, taurocholate; glycocholic acid, and mixtures thereof;
d) from about 120 mg to about 150 mg by weight of sodium bicarbonate; and
e) from about 180 mg to about 365 mg by weight of gum Arabic.

In a another still further iteration of this embodiment the disclosed compositions, comprise:
a) from about 10 mg to about 16 mg by weight of CBD oil containing from about 88% to about 91% by weight of cannabidiol;
b) from about 20 mg to about 65 mg by weight of one or more edible oils chosen from sunflower oil, coconut oil, canola oil, palm oil, soybean oil, corn oil, safflower oil, peanut oil, and mixtures thereof;
c) from about 180 mg to about 240 mg by weight of bile salts containing from about 45% to about 55% by weight of cholic acid, deoxycholic acid, taurocholate; glycocholic acid, and mixtures thereof;
d) from about 90 mg to about 150 mg by weight of sodium bicarbonate; and
e) from about 180 mg to about 270 mg by weight of gum Arabic.

In a another still further iteration of this embodiment the disclosed compositions, comprise:
a) from about 10 mg to about 16 mg by weight of CBD oil containing from about 88% to about 91% by weight of cannabidiol;
b) from about 20 mg to about 65 mg by weight of high oleic acid sunflower oil;
c) from about 180 mg to about 240 mg by weight of bile salts containing from about 45% to about 55% by weight of cholic acid, deoxycholic acid, taurocholate; glycocholic acid, and mixtures thereof;
d) from about 90 mg to about 150 mg by weight of sodium bicarbonate; and
e) from about 180 mg to about 270 mg by weight of gum Arabic.

In a another still further iteration of this embodiment the disclosed compositions, comprise:
a) from about 10 mg to about 16 mg by weight of CBD oil containing from about 88% to about 91% by weight of cannabidiol;
b) from about 20 mg to about 65 mg by weight of coconut oil;
c) from about 180 mg to about 240 mg by weight of bile salts containing from about 45% to about 55% by weight of cholic acid, deoxycholic acid, taurocholate; glycocholic acid, and mixtures thereof;
d) from about 90 mg to about 150 mg by weight of sodium bicarbonate; and
e) from about 180 mg to about 270 mg by weight of gum Arabic.

In a another still further iteration of this embodiment the disclosed compositions, comprise:
a) from about 10 mg to about 16 mg by weight of CBD oil containing from about 88% to about 91% by weight of cannabidiol;
b) from about 20 mg to about 65 mg by weight of sesame oil;
c) from about 180 mg to about 240 mg by weight of bile salts containing from about 45% to about 55% by weight of cholic acid, deoxycholic acid, taurocholate; glycocholic acid, and mixtures thereof;
d) from about 90 mg to about 150 mg by weight of sodium bicarbonate; and
e) from about 180 mg to about 270 mg by weight of gum Arabic.

In one non-limiting example of this aspect of the disclosed compositions, comprise:
- a) about 5 mg by weight of CBD oil containing from about 88% to about 91% by weight of cannabidiol;
- b) about 10 mg by weight of high oleic acid sunflower oil;
- c) about 75 mg by weight of bile salts containing from about 45% to about 55% by weight of cholic acid, deoxycholic acid, taurocholate; glycocholic acid, and mixtures thereof;
- d) about 35 mg by weight of sodium bicarbonate; and
- e) about 110 mg by weight of gum Arabic.

In one non-limiting example of this aspect of the disclosed compositions, comprise:
- a) about 5 mg by weight of CBD oil containing from about 88% to about 91% by weight of cannabidiol;
- b) about 10 mg by weight of coconut oil;
- c) about 75 mg by weight of bile salts containing from about 45% to about 55% by weight of cholic acid, deoxycholic acid, taurocholate; glycocholic acid, and mixtures thereof;
- d) about 35 mg by weight of sodium bicarbonate; and
- e) about 110 mg by weight of gum Arabic.

In one non-limiting example of this aspect of the disclosed compositions, comprise:
- a) about 5 mg by weight of CBD oil containing from about 88% to about 91% by weight of cannabidiol;
- b) about 10 mg by weight of sesame oil;
- c) about 75 mg by weight of bile salts containing from about 45% to about 55% by weight of cholic acid, deoxycholic acid, taurocholate; glycocholic acid, and mixtures thereof;
- d) about 35 mg by weight of sodium bicarbonate; and
- e) about 110 mg by weight of gum Arabic.

In another non-limiting example of this aspect of the disclosed compositions, comprise:
- a) about 10 mg by weight of CBD oil containing from about 88% to about 91% by weight of cannabidiol;
- b) about 20 mg by weight of high oleic acid sunflower oil;
- c) about 120 mg by weight of bile salts containing from about 45% to about 55% by weight of cholic acid, deoxycholic acid, taurocholate; glycocholic acid, and mixtures thereof;
- d) about 60 mg by weight of sodium bicarbonate; and
- e) about 180 mg by weight of gum Arabic.

In another non-limiting example of this aspect of the disclosed compositions, comprise:
- a) about 10 mg by weight of CBD oil containing from about 88% to about 91% by weight of cannabidiol;
- b) about 20 mg by weight of coconut oil;
- c) about 120 mg by weight of bile salts containing from about 45% to about 55% by weight of cholic acid, deoxycholic acid, taurocholate; glycocholic acid, and mixtures thereof;
- d) about 60 mg by weight of sodium bicarbonate; and
- e) about 180 mg by weight of gum Arabic.

In another non-limiting example of this aspect of the disclosed compositions, comprise:
- a) about 10 mg by weight of CBD oil containing from about 88% to about 91% by weight of cannabidiol;
- b) about 20 mg by weight of sesame oil;
- c) about 120 mg by weight of bile salts containing from about 45% to about 55% by weight of cholic acid, deoxycholic acid, taurocholate; glycocholic acid, and mixtures thereof;
- d) about 60 mg by weight of sodium bicarbonate; and
- e) about 180 mg by weight of gum Arabic.

In a yet still further non-limiting example of this disclosed compositions, comprise:
- a) about 16 mg by weight of CBD oil containing from about 88% to about 91% by weight of cannabidiol;
- b) about 35 mg by weight of high oleic acid sunflower oil;
- c) about 180 mg by weight of bile salts containing from about 45% to about 55% by weight of cholic acid, deoxycholic acid, taurocholate; glycocholic acid, and mixtures thereof;
- d) about 90 mg by weight of sodium bicarbonate; and
- e) about 270 mg by weight of gum Arabic.

In a yet still further non-limiting example of this disclosed compositions, comprise:
- a) about 16 mg by weight of CBD oil containing from about 88% to about 91% by weight of cannabidiol;
- b) about 35 mg by weight of coconut oil;
- c) about 180 mg by weight of bile salts containing from about 45% to about 55% by weight of cholic acid, deoxycholic acid, taurocholate; glycocholic acid, and mixtures thereof;
- d) about 90 mg by weight of sodium bicarbonate; and
- e) about 270 mg by weight of gum Arabic.

In a yet still further non-limiting example of this disclosed compositions, comprise:
- a) about 16 mg by weight of CBD oil containing from about 88% to about 91% by weight of cannabidiol;
- b) about 35 mg by weight of sesame oil;
- c) about 180 mg by weight of bile salts containing from about 45% to about 55% by weight of cholic acid, deoxycholic acid, taurocholate; glycocholic acid, and mixtures thereof;
- d) about 90 mg by weight of sodium bicarbonate; and
- e) about 270 mg by weight of gum Arabic.

In a yet another non-limiting example of this disclosed compositions, comprise:
- a) about 23 mg by weight of CBD oil containing from about 88% to about 91% by weight of cannabidiol;
- b) about 46 mg by weight of high oleic acid sunflower oil;
- c) about 240 mg by weight of bile salts containing from about 45% to about 55% by weight of cholic acid, deoxycholic acid, taurocholate; glycocholic acid, and mixtures thereof;
- d) about 120 mg by weight of sodium bicarbonate; and
- e) about 365 mg by weight of gum Arabic.

In a yet another non-limiting example of this disclosed compositions, comprise:
- a) about 23 mg by weight of CBD oil containing from about 88% to about 91% by weight of cannabidiol;
- b) about 46 mg by weight of coconut oil;
- c) about 240 mg by weight of bile salts containing from about 45% to about 55% by weight of cholic acid, deoxycholic acid, taurocholate; glycocholic acid, and mixtures thereof;
- d) about 120 mg by weight of sodium bicarbonate; and
- e) about 365 mg by weight of gum Arabic.

In a yet another non-limiting example of this disclosed compositions, comprise:
- a) about 23 mg by weight of CBD oil containing from about 88% to about 91% by weight of cannabidiol;
- b) about 46 mg by weight of sesame oil;
- c) about 240 mg by weight of bile salts containing from about 45% to about 55% by weight of cholic acid, deoxycholic acid, taurocholate; glycocholic acid, and mixtures thereof;
- d) about 120 mg by weight of sodium bicarbonate; and
- e) about 365 mg by weight of gum Arabic.

In a still yet further non-limiting example the compositions comprise:
- a) about 32 mg by weight of CBD oil containing from about 88% to about 91% by weight of cannabidiol;
- b) about 65 mg by weight of high oleic acid sunflower oil;
- c) about 300 mg by weight of bile salts containing from about 45% to about 55% by weight of cholic acid, deoxycholic acid, taurocholate; glycocholic acid, and mixtures thereof;
- d) about 150 mg by weight of sodium bicarbonate; and
- e) 465 mg by weight of gum Arabic.

In a still yet another non-limiting example the compositions comprise:
- a) about 32 mg by weight of CBD oil containing from about 88% to about 91% by weight of cannabidiol;
- b) about 65 mg by weight of coconut oil;
- c) about 300 mg by weight of bile salts containing from about 45% to about 55% by weight of cholic acid, deoxycholic acid, taurocholate; glycocholic acid, and mixtures thereof;
- d) about 150 mg by weight of sodium bicarbonate; and
- e) 465 mg by weight of gum Arabic.

In a another still yet further non-limiting example the compositions comprise:
- a) about 32 mg by weight of CBD oil containing from about 88% to about 91% by weight of cannabidiol;
- b) about 65 mg by weight of sesame oil;
- c) about 300 mg by weight of bile salts containing from about 45% to about 55% by weight of cholic acid, deoxycholic acid, taurocholate; glycocholic acid, and mixtures thereof;
- d) about 150 mg by weight of sodium bicarbonate; and
- e) 465 mg by weight of gum Arabic.

The disclosed compositions of this aspect comprise from about 5 mg to about 32 mg by weight of CBD oil containing from about 88% to about 91% by weight of cannabidiol. In one embodiment the compositions can comprise from about 10 mg to about 32 mg by weight of CBD oil containing from about 88% to about 91% by weight of cannabidiol. In another embodiment the compositions can comprise from about 16 mg to about 32 mg by weight of CBD oil containing from about 88% to about 91% by weight of cannabidiol. In a further embodiment the compositions can comprise from about 23 mg to about 32 mg by weight of CBD oil containing from about 88% to about 91% by weight of cannabidiol. In a still further embodiment the compositions can comprise from about 10 mg to about 23 mg by weight of CBD oil containing from about 88% to about 91% by weight of cannabidiol. In another further embodiment the compositions can comprise from about 10 mg to about 16 mg by weight of CBD oil containing from about 88% to about 91% by weight of cannabidiol.

The compositions can comprise, for example, 5 mg. 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, by weight of CBD oil containing from about 88% to about 91% by weight of cannabidiol.

The disclosed compositions of this aspect comprise from about 10 mg to about 65 mg by weight of one or more edible oils chosen from sunflower oil, coconut oil, canola oil, palm oil, soybean oil, corn oil, safflower oil, peanut oil, and mixtures thereof. In one embodiment the disclosed compositions comprise from about 5 mg to about 32 mg by weight of one or more edible oils. In another embodiment the disclosed compositions comprise from about 23 mg to about 32 mg by weight of one or more edible oils. In a further embodiment the disclosed compositions comprise from about 10 mg to about 23 mg by weight of one or more edible oils. In another embodiment the disclosed compositions comprise from about 10 mg to about 32 mg by weight of one or more edible oils. In a further embodiment the disclosed compositions comprise from about 10 mg to about 16 mg by weight of one or more edible oils. In another embodiment the disclosed compositions comprise from about 10 mg to about 32 mg by weight of one or more edible oils.

The disclosed compositions of this aspect can comprise from about 10 mg to about 650 mg by weight of one or more edible oils, for example, present disclosure comprise from about 10 mg to about 500 mg by weight of bile salts, for example, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, or 65 mg, of one or more edible oils.

Table 2A, 2B and 2C disclose non-limiting examples of the disclosed compositions according to this aspect.

TABLE 2A

| Ingredients | mg | mg | mg | mg | mg |
|---|---|---|---|---|---|
| CBD oil[1] | 7.6 | 12.2 | 18.3 | 24.4 | 30.6 |
| High oleic acid sunflower oil | 15.3 | 24.4 | 36.7 | 48.9 | 61.1 |
| Bile salts[2] | 75 | 120 | 180 | 240 | 300 |
| Sodium bicarbonate | 37.5 | 60 | 90 | 120 | 150 |
| Gum Arabic | 114.6 | 183.4 | 275 | 366.7 | 458.3 |
| Total | 250 | 400 | 600 | 800 | 1000 |

[1]CBD oil extract containing from about 88% to about 91% by weight of cannabidiol
[2]Bile salts containing from about 45% to about 55% by weight of cholic acid, deoxycholic acid, taurocholate; glycocholic acid, and mixtures thereof

TABLE 2B

| Ingredients | mg | mg | mg | mg | mg |
|---|---|---|---|---|---|
| CBD oil[1] | 7.6 | 12.2 | 18.3 | 24.4 | 30.6 |
| Coconut oil | 15.3 | 24.4 | 36.7 | 48.9 | 61.1 |
| Bile salts[2] | 75 | 120 | 180 | 240 | 300 |
| Sodium bicarbonate | 37.5 | 60 | 90 | 120 | 150 |
| Gum Arabic | 114.6 | 183.4 | 275 | 366.7 | 458.3 |
| Total | 250 | 400 | 600 | 800 | 1000 |

[1]CBD oil extract containing from about 88% to about 91% by weight of cannabidiol
[2]Bile salts containing from about 45% to about 55% by weight of cholic acid, deoxycholic acid, taurocholate; glycocholic acid, and mixtures thereof

TABLE 2C

| Ingredients | mg | mg | mg | mg | mg |
|---|---|---|---|---|---|
| CBD oil[1] | 7.6 | 12.2 | 18.3 | 24.4 | 30.6 |
| Sesame seed oil | 15.3 | 24.4 | 36.7 | 48.9 | 61.1 |
| Bile salts[2] | 75 | 120 | 180 | 240 | 300 |
| Sodium bicarbonate | 37.5 | 60 | 90 | 120 | 150 |
| Gum Arabic | 114.6 | 183.4 | 275 | 366.7 | 458.3 |
| Total | 250 | 400 | 600 | 800 | 1000 |

[1]CBD oil extract containing from about 88% to about 91% by weight of cannabidiol
[2]Bile salts containing from about 45% to about 55% by weight of cholic acid, deoxycholic acid, taurocholate; glycocholic acid, and mixtures thereof A further Aspect of the Disclosed Compositions A further aspect of the present disclosure relates to compositions comprising:
- a) from about 5% to about 25% by weight of CBD oil extract containing at least about 98% by weight of cannabidiol;
- b) from about 5% to about 60% by weight of one or more edible oils chosen from sunflower oil, coconut oil, canola oil, palm oil, soybean oil, corn oil, safflower oil, and peanut oil;
- c) from about 0.1% to about 1% by weight of deoxycholic acid;
- d) the balance a carrier.

In one embodiment of this aspect the compositions, comprise:
- a) from about 5% to about 25% by weight of CBD oil extract containing at least about 98% by weight of cannabidiol;
- b) from about 5% to about 60% by weight of high oleic acid olive oil;
- c) from about 0.1% to about 1% by weight of deoxycholic acid;
- d) from about 30% to about 85% by weight of a carrier chosen from mannitol, colloidal silicon dioxide, tapioca starch, gum Arabic, and mixtures thereof.

In one iteration of this embodiment the compositions comprise:
- a) from about 5% to about 25% by weight of CBD oil extract containing at least about 98% by weight of cannabidiol;
- b) from about 5% to about 60% by weight of high oleic acid olive oil;
- c) from about 0.1% to about 1% by weight of deoxycholic acid;
- d) from about 30% to about 85% by weight of carrier chosen from mannitol, colloidal silicon dioxide, and mixtures thereof.

In another embodiment of this aspect the compositions, comprise:
- a) from about 10% to about 20% by weight of CBD oil extract containing at least about 98% by weight of cannabidiol;
- b) from about 10% to about 40% by weight of high oleic acid olive oil;
- c) from about 0.5% to about 1% by weight of deoxycholic acid;
- d) from about 30% to about 85% by weight of a carrier chosen from mannitol, colloidal silicon dioxide, tapioca starch, gum Arabic, and mixtures thereof.

In one iteration of this embodiment the compositions comprise:
- a) from about 10% to about 20% by weight of CBD oil extract containing at least about 98% by weight of cannabidiol;
- b) from about 10% to about 40% by weight of high oleic acid olive oil;
- c) from about 0.5% to about 1% by weight of deoxycholic acid;
- d) from about 40% to about 70% by weight of carrier chosen from mannitol, colloidal silicon dioxide, and mixtures thereof.

In one embodiment of this aspect the compositions, comprise:
- a) from about 15% to about 20% by weight of CBD oil extract containing at least about 98% by weight of cannabidiol;
- b) from about 15% to about 40% by weight of high oleic acid olive oil;
- c) from about 0.5% to about 1% by weight of deoxycholic acid;
- d) from about 40% to about 80% by weight of a carrier chosen from mannitol, colloidal silicon dioxide, tapioca starch, gum Arabic, and mixtures thereof.

In one iteration of this embodiment the compositions comprise:
- a) from about 15% to about 20% by weight of CBD oil extract containing at least about 98% by weight of cannabidiol;
- b) from about 15% to about 40% by weight of high oleic acid olive oil;
- c) from about 0.5% to about 1% by weight of deoxycholic acid;
- d) from about 40% to about 80% by weight of carrier chosen from mannitol, colloidal silicon dioxide, and mixtures thereof.

In another embodiment of this aspect the compositions, comprise:
- a) from about 10% to about 20% by weight of CBD oil extract containing at least about 98% by weight of cannabidiol;
- b) from about 10% to about 40% by weight of high oleic acid olive oil;
- c) from about 0.5% to about 1% by weight of deoxycholic acid;
- d) from about 30% to about 85% by weight of a carrier chosen from mannitol, colloidal silicon dioxide, tapioca starch, gum Arabic, and mixtures thereof.

In one iteration of this embodiment the compositions comprise:
- a) from about 10% to about 20% by weight of CBD oil extract containing at least about 98% by weight of cannabidiol;
- b) from about 10% to about 40% by weight of high oleic acid olive oil;
- c) from about 0.5% to about 1% by weight of deoxycholic acid;
- d) from about 40% to about 70% by weight of carrier chosen from mannitol, colloidal silicon dioxide, and mixtures thereof.

In one embodiment of this aspect the compositions, comprise:
- a) from about 15% to about 20% by weight of CBD oil extract containing at least about 98% by weight of cannabidiol;
- b) from about 15% to about 40% by weight of high oleic acid olive oil;
- c) from about 0.5% to about 1% by weight of deoxycholic acid;
- d) from about 40% to about 80% by weight of a carrier chosen from mannitol, colloidal silicon dioxide, tapioca starch, gum Arabic, and mixtures thereof.

In one iteration of this embodiment the compositions comprise:
- a) from about 15% to about 20% by weight of CBD oil extract containing at least about 98% by weight of cannabidiol;
- b) from about 15% to about 40% by weight of high oleic acid olive oil;
- c) from about 0.5% to about 1% by weight of deoxycholic acid;
- d) from about 40% to about 80% by weight of carrier chosen from mannitol, colloidal silicon dioxide, and mixtures thereof.

In another aspect of the disclosed compositions, the compositions, comprise
- a) from about 5% to about 25% by weight of CBD oil extract containing at least about 98% by weight of cannabidiol;
- b) from about 5% to about 60% by weight of one or more edible oils;
- c) from about 0.1% to about 1% by weight of deoxycholic acid;
- d) the balance a carrier.

In one embodiment of this aspect the compositions, comprise:
- a) from about 5% to about 25% by weight of CBD oil extract containing at least about 98% by weight of cannabidiol;
- b) from about 5% to about 60% by weight of one or more edible oils chosen from sunflower oil, coconut oil, canola oil, palm oil, soybean oil, corn oil, safflower oil, and peanut oil;
- c) from about 0.1% to about 1% by weight of deoxycholic acid;
- d) from about 30% to about 85% by weight of a carrier chosen from mannitol, colloidal silicon dioxide, tapioca starch, gum Arabic, and mixtures thereof.

In one iteration of this embodiment the compositions comprise:
- a) from about 5% to about 25% by weight of CBD oil extract containing at least about 98% by weight of cannabidiol;
- b) from about 5% to about 60% by weight of sunflower oil;
- c) from about 0.1% to about 1% by weight of deoxycholic acid;
- d) from about 30% to about 85% by weight of carrier chosen from mannitol, colloidal silicon dioxide, and mixtures thereof.

In one iteration of this embodiment the compositions comprise:
- a) from about 5% to about 25% by weight of CBD oil extract containing at least about 98% by weight of cannabidiol;
- b) from about 5% to about 60% by weight of coconut;
- c) from about 0.1% to about 1% by weight of deoxycholic acid;
- d) from about 30% to about 85% by weight of carrier chosen from mannitol, colloidal silicon dioxide, and mixtures thereof.

In one iteration of this embodiment the compositions comprise:
- a) from about 5% to about 25% by weight of CBD oil extract containing at least about 98% by weight of cannabidiol;
- b) from about 5% to about 60% by weight of sesame oil;
- c) from about 0.1% to about 1% by weight of deoxycholic acid;
- d) from about 30% to about 85% by weight of carrier chosen from mannitol, colloidal silicon dioxide, and mixtures thereof.

In another embodiment of this aspect the compositions, comprise:
- a) from about 10% to about 20% by weight of CBD oil extract containing at least about 98% by weight of cannabidiol;
- b) from about 10% to about 40% by weight of one or more edible oils chosen from sunflower oil, coconut oil, canola oil, palm oil, soybean oil, corn oil, safflower oil, and peanut oil;
- c) from about 0.5% to about 1% by weight of deoxycholic acid;
- d) from about 30% to about 85% by weight of a carrier chosen from mannitol, colloidal silicon dioxide, tapioca starch, gum Arabic, and mixtures thereof.

In one iteration of this embodiment the compositions comprise:
- a) from about 10% to about 20% by weight of CBD oil extract containing at least about 98% by weight of cannabidiol;
- b) from about 10% to about 40% by weight of sunflower oil;
- c) from about 0.5% to about 1% by weight of deoxycholic acid;
- d) from about 30% to about 85% by weight of a carrier chosen from mannitol, colloidal silicon dioxide, tapioca starch, gum Arabic, and mixtures thereof.

In one iteration of this embodiment the compositions comprise:
- a) from about 10% to about 20% by weight of CBD oil extract containing at least about 98% by weight of cannabidiol;
- b) from about 10% to about 40% by weight of coconut oil;
- c) from about 0.5% to about 1% by weight of deoxycholic acid;
- d) from about 30% to about 85% by weight of a carrier chosen from mannitol, colloidal silicon dioxide, tapioca starch, gum Arabic, and mixtures thereof.

In one iteration of this embodiment the compositions comprise:
- a) from about 10% to about 20% by weight of CBD oil extract containing at least about 98% by weight of cannabidiol;
- b) from about 10% to about 40% by weight of sesame oil;
- c) from about 0.5% to about 1% by weight of deoxycholic acid;
- d) from about 30% to about 85% by weight of a carrier chosen from mannitol, colloidal silicon dioxide, tapioca starch, gum Arabic, and mixtures thereof.

In a further embodiment of this aspect the compositions, comprise:
- a) from about 15% to about 20% by weight of CBD oil extract containing at least about 98% by weight of cannabidiol;
- b) from about 15% to about 40% by weight of one or more edible oils chosen from sunflower oil, coconut oil, canola oil, palm oil, soybean oil, corn oil, safflower oil, and peanut oil;
- c) from about 0.5% to about 1% by weight of deoxycholic acid;
- d) from about 40% to about 80% by weight of a carrier chosen from mannitol, colloidal silicon dioxide, tapioca starch, gum Arabic, and mixtures thereof.

In one iteration of this embodiment the compositions comprise:
- a) from about 15% to about 20% by weight of CBD oil extract containing at least about 98% by weight of cannabidiol;
- b) from about 15% to about 40% by weight of sunflower oil;
- c) from about 0.5% to about 1% by weight of deoxycholic acid;
- d) from about 40% to about 80% by weight of a carrier chosen from mannitol, colloidal silicon dioxide, and mixtures thereof.

In one iteration of this embodiment the compositions comprise:
a) from about 15% to about 20% by weight of CBD oil extract containing at least about 98% by weight of cannabidiol;
b) from about 15% to about 40% by weight of coconut oil;
c) from about 0.5% to about 1% by weight of deoxycholic acid;
d) from about 40% to about 80% by weight of a carrier chosen from mannitol, colloidal silicon dioxide, and mixtures thereof.

In one iteration of this embodiment the compositions comprise:
a) from about 15% to about 20% by weight of CBD oil extract containing at least about 98% by weight of cannabidiol;
b) from about 15% to about 40% by weight of sesame oil;
c) from about 0.5% to about 1% by weight of deoxycholic acid;
d) from about 40% to about 80% by weight of a carrier chosen from mannitol, colloidal silicon dioxide, and mixtures thereof.

The disclosed compositions of this aspect comprise from about 5% to about 25% by weight of CBD oil. In one embodiment the disclosed compositions can comprise from about 10% to about 20% by weight of CBD oil. In one embodiment, the composition can comprise from about 15% to about 20% by weight of CBD oil. In another embodiment, the composition can comprise from about 10% to about 15% by weight of CBD oil. In a further embodiment, the composition can comprise from about 12% to about 17% by weight of CBD oil.

For example, the amount of CBD oil can be, for example, 5%, 6%, 7%, 8%, 9%, 10%, 11%, 12%, 13%, 14%, 15%, 16%, 17%, 18%, 19%, 20%, 21%, 22%, 23%, 24%, or 25%.

The disclosed composition of this aspect can comprise from about 5% to about 60% by weight of one or more edible oils chosen from sunflower oil, coconut oil, canola oil, palm oil, soybean oil, corn oil, safflower oil, and peanut oil. In one embodiment, the compositions comprise from about 10% to about 40% by weight of one or more edible oils. In one embodiment, the compositions comprise from about 15% to about 40% by weight of one or more edible oils. In one embodiment, the compositions comprise from about 20% to about 30% by weight of one or more edible oils. In one embodiment, the compositions comprise from about 25% to about 35% by weight of one or more edible oils. The disclosed composition of this aspect can comprise from about 0.5% to about 60% by weight of one or more edible oils, for example 5%, 6%, 7%, 8%, 9%, 10%, 11%, 12%, 13%, 14%, 15%, 16%, 17%, 18%, 19%, 20%, 21%, 22%, 23%, 24%, 25% 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, or 60% by weight, or any fractional amount thereof, of one or more edible oils.

In a yet further aspect the disclosed compositions, comprise:
a) from about 35 mg to about 150 mg by weight of CBD oil extract containing at least about 98% by weight of cannabidiol;
b) from about 70 mg to about 300 mg by weight of one or more edible oils chosen from sunflower oil, coconut oil, canola oil, palm oil, soybean oil, corn oil, safflower oil, and peanut oil;
c) from about 3 mg to about 13 mg by weight of deoxycholic acid;
d) from about 135 mg to about 560 mg of one or more carriers.

In one embodiment of this aspect the disclosed compositions, comprise:
a) from about 35 mg to about 150 mg by weight of CBD oil extract containing at least about 98% by weight of cannabidiol;
b) from about 70 mg to about 300 mg by weight of one or more edible oils;
c) from about 3 mg to about 13 mg by weight of deoxycholic acid;
d) from about 135 mg to about 560 mg of a carrier chosen from mannitol, colloidal silicon dioxide, tapioca starch, gum Arabic, and mixtures thereof.

In one embodiment of this aspect the disclosed compositions, comprise:
a) from about 35 mg to about 150 mg by weight of CBD oil extract containing at least about 98% by weight of cannabidiol;
b) from about 70 mg to about 300 mg by weight of high oleic acid olive oil;
c) from about 3 mg to about 13 mg by weight of deoxycholic acid;
d) from about 135 mg to about 560 mg of a carrier chosen from mannitol, colloidal silicon dioxide, and mixtures thereof.

In one embodiment of this aspect the disclosed compositions, comprise:
a) from about 35 mg to about 150 mg by weight of CBD oil extract containing at least about 98% by weight of cannabidiol;
b) from about 70 mg to about 300 mg by weight of sunflower oil;
c) from about 3 mg to about 13 mg by weight of deoxycholic acid;
d) from about 135 mg to about 560 mg of a carrier chosen from mannitol, colloidal silicon dioxide, and mixtures thereof.

In one embodiment of this aspect the disclosed compositions, comprise:
a) from about 35 mg to about 150 mg by weight of CBD oil extract containing at least about 98% by weight of cannabidiol;
b) from about 70 mg to about 300 mg by weight of coconut oil;
c) from about 3 mg to about 13 mg by weight of deoxycholic acid;
d) from about 135 mg to about 560 mg of a carrier chosen from mannitol, colloidal silicon dioxide, and mixtures thereof.

In one embodiment of this aspect the disclosed compositions, comprise:
a) from about 35 mg to about 150 mg by weight of CBD oil extract containing at least about 98% by weight of cannabidiol;
b) from about 70 mg to about 300 mg by weight of sesame seed oil;
c) from about 3 mg to about 13 mg by weight of deoxycholic acid;
d) from about 135 mg to about 560 mg of a carrier chosen from mannitol, colloidal silicon dioxide, and mixtures thereof.

In one non-limiting iteration of this embodiment the compositions comprise:
a) from about 35 mg to about 150 mg by weight of CBD oil extract containing at least about 98% by weight of cannabidiol;
b) from about 70 mg to about 300 mg by weight of high oleic acid olive oil;
c) from about 3 mg to about 13 mg by weight of deoxycholic acid;
d) from about 67 mg to about 280 mg by weight of colloidal silicon dioxide, and from about 68 mg to about 280 mg of mannitol, and mixtures thereof.

In one iteration of this embodiment the disclosed compositions, comprise:
a) from about 35 mg to about 120 mg by weight of CBD oil extract containing at least about 98% by weight of cannabidiol;
b) from about 70 mg to about 240 mg by weight of high oleic acid olive oil;
c) from about 3 mg to about 10.5 mg by weight of deoxycholic acid;
d) from about 135 mg to about 440 mg of a carrier chosen from mannitol, colloidal silicon dioxide, and mixtures thereof.

In one iteration of this embodiment the disclosed compositions, comprise:
a) from about 35 mg to about 120 mg by weight of CBD oil extract containing at least about 98% by weight of cannabidiol;
b) from about 70 mg to about 240 mg by weight of sunflower oil;
c) from about 3 mg to about 10.5 mg by weight of deoxycholic acid;
d) from about 135 mg to about 440 mg of a carrier chosen from mannitol, colloidal silicon dioxide, and mixtures thereof.

In one iteration of this embodiment the disclosed compositions, comprise:
a) from about 35 mg to about 120 mg by weight of CBD oil extract containing at least about 98% by weight of cannabidiol;
b) from about 70 mg to about 240 mg by weight of coconut oil;
c) from about 3 mg to about 10.5 mg by weight of deoxycholic acid;
d) from about 135 mg to about 440 mg of a carrier chosen from mannitol, colloidal silicon dioxide, and mixtures thereof.

In one iteration of this embodiment the disclosed compositions, comprise:
a) from about 35 mg to about 120 mg by weight of CBD oil extract containing at least about 98% by weight of cannabidiol;
b) from about 70 mg to about 240 mg by weight of sesame oil;
c) from about 3 mg to about 10.5 mg by weight of deoxycholic acid;
d) from about 135 mg to about 440 mg of a carrier chosen from mannitol, colloidal silicon dioxide, and mixtures thereof.

In a further iteration of this embodiment the disclosed compositions, comprise:
a) from about 35 mg to about 120 mg by weight of CBD oil extract containing at least about 98% by weight of cannabidiol;
b) from about 70 mg to about 240 mg by weight of high oleic acid olive oil;
c) from about 3 mg to about 10.5 mg by weight of deoxycholic acid;
d) from about 67 mg to about 220 mg by weight of colloidal silicon dioxide, and from about 68 mg to about 220 mg of mannitol, and mixtures thereof.

In a further iteration of this embodiment the disclosed compositions, comprise:
a) from about 35 mg to about 95 mg by weight of CBD oil extract containing at least about 98% by weight of cannabidiol;
b) from about 70 mg to about 190 mg by weight of high oleic acid olive oil;
c) from about 3 mg to about 8.5 mg by weight of deoxycholic acid;
d) from about 135 mg to about 360 mg of a carrier chosen from mannitol, colloidal silicon dioxide, and mixtures thereof.

In a further iteration of this embodiment the disclosed compositions, comprise:
a) from about 35 mg to about 95 mg by weight of CBD oil extract containing at least about 98% by weight of cannabidiol;
b) from about 70 mg to about 190 mg by weight of sunflower oil;
c) from about 3 mg to about 8.5 mg by weight of deoxycholic acid;
d) from about 135 mg to about 360 mg of a carrier chosen from mannitol, colloidal silicon dioxide, and mixtures thereof.

In a further iteration of this embodiment the disclosed compositions, comprise:
a) from about 35 mg to about 95 mg by weight of CBD oil extract containing at least about 98% by weight of cannabidiol;
b) from about 70 mg to about 190 mg by weight of coconut oil;
c) from about 3 mg to about 8.5 mg by weight of deoxycholic acid;
d) from about 135 mg to about 360 mg of a carrier chosen from mannitol, colloidal silicon dioxide, and mixtures thereof.

In a further iteration of this embodiment the disclosed compositions, comprise:
a) from about 35 mg to about 95 mg by weight of CBD oil extract containing at least about 98% by weight of cannabidiol;
b) from about 70 mg to about 190 mg by weight of sesame oil;
c) from about 3 mg to about 8.5 mg by weight of deoxycholic acid;
d) from about 135 mg to about 360 mg of a carrier chosen from mannitol, colloidal silicon dioxide, and mixtures thereof.

In a further iteration of this embodiment the disclosed compositions, comprise:
a) from about 35 mg to about 90 mg by weight of CBD oil extract containing at least about 98% by weight of cannabidiol;
b) from about 70 mg to about 190 mg by weight of sesame oil;
c) from about 3 mg to about 8.5 mg by weight of deoxycholic acid;
d) from about 135 mg to about 360 mg of a carrier chosen from mannitol, colloidal silicon dioxide, and mixtures thereof.

In another iteration of this embodiment the disclosed compositions, comprise:
- a) from about 35 mg to about 75 mg by weight of CBD oil extract containing at least about 98% by weight of cannabidiol;
- b) from about 70 mg to about 150 mg by weight of high oleic acid olive oil;
- c) from about 3 mg to about 6.6 mg by weight of deoxycholic acid;
- d) from about 135 mg to about 280 mg of a carrier chosen from mannitol, colloidal silicon dioxide, and mixtures thereof.

In another iteration of this embodiment the disclosed compositions, comprise:
- a) from about 35 mg to about 75 mg by weight of CBD oil extract containing at least about 98% by weight of cannabidiol;
- b) from about 70 mg to about 150 mg by weight of sunflower oil;
- c) from about 3 mg to about 6.6 mg by weight of deoxycholic acid;
- d) from about 135 mg to about 280 mg of a carrier chosen from mannitol, colloidal silicon dioxide, and mixtures thereof.

In another iteration of this embodiment the disclosed compositions, comprise:
- a) from about 35 mg to about 75 mg by weight of CBD oil extract containing at least about 98% by weight of cannabidiol;
- b) from about 70 mg to about 150 mg by weight of coconut oil;
- c) from about 3 mg to about 6.6 mg by weight of deoxycholic acid;
- d) from about 135 mg to about 280 mg of a carrier chosen from mannitol, colloidal silicon dioxide, and mixtures thereof.

In another iteration of this embodiment the disclosed compositions, comprise:
- a) from about 35 mg to about 75 mg by weight of CBD oil extract containing at least about 98% by weight of cannabidiol;
- b) from about 70 mg to about 150 mg by weight of sesame oil;
- c) from about 3 mg to about 6.6 mg by weight of deoxycholic acid;
- d) from about 135 mg to about 280 mg of a carrier chosen from mannitol, colloidal silicon dioxide, and mixtures thereof.

In a yet further embodiment of this aspect the disclosed compositions, comprise:
- a) from about 75 mg to about 150 mg by weight of CBD oil extract containing at least about 98% by weight of cannabidiol;
- b) from about 150 mg to about 300 mg by weight of high oleic acid olive oil;
- c) from about 6.6 mg to about 13 mg by weight of deoxycholic acid;
- d) from about 280 mg to about 560 mg of a carrier chosen from mannitol, colloidal silicon dioxide, and mixtures thereof In a yet further embodiment of this aspect the disclosed compositions, comprise:
- a) from about 75 mg to about 150 mg by weight of CBD oil extract containing at least about 98% by weight of cannabidiol;
- b) from about 150 mg to about 300 mg by weight of sunflower oil;
- c) from about 6.6 mg to about 13 mg by weight of deoxycholic acid;
- d) from about 280 mg to about 560 mg of a carrier chosen from mannitol, colloidal silicon dioxide, and mixtures thereof In a yet further embodiment of this aspect the disclosed compositions, comprise:
- a) from about 75 mg to about 150 mg by weight of CBD oil extract containing at least about 98% by weight of cannabidiol;
- b) from about 150 mg to about 300 mg by weight of coconut oil;
- c) from about 6.6 mg to about 13 mg by weight of deoxycholic acid;
- d) from about 280 mg to about 560 mg of a carrier chosen from mannitol, colloidal silicon dioxide, and mixtures thereof In a yet further embodiment of this aspect the disclosed compositions, comprise:
- a) from about 75 mg to about 150 mg by weight of CBD oil extract containing at least about 98% by weight of cannabidiol;
- b) from about 150 mg to about 300 mg by weight of sesame oil;
- c) from about 6.6 mg to about 13 mg by weight of deoxycholic acid;
- d) from about 280 mg to about 560 mg of a carrier chosen from mannitol, colloidal silicon dioxide, and mixtures thereof In a yet further embodiment of this aspect the disclosed compositions, comprise:
- a) from about 75 mg to about 120 mg by weight of CBD oil extract containing at least about 98% by weight of cannabidiol;
- b) from about 150 mg to about 240 mg by weight of high oleic acid olive oil;
- c) from about 6.6 mg to about 10.5 mg by weight of deoxycholic acid;
- d) from about 280 mg to about 4400 mg of a carrier chosen from mannitol, colloidal silicon dioxide, and mixtures thereof.

In a yet further embodiment of this aspect the disclosed compositions, comprise:
- a) from about 75 mg to about 150 mg by weight of CBD oil extract containing at least about 98% by weight of cannabidiol;
- b) from about 150 mg to about 300 mg by weight of sunflower oil;
- c) from about 6.6 mg to about 13 mg by weight of deoxycholic acid;
- d) from about 280 mg to about 560 mg of a carrier chosen from mannitol, colloidal silicon dioxide, and mixtures thereof In a yet further embodiment of this aspect the disclosed compositions, comprise:
- a) from about 75 mg to about 150 mg by weight of CBD oil extract containing at least about 98% by weight of cannabidiol;
- b) from about 150 mg to about 300 mg by weight of coconut oil;
- c) from about 6.6 mg to about 13 mg by weight of deoxycholic acid;
- d) from about 280 mg to about 560 mg of a carrier chosen from mannitol, colloidal silicon dioxide, and mixtures thereof In a yet further embodiment of this aspect the disclosed compositions, comprise:
- a) from about 75 mg to about 150 mg by weight of CBD oil extract containing at least about 98% by weight of cannabidiol;
- b) from about 150 mg to about 300 mg by weight of sesame oil;
- c) from about 6.6 mg to about 13 mg by weight of deoxycholic acid;
- d) from about 280 mg to about 560 mg of a carrier chosen from mannitol, colloidal silicon dioxide, and mixtures thereof In a yet further embodiment of this aspect the disclosed compositions, comprise:
- a) from about 95 mg to about 150 mg by weight of CBD oil extract containing at least about 98% by weight of cannabidiol;
- b) from about 190 mg to about 300 mg by weight of high oleic acid olive oil;
- c) from about 8.5 mg to about 13 mg by weight of deoxycholic acid;
- d) from about 360 mg to about 560 mg of a carrier chosen from mannitol, colloidal silicon dioxide, and mixtures thereof.

In a yet further embodiment of this aspect the disclosed compositions, comprise:
- a) from about 95 mg to about 150 mg by weight of CBD oil extract containing at least about 98% by weight of cannabidiol;
- b) from about 190 mg to about 300 mg by weight of sunflower oil;
- c) from about 8.5 mg to about 13 mg by weight of deoxycholic acid;
- d) from about 360 mg to about 560 mg of a carrier chosen from mannitol, colloidal silicon dioxide, and mixtures thereof.

In a yet further embodiment of this aspect the disclosed compositions, comprise:
- a) from about 95 mg to about 150 mg by weight of CBD oil extract containing at least about 98% by weight of cannabidiol;
- b) from about 190 mg to about 300 mg by weight of coconut oil;
- c) from about 8.5 mg to about 13 mg by weight of deoxycholic acid;
- d) from about 360 mg to about 560 mg of a carrier chosen from mannitol, colloidal silicon dioxide, and mixtures thereof.

In a yet further embodiment of this aspect the disclosed compositions, comprise:
- a) from about 95 mg to about 150 mg by weight of CBD oil extract containing at least about 98% by weight of cannabidiol;
- b) from about 190 mg to about 300 mg by weight of sesame oil;
- c) from about 8.5 mg to about 13 mg by weight of deoxycholic acid;
- d) from about 360 mg to about 560 mg of a carrier chosen from mannitol, colloidal silicon dioxide, and mixtures thereof.

In one non-limiting example of this aspect of the disclosed compositions, comprise:
- a) about 35 mg by weight of CBD oil extract containing at least about 98% by weight of cannabidiol;
- b) about 70 mg by weight of high oleic acid olive oil;
- c) about 3 mg by weight of deoxycholic acid;
- d) about 67 mg by weight of mannitol and about 68 mg by weight of colloidal silicon dioxide.

In another non-limiting example of this aspect of the disclosed compositions, comprise:
- a) about 75 mg by weight of CBD oil extract containing at least about 98% by weight of cannabidiol;
- b) about 150 mg by weight of high oleic acid olive oil;
- c) about 6.6 mg by weight of deoxycholic acid;
- d) about 139 mg by weight of mannitol and about 141 mg by weight of colloidal silicon dioxide.

In a yet still further non-limiting example of this disclosed compositions, comprise:
- a) about 75 mg by weight of CBD oil extract containing at least about 98% by weight of cannabidiol;
- b) about 150 mg by weight of high oleic acid olive oil;
- c) about 6.6 mg by weight of deoxycholic acid;
- d) about 143 mg by weight of mannitol and about 144 mg by weight of colloidal silicon dioxide.

In a yet another non-limiting example of this disclosed compositions, comprise:
- a) about 120 mg by weight of CBD oil extract containing at least about 98% by weight of cannabidiol;
- b) about 240 mg by weight of high oleic acid olive oil;
- c) about 10.5 mg by weight of deoxycholic acid;
- d) about 219 mg by weight of mannitol and about 221 mg by weight of colloidal silicon dioxide.

The disclosed compositions of this aspect comprise from about 35 mg to about 150 mg by weight of CBD oil extract containing at least about 98% by weight of cannabidiol. In one embodiment the compositions can comprise from about 35 mg to about 120 mg by weight of CBD oil extract containing at least about 98% by weight of cannabidiol. In another embodiment the compositions can comprise from about 35 mg to about 95 mg by weight of CBD oil extract containing at least about 98% by weight of cannabidiol. In further embodiment the compositions can comprise from about 35 mg to about 75 mg by weight of CBD oil extract containing at least about 98% by weight of cannabidiol. In a still further embodiment the compositions can comprise from about 75 mg to about 150 mg by weight of CBD oil extract containing at least about 98% by weight of cannabidiol. In a yet still further embodiment the compositions can comprise from about 75 mg to about 120 mg by weight of CBD oil extract containing at least about 98% by weight of cannabidiol. In a still another embodiment the compositions can comprise from about 95 mg to about 150 mg by weight of CBD oil extract containing at least about 98% by weight of cannabidiol.

The compositions can comprise 35 mg. 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg. 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, 99 mg, 100 mg, 101 mg, 102, mg, 103, mg, 104 mg, 105 mg, 106 mg, 107 mg, 108 mg, 109 mg, 110 mg, 111 mg, 112 mg, 113 mg, 114 mg, 115 mg, 116 mg, 117 mg, 118 mg, 119 mg, 120 mg, 121 mg, 122 mg, 123 mg, 124 mg, 125 mg, 126 mg, 127 mg, 128 mg, 129 mg, 130 mg 31 mg, 132 mg, 133 mg, 134 mg, 135 mg, 136 mg, 137 mg, 138 mg, 139 mg, 140 mg, 141 mg, 142 mg, 143 mg, 144 mg, 145 mg, 146 mg, 147 mg, 148 mg, 149 mg, or 150 mg, by weight of CBD oil extract containing at least about 98% by weight of cannabidiol.

The disclosed compositions of this aspect comprise from about 70 mg to about 300 mg by weight of one or more edible oils chosen from sunflower oil, coconut oil, canola oil, palm oil, soybean oil, corn oil, safflower oil, and peanut oil. In one embodiment the disclosed compositions comprise from about 70 mg to about 240 mg by weight of one or more edible oils. In another embodiment the disclosed compositions comprise from about 70 mg to about 190 mg by weight of one or more edible oils. In a further embodiment the disclosed compositions comprise from about 70 mg to about 150 mg by weight of one or more edible oils. In a still further embodiment the disclosed compositions comprise from about 150 mg to about 300 mg by weight of one or more edible oils. In a yet further embodiment the disclosed compositions comprise from about 90 mg to about 300 mg by weight of one or more edible oils.

The disclosed compositions of this aspect can comprise from about 80 mg to about 340 mg by weight of one or more edible oils, for example, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, 99 mg, 100 mg, 101 mg, 102, mg, 103, mg, 104 mg, 105 mg, 106 mg, 107 mg, 108 mg, 109 mg, 110 mg, 111 mg, 112 mg, 113 mg, 114 mg, 115 mg, 116 mg, 117 mg, 118 mg, 119 mg, 120 mg, 121 mg, 122 mg, 123 mg, 124 mg, 125 mg, 126 mg, 127 mg, 128 mg, 129 mg, 130 mg 31 mg, 132 mg, 133 mg, 134 mg, 135 mg, 136 mg, 137 mg, 138 mg, 139 mg, 140 mg, 141 mg, 142 mg, 143 mg, 144 mg, 145 mg, 146 mg, 147 mg, 148 mg, 149 mg, 150 mg, 151 mg, 152 mg, 153 mg, 154 mg, 155 mg, 156 mg, 157 mg, 158 mg, 159 mg, 160 mg, 161 mg, 162 mg, 163 mg, 164 mg, 165 mg, 166 mg, 167 mg, 168 mg, 169 mg, 170 mg, 171 mg, 172 mg, 173 mg, 174 mg, 175 mg, 167 mg, 177 mg, 178 mg, 179 mg, 180 mg, 181 mg, 182 mg, 183 mg, 184 mg, 185 mg, 186 mg, 187 mg, 188 mg, 189 mg, 190 mg, 191 mg, 192 mg, 193 mg, 194 mg, 195 mg, 196 mg, 197 mg, 198 mg, 199 mg, 200 mg, 201 mg, 202 mg, 203 mg, 204 mg, 205 mg, 206 mg, 207 mg, 208 mg, 209 mg, 210 mg, 211 mg, 212 mg, 213 mg, 214 mg, 215 mg, 216 mg, 217 mg, 218 mg, 219 mg, 220 mg, 221 mg, 222 mg, 223 mg, 224 mg, 225 mg, 226 mg, 227 mg, 228 mg, 229 mg, 230 mg, 231 mg, 232 mg, 233 mg, 234 mg, 235 mg, 236 mg, 237 mg, 238 mg, 239 mg, 240 mg, 241 mg, 242 mg, 243 mg, 244 mg, 245 mg, 246 mg, 247 mg, 248 mg, 249 mg, 250 mg, 251 mg, 252 mg, 253 mg, 254 mg, 255 mg, 256 mg, 257 mg, 258 mg, 259 mg, 260 mg, 261 mg, 262 mg, 263 mg, 264 mg, 265 mg, 266 mg, 267 mg, 268 mg, 269 mg, 270 mg, 271 mg, 272 mg, 273 mg, 274 mg, 275 mg, 276 mg, 277 mg, 278 mg, 279 mg, 280 mg, 281 mg, 282 mg, 283 mg, 284 mg, 285 mg, 286 mg, 287 mg, 288 mg, 289 mg, 290 mg, 290 mg, 291 mg, 292 mg, 293 mg, 294 mg, 295 mg, 296 mg, 297 mg, 298 mg, 299 mg, or 300 mg, of one or more edible oils.

According to this aspect the ratio of CBD oil extract containing at least about 98% by weight of cannabidiol to high oleic acid olive oil is from about 1:1 to about 1:3. For example, the ratio of CBD oil extract to olive oil can be 1:1, 1:1.1, 1:1.2, 1:1.3, 1:1.4, 1:1.5, 1:1.6, 1:1.7, 1:1.8, 1:1.9, 1:2, 1:2.1, 1:2.2, 1:2.3, 1:2.4, 1:2.5, 1:2.6, 1:2.7, 1:2.8, 1:2.9, or 1:3.

Table 3 discloses non-limiting examples of the disclosed compositions according to this aspect.

TABLE 3

| Ingredients (mg) | 1 | 2 | 3 | 4 | 5 |
|---|---|---|---|---|---|
| CBD oil[1] | 36.4 | 72.7 | 87.3 | 116.4 | 145.5 |
| High oleic acid olive oil | 72.7 | 145.5 | 174.6 | 232.7 | 290.9 |
| Deoxycholic acid | 3.3 | 6.5 | 7.8 | 10.4 | 13.1 |
| Partek-M ™ Mannitol | 69 | 138 | 165.6 | 220.8 | 275.9 |
| Aeroperl ™ 300 | 68.6 | 137.3 | 164.7 | 219.7 | 274.6 |
| Total | 250 | 500 | 650 | 800 | 1000 |

[1]CBD oil extract containing at least about 98% by weight of cannabidiol

According to this aspect the ratio of CBD oil extract containing at least about 98% by weight of cannabidiol to high oleic acid olive oil is from about 1:1 to about 1:3. For example, the ratio of CBD oil extract to olive oil can be 1:1, 1:1.1, 1:1.2, 1:1.3, 1:1.4, 1:1.5, 1:1.6, 1:1.7, 1:1.8, 1:1.9, 1:2, 1:2.1, 1:2.2, 1:2.3, 1:2.4, 1:2.5, 1:2.6, 1:2.7, 1:2.8, 1:2.9, or 1:3.

Edible Oils

The disclosed compositions can comprise one or more edible oils. The disclosed edible oils include oils that are primarily triglyceride-containing oils, however, some amount of diglycerides and monoglycerides can be present. Non-limiting examples of these oils are chosen from sunflower oil, coconut oil, olive oil, coconut oil, sesame seed oil, canola oil, palm oil, soybean oil, corn oil, safflower oil, peanut oil, and mixtures thereof. The disclosed compositions can comprise a single edible oil, in one example, the compositions can comprise sunflower oil. In a further example, the compositions can comprise high oleic acid containing sunflower oil. In another example, the compositions can comprise olive oil. In a still further example, the compositions can comprise high oleic acid containing olive oil. In a yet further example, the compositions can comprise coconut oil. In a still further example, the compositions can comprise high oleic acid containing sesame seed oil.

Bile Salts

The disclosed compositions can comprise one or more bile salts as described herein. The source of the bile salts can be any commercially available salts.

For the purposes of the present disclosure the terms "bile salts" and "bile acids" are used interchangeably herein. Bile acids are steroid acids found predominantly in the bile of mammals, for example, oxen, goats, and other cattle. The bile salts are conjugated with the amino acids taurine or glycine to produce bile salts. Extracted bile salts can comprise unconjugated bile acids.

Cholic acid, also known as 3α, 7α, 12α-trihydroxy-5β-cholan-24-oic acid is a primary bile acid found in bile extracts. It is insoluble in water (soluble in alcohol and acetic acid), obtained as a white crystalline substance. Salts of cholic acid are referred to as cholates. Cholic acid, along with chenodeoxycholic acid, is one of the two major bile acids produced by the liver of mammals, where it is synthesized from cholesterol. These two major bile acids are roughly equal in concentration in extracts.[4] Bile salts, per se, are made from choloyl-CoA, which exchanges its CoA with either glycine, or taurine, yielding glycocholic and taurocholic acid, respectively. Other bile salts include taurochenodeoxycholic acid and glycochenodeoxycholic acid (derivatives of chenodeoxycholic acid). These together with glycocholic and taurocholic acid make up the major constituents of bile salts.

One aspect of the disclosed bile salts are bile salts that contain from about 45% to about 55% by weight of cholic acid, deoxycholic acid, taurocholate, glycocholic acid, and mixtures thereof.

In one aspect the compositions of the present disclosure comprise from about 5% to about 15% by weight of bile salts. In one embodiment the compositions comprise from about 5% to about 10% by weight of bile salts. In one embodiment the compositions comprise from about 7% to about 10% by weight of bile salts. In one embodiment the compositions comprise from about 7% to about 12% by weight of bile salts. In one embodiment the compositions comprise from about 8% to about 11% by weight of bile salts. In one embodiment the compositions comprise from about 5% to about 12% by weight of bile salts.

The compositions of this aspect of the present disclosure can comprise from about 5% to about 15% by weight of bile salts, for example, 5%, 6%, 7%, 8%, 9%, 10%, 11%, 12%, 13%, 14%, or 15%, by weight of bile salts.

The compositions of this aspect of the present disclosure comprise from about 25 mg to about 100 mg by weight of bile salts. In one embodiment the compositions comprise from about 25 mg to about 65 mg by weight of one or more bile salts. In one embodiment the compositions comprise from about 50 mg to about 65 mg by weight of one or more bile salts. In one embodiment the compositions comprise from about 50 mg to about 100 mg by weight of one or more bile salts. In one embodiment the compositions comprise from about 65 mg to about 100 mg by weight of one or more bile salts. In one embodiment the compositions comprise from about 25 mg to about 65 mg by weight of one or more bile salts.

The compositions of the present disclosure comprise from about 25 mg to about 100 mg by weight of bile salts, for example, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg. 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, 99 mg, or 100 mg by weight of bile salts.

In another aspect of the present disclosure the compositions can comprise from about 0.1% to about 1% by weight of bile salts. In one embodiment the compositions can comprise from about 0.5% to about 1% by weight of bile salts. In another embodiment the compositions can comprise from about 0.5% to about 0.75% by weight of bile salts. In one embodiment the compositions can comprise from about 0.1% to about 0.75% by weight of bile salts. The disclosed compositions can comprise from about 0.1% to about 1% by weight of bile salts, for example, 0.1%, 0.15%, 0.2%, 0.25%, 0.3%, 0.35%, 0.4%, 0.45%, 0.5%, 0.55%, 0.6%, 0.65%, 0.7%, 0.75%, 0.8%, 0.85%, 0.9%, 0.95%, or 1%.

The compositions of this aspect of the present disclosure can comprise from about 75 mg to about 300 mg by weight of bile salts. In one embodiment the compositions can comprise from about 120 mg to about 300 mg by weight of bile salts. In one embodiment the compositions can comprise from about 180 mg to about 300 mg by weight of bile salts. In another embodiment the compositions can comprise from about 240 mg to about 300 mg by weight of bile salts. In a further embodiment the compositions can comprise from about 120 mg to about 240 mg by weight of bile salts. In a still further embodiment the compositions can comprise from about 180 mg to about 240 mg by weight of bile salts. In a still another embodiment the compositions can comprise from about 75 mg to about 240 mg by weight of bile salts. In yet another embodiment the compositions can comprise from about 75 mg to about 180 mg by weight of bile salts. In a still another embodiment the compositions can comprise from about 75 mg to about 120 mg by weight of bile salts.

The compositions of this aspect of the present disclosure can comprise from about 75 mg to about 300 mg by weight of bile salts, for example, 75 mg, 76 mg, 77 mg, 78 mg, 79 mg. 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, 99 mg, 100 mg, 101 mg, 102, mg, 103, mg, 104 mg, 105 mg, 106 mg, 107 mg, 108 mg, 109 mg, 110 mg, 111 mg, 112 mg, 113 mg, 114 mg, 115 mg, 116 mg, 117 mg, 118 mg, 119 mg, 120 mg, 121 mg, 122 mg, 123 mg, 124 mg, 125 mg, 126 mg, 127 mg, 128 mg, 129 mg, 130 mg 31 mg, 132 mg, 133 mg, 134 mg, 135 mg, 136 mg, 137 mg, 138 mg, 139 mg, 140 mg, 141 mg, 142 mg, 143 mg, 144 mg, 145 mg, 146 mg, 147 mg, 148 mg, 149 mg, 150 mg, 151 mg, 152 mg, 153 mg, 154 mg, 155 mg, 156 mg, 157 mg, 158 mg, 159 mg, 160 mg, 161 mg, 162 mg, 163 mg, 164 mg, 165 mg, 166 mg, 167 mg, 168 mg, 169 mg, 170 mg, 171 mg, 172 mg, 173 mg, 174 mg, 175 mg, 167 mg, 177 mg, 178 mg, 179 mg, 180 mg, 181 mg, 182 mg, 183 mg, 184 mg, 185 mg, 186 mg, 187 mg, 188 mg, 189 mg, 190 mg, 191 mg, 192 mg, 193 mg, 194 mg, 195 mg, 196 mg, 197 mg, 198 mg, 199 mg, 200 mg, 201 mg, 202 mg, 203 mg, 204 mg, 205 mg, 206 mg, 207 mg, 208 mg, 209 mg, 210 mg, 211 mg, 212 mg, 213 mg, 214 mg, 215 mg, 216 mg, 217 mg, 218 mg, 219 mg, 220 mg, 221 mg, 222 mg, 223 mg, 224 mg, 225 mg, 226 mg, 227 mg, 228 mg, 229 mg, 230 mg, 231 mg, 232 mg, 233 mg, 234 mg, 235 mg, 236 mg, 237 mg, 238 mg, 239 mg, 240 mg, 241 mg, 242 mg, 243 mg, 244 mg, 245 mg, 246 mg, 247 mg, 248 mg, 249 mg, 250 mg, 251 mg, 252 mg, 253 mg, 254 mg, 255 mg, 256 mg, 257 mg, 258 mg, 259 mg, 260 mg, 261 mg, 262 mg, 263 mg, 264 mg, 265 mg, 266 mg, 267 mg, 268 mg, 269 mg, 270 mg, 271 mg, 272 mg, 273 mg, 274 mg, 275 mg, 276 mg, 277 mg, 278 mg, 279 mg, 280 mg, 281 mg, 282 mg, 283 mg, 284 mg, 285 mg, 286 mg, 287 mg, 288 mg, 289 mg, 290 mg, 290 mg, 291 mg, 292 mg, 293 mg, 294 mg, 295 mg, 296 mg, 297 mg, 298 mg, 299 mg, or 300 mg.

In a further aspect the disclosed compositions can comprise from about 2 mg to about 7 mg by weight of the bile salt deoxycholic acid. In one embodiment the compositions can comprise from about 3.4 mg to about 7 mg by weight of the bile salt deoxycholic acid. In one embodiment the compositions can comprise from about 4.2 mg to about 7 mg by weight of the bile salt deoxycholic acid. In another embodiment the compositions can comprise from about 5.1 mg to about 7 mg by weight of the bile salt deoxycholic acid. In a further embodiment the compositions can comprise from about 2 mg to about 5.1 mg by weight of the bile salt deoxycholic acid. In a still further embodiment the compositions can comprise from about 2 mg to about 4.2 mg by weight of the bile salt deoxycholic acid.

The disclosed compositions of this aspect can comprise from about 2 mg to about 7 mg by weight of the bile salt deoxycholic acid, for example, 2 mg, 2.1 mg, 2.2 mg, 2.3 mg, 2.4 mg, 2.5 mg, 2.6 mg, 2.7 mg, 2.8 mg, 2.9 mg, 3 mg, 3.1 mg, 3.2 mg, 3.3 mg, 3.4 mg, 3.5 mg, 3.6 mg, 3.7 mg, 3.8 mg, 3.9 mg, 4 mg, 4.1 mg, 4.2 mg, 4.3 mg, 4.4 mg, 4.5 mg, 4.6 mg, 4.7 mg, 4.8 mg, 4.9 mg, 5 mg, 5.1 mg, 5.2 mg, 5.3 mg, 5.4 mg, 5.5 mg, 5.6 mg, 5.7 mg, 5.8 mg, 5.9 mg, 6 mg, 6.1 mg, 6.2 mg, 6.3 mg, 6.4 mg, 6.5 mg, 6.6 mg, 6.7 mg, 6.8 mg, 6.9 mg, or 7 mg.

Sodium Bicarbonate (NaHCO$_3$)

The disclosed compositions comprise from about 10% to about 20% by weight of sodium bicarbonate. In one embodiment the compositions comprise from about 12.5% to about 20% by weight of sodium bicarbonate. In another embodiment the compositions comprise from about 10% to about 17.5% by weight of sodium bicarbonate. In a further embodiment the compositions comprise from about 10% to about 15% by weight of sodium bicarbonate. The compositions can comprise, for example, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, or 20% by weight of NaHCO$_3$.

The compositions of the present disclosure comprise from about 35 mg to about 150 mg by weight of sodium bicarbonate. In one embodiment the compositions comprise from about 50 mg to about 115 mg by weight of sodium bicarbonate. In one embodiment the compositions comprise from about 35 mg to about 115 mg by weight of sodium bicarbonate. In one embodiment the compositions comprise from about 60 mg to about 150 mg by weight of sodium bicarbonate. In one embodiment the compositions comprise from about 90 mg to about 150 mg by weight of sodium bicarbonate. In one embodiment the compositions comprise from about 120 mg to about 150 mg by weight of sodium bicarbonate.

The compositions of the present disclosure comprise from about 35 mg to about 150 mg by weight of sodium bicarbonate, for example, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg. 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, 99 mg, 100 mg, 101 mg, 102, mg, 103, mg, 104 mg, 105 mg, 106 mg, 107 mg, 108 mg, 109 mg, 110 mg, 111 mg, 112 mg, 113 mg, 114 mg, 115 mg, 116 mg, 117 mg, 118 mg, 119 mg, 120 mg, 121 mg, 122 mg, 123 mg, 124 mg, 125 mg, 126 mg, 127 mg, 128 mg, 129 mg, 130 mg 31 mg, 132 mg, 133 mg, 134 mg, 135 mg, 136 mg, 137 mg, 138 mg, 139 mg, 140 mg, 141 mg, 142 mg, 143 mg, 144 mg, 145 mg, 146 mg, 147 mg, 148 mg, 149 mg, or 150 mg of sodium bicarbonate.

Carriers

In the present disclosure the term "carrier" and "adjunct ingredients" represent the same ingredients and these terms can be used interchangeably throughout the disclosure. For the purposes of the present disclosure "carriers" are further defined herein as compounds which can be suitably admixed with the active ingredients disclosed herein to serve one or more purposes, for example, as bulking agents, as delivery agents, as solubilizing agents, anti-caking agents, digestible fillers, and the like. The carriers can serve more than one purpose although listed individually under a particular topic, for example, generically as a carrier or specifically, inter alia, as an anti-caking agent, bulking agent, or delivery aid. In many instances the formulator can select a carrier that serves more than one purpose. The present disclosure in examples will set out a purpose for a particular carrier, however, this does not constrain the use of that carrier for other purposes.

In one aspect the disclosed carriers are polysaccharides. Non-limiting examples of poly saccharide carriers include inulin, galactogen, cellulose, chitin, pectin, psyllium, guar, hemicellulose, potato starch, and partially hydrolyzed polysaccharides. In another aspect the carriers are sugar alcohols, for example, sorbitol, erythritol, xylitol, lactitol, maltitol, mannitol, hydrogenated starch hydrolysates, isomaltose, or any combination thereof. In a further aspect carrier component is based on a native or chemically modified agar, alginates, carrageenan gum, cellulose, chitosan, chitin, cyclodextrin, dextran, gellan gum, glycogen, glycosaminoglycan, gum karaya, inulin, pectin, polydextrose, xanthan gum, or any other starches, gums or other polysaccharide, including functionalized derivatives, dextrinized, hydrolyzed, oxidized, alkylated, hydroxyalkylated, acetylated, fractionated, and physically modified starches and mixtures thereof. In some embodiments glycerin and/or propylene glycol can be added as a carrier.

In another aspect the carrier is chosen from gum Arabic, inulin, mannitol, silicon dioxide, colloidal silicon dioxide, microcrystalline cellulose, D-lactose monohydrate, tapioca starch, tapioca flour, quillaia, or mixtures thereof. In a further example the carrier is gum Arabic. In another example the carrier is inulin. In a yet another example the carrier is microcrystalline cellulose. In a still further example, the carrier is D-lactose monohydrate. In a still another example the carrier is quillaia. The carrier can be a combination of gum Arabic, inulin, microcrystalline cellulose, D-lactose monohydrate, or quillaia.

In one non-limiting example the carrier is Partek™ mannitol. In a further non-limiting example, the carrier is a microcrystalline cellulose. In a still further example, the carrier is colloidal silicon dioxide.

In general, depending upon the particular aspect, embodiment, iteration, or example, the disclosed compositions can comprise from about 5% to about 95% by weight of the disclosed compositions.

In one aspect of the present disclosure the compositions comprise from about 35% to about 75% by weight of one or more carriers. In one embodiment of this aspect the carriers are chosen from gum Arabic, tapioca starch, tapioca flour, silicon dioxide, mannitol, colloidal silicon dioxide, microcrystalline cellulose, and mixture thereof. In one iteration of this embodiment the carriers comprise tapioca starch, colloidal silicon dioxide, and mixture thereof.

In a further embodiment of this aspect the compositions comprise from about 45% to about 70% by weight of one or more carriers. In another embodiment of this aspect the compositions comprise from about 45% to about 55% by weight of one or more carriers. According to this aspect of the present disclosure the compositions comprise from about 35% to about 75% by weight of one or more carriers, for example, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, or 70%.

In this aspect of the disclosed compositions the compositions comprise from about 120 mg to about 500 mg by weight of one or more carriers. In a further embodiment the disclosed compositions comprise from about 120 mg to about 324 mg by weight of one or more carriers. In a further embodiment the disclosed compositions comprise from about 250 mg to about 324 mg by weight of one or more carriers. In a further embodiment the disclosed compositions comprise from about 324 mg to about 500 mg by weight of one or more carriers.

In one iteration the carriers comprise tapioca starch and colloidal silicon dioxide and mixtures thereof.

In this aspect the compositions comprise from about 120 mg to about 500 mg by weight of one or more carriers, for example, 120 mg, 121 mg, 122 mg, 123 mg, 124 mg, 125 mg, 126 mg, 127 mg, 128 mg, 129 mg, 130 mg 31 mg, 132 mg, 133 mg, 134 mg, 135 mg, 136 mg, 137 mg, 138 mg, 139 mg, 140 mg, 141 mg, 142 mg, 143 mg, 144 mg, 145 mg, 146 mg, 147 mg, 148 mg, 149 mg, 150 mg, 151 mg, 152 mg, 153 mg, 154 mg, 155 mg, 156 mg, 157 mg, 158 mg, 159 mg, 160 mg, 161 mg, 162 mg, 163 mg, 164 mg, 165 mg, 166 mg, 167 mg, 168 mg, 169 mg, 170 mg, 171 mg, 172 mg, 173 mg, 174 mg, 175 mg, 167 mg, 177 mg, 178 mg, 179 mg, 180 mg, 181 mg, 182 mg, 183 mg, 184 mg, 185 mg, 186 mg, 187 mg, 188 mg, 189 mg, 190 mg, 191 mg, 192 mg, 193 mg, 194 mg, 195 mg, 196 mg, 197 mg, 198 mg, 199 mg, 200 mg, 201 mg, 202 mg, 203 mg, 204 mg, 205 mg, 206 mg, 207 mg, 208 mg, 209 mg, 210 mg, 211 mg, 212 mg, 213 mg, 214 mg, 215 mg, 216 mg, 217 mg, 218 mg, 219 mg, 220 mg, 221 mg, 222 mg, 223 mg, 224 mg, 225 mg, 226 mg, 227 mg, 228 mg, 229 mg, 230 mg, 231 mg, 232 mg, 233 mg, 234 mg, 235 mg, 236 mg, 237 mg, 238 mg, 239 mg, 240 mg, 241 mg, 242 mg, 243 mg, 244 mg, 245 mg, 246 mg, 247 mg, 248 mg, 249 mg, 250 mg, 251 mg, 252 mg, 253 mg, 254 mg, 255 mg, 256 mg, 257 mg, 258 mg, 259 mg, 260 mg, 261 mg, 262 mg, 263 mg, 264 mg, 265 mg, 266 mg, 267 mg, 268 mg, 269 mg, 270 mg, 271 mg, 272 mg, 273 mg, 274 mg, 275 mg, 276 mg, 277 mg, 278 mg, 279 mg, 280 mg, 281 mg, 282 mg, 283 mg, 284 mg, 285 mg, 286 mg, 287 mg, 288 mg, 289 mg, 290 mg, 290 mg, 291 mg, 292 mg, 293 mg, 294 mg, 295 mg, 296 mg, 297 mg, 298 mg, 299 mg, 300 mg, 304 mg, 305 mg, 306 mg, 307 mg, 308 mg, 309 mg, 310 mg, 311 mg, 312 mg, 313 mg, 314 mg, 315 mg, 316 mg, 317 mg, 318 mg, 319 mg, 320 mg, 321 mg, 322 mg, 323 mg, 324 mg, 325 mg, 326 mg, 327 mg, 328 mg, 329 mg, 330 mg, 331 mg, 332 mg, 333 mg, 334 mg, 335 mg, 336 mg, 337 mg, 338 mg, 339 mg, 340 mg, 341 mg, 342 mg, 343 mg, 344 mg, 345 mg, 346 mg, 347 mg, 348 mg, 349 mg, 350 mg, 351 mg, 352 mg, 353 mg, 354 mg, 355 mg, 356 mg, 357 mg, 358 mg, 359 mg, 360 mg, 361 mg, 362 mg, 363 mg, 364 mg, 365 mg, 366 mg, 367 mg, 368 mg, 369 mg, 370 mg, 371 mg, 372 mg, 373 mg, 374 mg, 375 mg, 376 mg, 377 mg, 378 mg, 379 mg, 380 mg, 381 mg, 382 mg, 383 mg, 384 mg, 385 mg, 386 mg, 387 mg, 388 mg, 389 mg, 390 mg, 390 mg, 391 mg, 392 mg, 393 mg, 394 mg, 395 mg, 396 mg, 397 mg, 398 mg, 399 mg, 400 mg, 401 mg, 402 mg, 403 mg, 404 mg, 405 mg, 406 mg, 407 mg, 408 mg, 409 mg, 410 mg, 411 mg, 412 mg, 413 mg, 414 mg, 415 mg, 416 mg, 417 mg, 418 mg, 419 mg, 420 mg, 421 mg, 422 mg, 423 mg, 424 mg, 425 mg, 426 mg, 427 mg, 428 mg, 429 mg, 430 mg, 431 mg, 432 mg, 433 mg, 434 mg, 435 mg, 436 mg, 437 mg, 438 mg, 439 mg, 440 mg, 441 mg, 442 mg, 443 mg, 444 mg, 445 mg, 446 mg, 447 mg, 448 mg, 449 mg, 450 mg, 451 mg, 452 mg, 453 mg, 454 mg, 455 mg, 456 mg, 457 mg, 458 mg, 459 mg, 460 mg, 461 mg, 462 mg, 463 mg, 464 mg, 465 mg, 466 mg, 467 mg, 468 mg, 469 mg, 470 mg, 471 mg, 472 mg, 473 mg, 474 mg, 475 mg, 476 mg, 477 mg, 478 mg, 479 mg, 480 mg, 481 mg, 482 mg, 483 mg, 484 mg, 485 mg, 486 mg, 487 mg, 488 mg, 489 mg, 490 mg, 490 mg, 491 mg, 492 mg, 493 mg, 494 mg, 495 mg, 496 mg, 497 mg, 498 mg, 499 mg, or 500 mg by weight of one or more carriers.

In another aspect of the present disclosure the compositions comprise from about 30% to about 85% by weight of one or more carriers. In one embodiment of this aspect the carriers are chosen from gum Arabic, tapioca starch, tapioca flour, silicon dioxide, mannitol, colloidal silicon dioxide, microcrystalline cellulose, and mixture thereof. In one iteration of this embodiment the carriers comprise tapioca starch, colloidal silicon dioxide, and mixture thereof.

In one embodiment the compositions comprise from about 40% to about 70% by weight of one or more carriers. The compositions comprise from about 30% to about 85% by weight of one or more carriers, for example, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, or 85% by weight of one or more carriers.

In this aspect of the disclosed compositions the compositions comprise from about 110 mg to about 465 mg by weight of one or more carriers. In one embodiment the compositions the compositions comprise from about 180 mg to about 465 mg by weight of one or more carriers. In another embodiment the compositions the compositions comprise from about 270 mg to about 465 mg by weight of one or more carriers. In further embodiment the compositions the compositions comprise from about 365 mg to about 465 mg by weight of one or more carriers. In a yet further embodiment the compositions the compositions comprise from about 180 mg to about 465 mg by weight of one or more carriers. In a still further embodiment the compositions the compositions comprise from about 110 mg to about 180 mg by weight of one or more carriers. In yet another embodiment the compositions the compositions comprise from about 110 mg to about 270 mg by weight of one or more carriers. In still another embodiment the compositions the compositions comprise from about 180 mg to about 270 mg by weight of one or more carriers.

In this aspect of the disclosed compositions the compositions comprise from about 110 mg to about 465 mg by weight of one or more carriers, for example, 110 mg, 111 mg, 112 mg, 113 mg, 114 mg, 115 mg, 116 mg, 117 mg, 118 mg, 119 mg, 120 mg, 121 mg, 122 mg, 123 mg, 124 mg, 125 mg, 126 mg, 127 mg, 128 mg, 129 mg, 130 mg, 131 mg, 132 mg, 133 mg, 134 mg, 135 mg, 136 mg, 137 mg, 138 mg, 139 mg, 140 mg, 141 mg, 142 mg, 143 mg, 144 mg, 145 mg, 146 mg, 147 mg, 148 mg, 149 mg, 150 mg, 151 mg, 152 mg, 153 mg, 154 mg, 155 mg, 156 mg, 157 mg, 158 mg, 159 mg, 160 mg, 161 mg, 162 mg, 163 mg, 164 mg, 165 mg, 166 mg, 167 mg, 168 mg, 169 mg, 170 mg, 171 mg, 172 mg, 173 mg, 174 mg, 175 mg, 167 mg, 177 mg, 178 mg, 179 mg, 180 mg, 181 mg, 182 mg, 183 mg, 184 mg, 185 mg, 186 mg, 187 mg, 188 mg, 189 mg, 190 mg, 191 mg, 192 mg, 193 mg, 194 mg, 195 mg, 196 mg, 197 mg, 198 mg, 199 mg, 200 mg, 201 mg, 202 mg, 203 mg, 204 mg, 205 mg, 206 mg, 207 mg, 208 mg, 209 mg, 210 mg, 211 mg, 212 mg, 213 mg, 214 mg, 215 mg, 216 mg, 217 mg, 218 mg, 219 mg, 220 mg, 221 mg, 222 mg, 223 mg, 224 mg, 225 mg, 226 mg, 227 mg, 228 mg, 229 mg, 230 mg, 231 mg, 232 mg, 233 mg, 234 mg, 235 mg, 236 mg, 237 mg, 238 mg, 239 mg, 240 mg, 241 mg, 242 mg, 243 mg, 244 mg, 245 mg, 246 mg, 247 mg, 248 mg, 249 mg, 250 mg, 251 mg, 252 mg, 253 mg, 254 mg, 255 mg, 256 mg, 257 mg, 258 mg, 259 mg, 260 mg, 261 mg, 262 mg, 263 mg, 264 mg, 265 mg, 266 mg, 267 mg, 268 mg, 269 mg, 270 mg, 271 mg, 272 mg, 273 mg, 274 mg, 275 mg, 276 mg, 277 mg, 278 mg, 279 mg, 280 mg, 281 mg, 282 mg, 283 mg, 284 mg, 285 mg, 286 mg, 287 mg, 288 mg, 289 mg, 290 mg, 290 mg, 291 mg, 292 mg, 293 mg, 294 mg, 295 mg, 296 mg, 297 mg, 298 mg, 299 mg, 300 mg, 304 mg, 305 mg, 306 mg, 307 mg, 308 mg, 309 mg, 310 mg, 311 mg, 312 mg, 313 mg, 314 mg, 315 mg, 316 mg, 317 mg, 318 mg, 319 mg, 320 mg, 321 mg, 322 mg, 323 mg, 324 mg, 325 mg, 326 mg, 327 mg, 328 mg, 329 mg, 330 mg, 331 mg, 332 mg, 333 mg, 334 mg, 335 mg, 336 mg, 337 mg, 338 mg, 339 mg, 340 mg, 341 mg, 342 mg, 343 mg, 344 mg, 345 mg, 346 mg, 347 mg, 348 mg, 349 mg, 350 mg, 351 mg, 352 mg, 353 mg, 354 mg, 355 mg, 356 mg, 357 mg, 358 mg, 359 mg, 360 mg, 361 mg, 362 mg, 363 mg, 364 mg, 365 mg, 366 mg, 367 mg, 368 mg, 369 mg, 370 mg, 371 mg, 372 mg, 373 mg, 374 mg, 375 mg, 376 mg, 377 mg, 378 mg, 379 mg, 380 mg, 381 mg, 382 mg, 383 mg, 384 mg, 385 mg, 386 mg, 387 mg, 388 mg, 389 mg, 390 mg, 390 mg, 391 mg, 392 mg, 393 mg, 394 mg, 395 mg, 396 mg, 397 mg, 398 mg, 399 mg, 400 mg, 401 mg, 402 mg, 403 mg, 404 mg, 405 mg, 406 mg, 407 mg, 408 mg, 409 mg, 410 mg, 411 mg, 412 mg, 413 mg, 414 mg, 415 mg, 416 mg, 417 mg, 418 mg, 419 mg, 420 mg, 421 mg, 422 mg, 423 mg, 424 mg, 425 mg, 426 mg, 427 mg, 428 mg, 429 mg, 430 mg, 431 mg, 432 mg, 433 mg, 434 mg, 435 mg, 436 mg, 437 mg, 438 mg, 439 mg, 440 mg, 441 mg, 442 mg, 443 mg, 444 mg, 445 mg, 446 mg, 447 mg, 448 mg, 449 mg, 450 mg, 451 mg, 452 mg, 453 mg, 454 mg, 455 mg, 456 mg, 457 mg, 458 mg, 459 mg, 460 mg, 461 mg, 462 mg, 463 mg, 464 mg, or 465 mg by weight of one or more carriers.

A non-limiting listing of carriers suitable for use in the disclosed composition include carriers which can also serve as binders, pH stabilizers, disintegrants, and lubricants, for example, lactose monohydrate, mannitol, polyvinylpyrrolidone, crosspovidone, tapioca starch, citric acid, sodium citrate, magnesium stearate, calcium carbonate, magnesium carbonate, calcium stearate, magnesium stearate, tricalcium phosphate; powdered cellulose; magnesium stearate; sodium ferrocyanide; potassium ferrocyanide; calcium ferrocyanide; calcium phosphate; sodium silicate; calcium silicate; magnesium trisilicate; sodium aluminosilicate; potassium aluminum silicate; calcium aluminosilicate; bentonite; aluminum silicate; stearic acid; polydimethylsiloxane, and the like.

Methods

Disclosed herein are methods for treating epilepsy wherein the epilepsy can be manifested in any of its recognized or categorized forms. In one aspect disclosed herein is a method of reducing seizures in a subject suffering from epilepsy, comprising administering to the patient in need of treatment a composition disclosed herein.

Epilepsy

The term epilepsy is defined herein in general as "a central nervous system (neurological) disorder in which brain activity becomes abnormal, causing seizures or periods of unusual behavior, sensations and sometimes loss of awareness."

Without wishing to be limited by theory epileptic seizure symptoms can vary widely. Some individuals with epilepsy simply stare blankly for a few seconds during a seizure, while others repeatedly twitch their arms or legs. Having a single seizure is not determinative that an individual suffers from epilepsy. A consensus requires at least two seizures without a known trigger (unprovoked seizures) that happen at least 24 hours apart are generally required for an epilepsy diagnosis. Typically epilepsy is characterized by one or more symptoms, inter alia, temporary confusion, a staring spell, stiff muscles, uncontrollable jerking movements of the arms and legs, loss of consciousness or awareness, psychological symptoms including fear, anxiety, or déjà vu.

There are various generally recognized forms of seizures:
i) Absence seizures previously known as petit mal seizures. These seizures typically occur in children. They're characterized by staring into space with or without subtle body movements such as eye blinking or lip smacking and only last between 5-10 seconds. These seizures may occur in clusters, happening as often as 100 times per day, and cause a brief loss of awareness.
ii) Tonic seizures which cause stiff muscles and may affect consciousness. These seizures typically affect muscles in a subject's back, arms and legs and which can result in the subject falling to the ground.
iii) Atonic seizures, also known as drop seizures, cause a loss of muscle control. Since this type of seizure most often affects the legs, it often causes the subject to suddenly collapse or fall down.
iv) Clonic seizures are associated with repeated or rhythmic, jerking muscle movements. These seizures usually affect the neck, face and arms.
v) Myoclonic seizures usually appear as sudden brief jerks or twitches and usually affect the upper body, arms and legs.
vi) Tonic-clonic seizures, previously known as grand mal seizures, are the most dramatic type of epileptic seizure. They can cause an abrupt loss of consciousness and body stiffening, twitching and shaking. These seizures can cause a loss of bladder control or the subject biting the tongue.

Treatment Resistant Epilepsy

In addition to the generally recognized seizures listed above there are individual syndromes related to epilepsy such as treatment resistant childhood onset epilepsy. Especially those syndromes that are generally not responsive to treatment with standard anti-epileptic drugs For example the following are non-limiting examples of childhood epilepsies Dravet Syndrome; Myoclonic-Absence Epilepsy; Lennox-Gastaut syndrome; Generalized Epilepsy of unknown origin; CDKL5 mutation; Aicardi syndrome; bilateral polymicrogyria; Dup15q; SNAP25; and febrile infection related epilepsy syndrome (FIRES); benign rolandic epilepsy; juvenile myoclonic epilepsy; infantile spasm (West syndrome); and Landau-Kleffner syndrome.

Without wishing to be limited by theory Dravet syndrome is an epilepsy syndrome that begins in infancy or early childhood and can include a spectrum of symptoms ranging from mild to severe. Children with Dravet syndrome initially show focal (confined to one area) or generalized (throughout the brain) convulsive seizures that start before 15 months of age (often before age one). These initial seizures are often prolonged and involve half of the body and may be followed by seizures that switch to the other side of the body. Other seizure types emerge after 12 months of age and can be quite varied. Status epilepticus-a state of continuous seizure requiring emergency medical care—may occur frequently, particularly in the first five years of life. The U.S. Food and Drug Administration (FDA) approved cannabidiol to treat seizures with Dravet syndrome in people ages 2 and older Therefore, the present compositions provide a therapy to treat Dravet syndrome in a subject Without wishing to be limited by theory Lennox-Gastaut syndrome is a severe condition characterized by recurrent seizures (epilepsy) that begin early in life. Affected individuals have multiple types of seizures, a particular pattern of brain activity (called slow spike-and-wave) measured by a test called an electroencephalogram (EEG), and impaired mental abilities.

In Lennox-Gastaut syndrome, epilepsy begins in early childhood, usually between ages 3 and 5. The most common seizure type is tonic seizures, which cause the muscles to stiffen (contract) uncontrollably. These seizures typically occur during sleep; they may also occur during wakefulness and cause sudden falls. Also common are atypical absence seizures, which cause a very brief partial or complete loss of consciousness. Additionally, many affected individuals have episodes called drop attacks, which cause sudden falls that can result in serious or life-threatening injuries. Drop attacks may be caused by sudden loss of muscle tone (described as atonic) or by abnormal muscle contraction (described as tonic) Other types of seizures have been reported less frequently in people with Lennox-Gastaut syndrome. Seizures associated with Lennox-Gastaut syndrome often do not respond well to therapy with anti-epileptic medications. Therefore, the present compositions provide a therapy to treat Lennox-Gastaut syndrome in a subject.

Without wishing to be limited by theory Aicardi Syndrome is caused by a genetic malformation which results in complete or partial absence of the corpus callosum in the brain. Children suffering from Aicardi syndrome often additionally present with retinal abnormalities. Seizures usually begin in infancy (typically as infantile spasms), which tend to progress to recurrent seizures that can be difficult to treat. The seizures associated with Aicardi Syndrome include focal seizures with impairment; infantile spasm; clonic seizures; tonic seizures; tonic-clonic seizures; atonic seizures; myoclonic seizures; absence seizures; and focal seizures evolving to secondary generalized seizures. In many instances Aicardi Syndrome is resistant to treatment with standard anti-seizure drugs. Therefore, the present compositions provide a therapy to treat Aicardi syndrome in a subject.

Any of the herein disclosed compositions can be used in treating epilepsy. In one aspect disclosed herein is a method for treating epilepsy, comprising administering to a patient in need a composition comprising:
- a) from about 5% to about 20% by weight of CBD oil containing from about 88% to about 92% by weight of cannabidiol;
- b) from about 15% to about 40% by weight of high oleic acid sunflower oil;
- c) from about 5% to about 15% by weight of one or more bile salts; and
- d) from about 35% to about 75% by weight of one or more carriers.

In one embodiment of this aspect the compositions, comprise:
- a) from about 30 mg to about 135 mg of CBD oil containing from about 88% to about 91% by weight of cannabidiol;
- b) from about 60 mg to about 270 mg by weight of high oleic acid sunflower oil;
- c) from about 25 mg to about 100 mg by weight of one or more bile salts wherein the salts contain from about 45% to about 55% by weight of cholic acid, deoxycholic acid, taurocholate, glycocholic acid, and mixtures thereof; and d) from 120 mg to about 500 mg by weight of one or more carriers.

In a further aspect disclosed herein is a method for treating epilepsy, comprising administering to a patient in need a composition comprising:
- a) from about 5% to about 25% by weight of CBD oil containing from about 88% to about 91% by weight of cannabidiol;
- b) from about 5% to about 60% by weight of one or more edible oils;
- c) from about 0.1% to about 1% by weight of bile salts containing from about 45% to about 55% by weight of cholic acid, deoxycholic acid, taurocholate; glycocholic acid, and mixtures thereof;
- d) from about 10% to about 20% by weight of sodium bicarbonate; and
- e) the balance a carrier.

In one embodiment of this aspect the compositions comprise:
- a) from about 5 mg to about 32 mg by weight of CBD oil containing from about 88% to about 91% by weight of cannabidiol;
- b) from about 10 mg to about 65 mg by weight of one or more edible oils chosen from sunflower oil, coconut oil, canola oil, palm oil, soybean oil, corn oil, safflower oil, peanut oil, and mixtures thereof;
- c) from about 75 mg to about 300 mg by weight of bile salts containing from about 45% to about 55% by weight of cholic acid, deoxycholic acid, taurocholate; glycocholic acid, and mixtures thereof;
- d) from about 35 mg to about 150 mg by weight of sodium bicarbonate; and
- e) from about 110 mg to about 465 mg of a carrier.

In a yet further aspect disclosed herein is a method for treating epilepsy, comprising administering to a patient in need a composition comprising:
- a) from about 5% to about 25% by weight of CBD oil extract containing at least about 98% by weight of cannabidiol;
- b) from about 5% to about 60% by weight of high oleic acid olive oil;
- c) from about 0.1% to about 1% by weight of deoxycholic acid;
- d) from about 10% to about 20% by weight of sodium bicarbonate; and
- e) the balance a carrier.

In one embodiment of this aspect the compositions comprise:
- a) from about 40 mg to about 170 mg by weight of CBD oil extract containing at least about 98% by weight of cannabidiol;
- b) from about 80 mg to about 340 mg by weight of one or more edible oils;
- c) from about 1.5 mg to about 8 mg by weight of deoxycholic acid;
- d) from about 35 mg to about 150 mg by weight of sodium bicarbonate; and
- e) from about 80 mg to about 350 mg of one or more carriers.

Disclosed herein is a method for treating Dravet Syndrome in a patient suffering from Dravet Syndrome and in need of treatment, comprising administering to the patient in need of treatment a composition comprising:
- a) from about 5% to about 20% by weight of CBD oil containing from about 88% to about 92% by weight of cannabidiol;
- b) from about 15% to about 40% by weight of high oleic acid sunflower oil;
- c) from about 5% to about 15% by weight of one or more bile salts; and
- d) from about 35% to about 75% by weight of one or more carriers.

In a further aspect the method comprises administering to the patient in need of treatment a composition comprising:
- a) from about 30 mg to about 135 mg of CBD oil containing from about 88% to about 91% by weight of cannabidiol;
- b) from about 60 mg to about 270 mg by weight of high oleic acid sunflower oil;
- c) from about 25 mg to about 100 mg by weight of one or more bile salts wherein the salts contain from about 45% to about 55% by weight of cholic acid, deoxycholic acid, taurocholate, glycocholic acid, and mixtures thereof; and
- d) from 120 mg to about 500 mg by weight of one or more carriers.

In another aspect the method comprises administering to the patient in need of treatment a composition comprising:
  a) from about 5 mg to about 32 mg by weight of CBD oil containing from about 88% to about 91% by weight of cannabidiol;
  b) from about 10 mg to about 65 mg by weight of one or more edible oils chosen from sunflower oil, coconut oil, canola oil, palm oil, soybean oil, corn oil, safflower oil, peanut oil, and mixtures thereof;
  c) from about 75 mg to about 300 mg by weight of bile salts containing from about 45% to about 55% by weight of cholic acid, deoxycholic acid, taurocholate; glycocholic acid, and mixtures thereof;
  d) from about 35 mg to about 150 mg by weight of sodium bicarbonate; and
  e) from about 110 mg to about 465 mg of a carrier.

In a further aspect disclosed is method for treating epilepsy in a subject, comprising administering to the subject a composition comprising:
  a) from about 35 mg to about 150 mg by weight of CBD oil extract containing at least about 98% by weight of cannabidiol;
  b) from about 70 mg to about 300 mg by weight of high oleic acid olive oil;
  c) from about 3 mg to about 13 mg by weight of deoxycholic acid;
  d) from about 135 mg to about 560 mg of one or more carriers chosen from mannitol, colloidal silicon dioxide, and mixtures thereof.

In a non-limiting example of this aspect, the composition comprises:
  a) about 35 mg by weight of CBD oil extract containing at least about 98% by weight of cannabidiol;
  b) about 70 mg by weight of high oleic acid olive oil;
  c) about 3 mg by weight of deoxycholic acid;
  d) about 67 mg by weight of mannitol and about 68 mg by weight of colloidal silicon dioxide.

In a still further non-limiting example of this aspect, the composition comprises:
  a) about 75 mg by weight of CBD oil extract containing at least about 98% by weight of cannabidiol;
  b) about 150 mg by weight of high oleic acid olive oil;
  c) about 6.6 mg by weight of deoxycholic acid;
  d) about 139 mg by weight of mannitol and about 141 mg by weight of colloidal silicon dioxide.

In a yet further non-limiting example of this aspect of the disclosed methods, the composition comprises:
  a) about 120 mg by weight of CBD oil extract containing at least about 98% by weight of cannabidiol;
  b) about 240 mg by weight of high oleic acid olive oil;
  c) about 10.5 mg by weight of deoxycholic acid;
  d) about 219 mg by weight of mannitol and about 221 mg by weight of colloidal silicon dioxide.

Any of the disclosed compositions can be used to treat treatment resistant epilepsy in a subject.

Further disclosed herein is a method for treating Lennox-Gastaut syndrome in a patient suffering from Lennox-Gasstaut syndrome and in need of treatment, comprising administering to the patient in need of treatment a composition comprising:
  a) from about 5% to about 20% by weight of CBD oil containing from about 88% to about 92% by weight of cannabidiol;
  b) from about 15% to about 40% by weight of high oleic acid sunflower oil;
  c) from about 5% to about 15% by weight of one or more bile salts; and
  d) from about 35% to about 75% by weight of one or more carriers.

In a yet further aspect the for treating Lennox-Gastaut syndrome comprises administering to the patient in need of treatment a composition comprising:
  a) from about 30 mg to about 135 mg of CBD oil containing from about 88% to about 91% by weight of cannabidiol;
  b) from about 60 mg to about 270 mg by weight of high oleic acid sunflower oil;
  c) from about 25 mg to about 100 mg by weight of one or more bile salts wherein the salts contain from about 45% to about 55% by weight of cholic acid, deoxycholic acid, taurocholate, glycocholic acid, and mixtures thereof; and
  d) from 120 mg to about 500 mg by weight of one or more carriers.

In a still yet further aspect the method for treating Lennox-Gastaut syndrome comprises administering to the patient in need of treatment a composition comprising:
  a) from about 5 mg to about 32 mg by weight of CBD oil containing from about 88% to about 91% by weight of cannabidiol;
  b) from about 10 mg to about 65 mg by weight of one or more edible oils chosen from sunflower oil, coconut oil, canola oil, palm oil, soybean oil, corn oil, safflower oil, peanut oil, and mixtures thereof;
  c) from about 75 mg to about 300 mg by weight of bile salts containing from about 45% to about 55% by weight of cholic acid, deoxycholic acid, taurocholate; glycocholic acid, and mixtures thereof;
  d) from about 35 mg to about 150 mg by weight of sodium bicarbonate; and
  e) from about 110 mg to about 465 mg of a carrier.

A yet further method herein is a method for treating Aicardi syndrome in a patient suffering from Aicardi syndrome and in need of treatment, comprising administering to the patient in need of treatment a composition comprising:
  a) from about 5% to about 20% by weight of CBD oil containing from about 88% to about 92% by weight of cannabidiol;
  b) from about 15% to about 40% by weight of high oleic acid sunflower oil;
  c) from about 5% to about 15% by weight of one or more bile salts; and
  d) from about 35% to about 75% by weight of one or more carriers.

In a yet further aspect the method herein is a method for treating Aicardi syndrome the method comprises administering to the patient in need of treatment a composition comprising:
  a) from about 30 mg to about 135 mg of CBD oil containing from about 88% to about 91% by weight of cannabidiol;
  b) from about 60 mg to about 270 mg by weight of high oleic acid sunflower oil;
  c) from about 25 mg to about 100 mg by weight of one or more bile salts wherein the salts contain from about 45% to about 55% by weight of cholic acid, deoxycholic acid, taurocholate, glycocholic acid, and mixtures thereof; and
  d) from 120 mg to about 500 mg by weight of one or more carriers.

In another aspect the method for treating Aicardi syndrome comprises administering to the patient in need of treatment a composition comprising:

a) from about 5 mg to about 32 mg by weight of CBD oil containing from about 88% to about 91% by weight of cannabidiol;
b) from about 10 mg to about 65 mg by weight of one or more edible oils chosen from sunflower oil, coconut oil, canola oil, palm oil, soybean oil, corn oil, safflower oil, peanut oil, and mixtures thereof;
c) from about 75 mg to about 300 mg by weight of bile salts containing from about 45% to about 55% by weight of cholic acid, deoxycholic acid, taurocholate; glycocholic acid, and mixtures thereof;
d) from about 35 mg to about 150 mg by weight of sodium bicarbonate; and
e) from about 110 mg to about 465 mg of a carrier.

Any of the above disclosed compositions are suitable for the treatment of Dravet syndrome, Lennox-Gastaut syndrome, or Aicardi syndrome As with all diseases, there is a variability between children and adults. This difference can be based upon age, body weight, frequency of seizure, and the like. In addition, anti-seizure drugs (AED) can be added as a secondary active ingredient. Non-limiting examples of anti-seizure drugs include clobazam, levetiracetam, topiramate, stiripentol, phenobarbital, lacsamide, valproic acid, zonisamide, perampanel, and fosphenytoin.

The effective dose necessary to affect control of epilepsy in a patient is based upon the amount of cannabidiol delivered to the patient in need. This amount is determined by a medical practitioner after a period of patient observation. The present disclosure relates to a dosage of cannabidiol from about or greater than 5 mg/kg/day. Thus, for an 80 kg patient a dose of greater than or equal to 400 mg of CBD per day would be provided. Doses greater than 5 mg/kg/day such as greater than 10/mg/kg/day, greater than 15 mg/kg/day, greater than 20 mg/kg/day and greater than 25 mg/kg/day can also be effective for treating epilepsy.

In one non-limiting embodiment, after providing an original or first dose of about 2 mg/kg/day, the amount upon observation of the subject can be gradually increased. For example, from 2 mg/kg/day to 3 mg/kg/day, 2 mg/kg/day to 4 mg/kg/day, 2 mg/kg/day to 5 mg/kg/day, 5 mg/kg/day to 7.5 mg/kg/day, 5 mg/kg/day to 10 mg/kg/day until an effective dose in a subject is determined. In one iteration the amount of cannabidiol that can be given is 2.5 mg/kg/day, 2.6 mg/kg/day, 2.7 mg/kg/day, 2.8 mg/kg/day, 2.9 mg/kg/day, 3.0 mg/kg/day, 3.1 mg/kg/day, 3.2 mg/kg/day, 3.3 mg/kg/day, 3.4 mg/kg/day, 3.5 mg/kg/day, 3.6 mg/kg/day, 3.7 mg/kg/day, 3.8 mg/kg/day, 3.9 mg/kg/day, 4.0 mg/kg/day, 4.1 mg/kg/day, 4.2 mg/kg/day, 4.3 mg/kg/day, 4.4 mg/kg/day, 4.5 mg/kg/day, 4.6 mg/kg/day, 4.7 mg/kg/day, 4.8 mg/kg/day, or 4.9 mg/kg/day.

In a further iteration the amount of cannabinol dosage can be from about 5 mg/kg/day to about 25 mg/kg/day, for example, 5 mg/kg/day, 6 mg/kg/day, 7 mg/kg/day, 8 mg/kg/day, 9 mg/kg/day, 10 mg/kg/day, 11 mg/kg/day, 12 mg/kg/day, 13 mg/kg/day, 14 mg/kg/day, 15 mg/kg/day, 16 mg/kg/day, 17 mg/kg/day, 18 mg/kg/day, 19 mg/kg/day, 20 mg/kg/day, 21 mg/kg/day, 22 mg/kg/day, 23 mg/kg/day, 24 mg/kg/day, or 25 mg/kg/day.

Summary of the Disclosed Testing

Disclosed herein are test results comparing Epidiolex™ with the disclosed compositions. The tests include both human and animal testing.

The first disclosed test compares Epidiolex™ with a disclosed composition and control. The test utilized is the acute maximal electroshock (MES) model comparing the effectiveness of the present compositions versus Epidiolex™ in an epilepsy model.

Next a human clinical trial comparison between Epidiolex™ and a disclosed composition is described herein. These data were compared to the disclosed human clinical study in humans using a disclosed composition.

A literature comparison was made between a literature pharmacokinetic study and a disclosed study utilizing a composition of the present disclosure.

Comparison of Epidiolex™ with Disclosed Composition in Animal Studies

The disclosed compositions were tested against a control and Epidiolex™ in the following efficacy tests.

Study Design

The following studies were conducted to test and evaluate the therapeutic efficacy of the disclosed compositions for treating epilepsy in a subject suffering from or diagnosed with epilepsy. Epilepsy is characterized by recurrent seizures that can vary from brief and nearly undetectable periods to long periods of vigorous shaking due to abnormal electrical activity in the brain.

The acute maximal electroshock (MES) model was used in the disclosed animal testing to determine the efficacy of the disclosed compounds versus vehicle control and Epidiolex™ an FDA approved treatment for epilepsy. Two studies were conducted: a Pilot study to determine the effective dose of the disclosed compositions and a paired comparison test versus control and Epidiolex™ at the dosage determined in the pilot study.

The second study was used to determine the time of peak effect of the disclosed compositions at the effective dose determined in the pilot study. The primary endpoints of these studies included clinical observations, maximum seizure severity scoring and suppression of the tonic hind limb extension (HLE) following MES test.

In the pilot study, MES testing was performed 1.5 hours+ 30 mins post treatment with disclosed composition from Table 1, example 3, Epidiolex, or vehicle. Animals treated with 50 mg/kg Epidiolex or vehicle presented with full HLE following MES test indicating no protection at this timepoint. Treatment with 50 mg/kg of the disclosed composition in a single test subject resulted in partial HLE, characterized by partial or incomplete extension of one or both hind limbs. Treatment with 75 mg/kg of the disclosed composition revealed full protection (no HLE) in 66.6% of test subjects following MES test compared to 50% in the Epidiolex group and 0% in the vehicle treated group. At the 100 mg/kg dose level, Epidiolex exhibited the highest level of protection with 75% of animals presenting with no HLE compared to 33% in the disclosed composition group and 0% in the vehicle treated group. Based on these results, the effective dose of the disclosed composition was determined to be 75 mg/kg.

For the paired comparison study, MES testing was performed at five separate timepoints (15 min±5 min, 30 min±10 min, 1 hr±15 min, 2 hr±20 min, and 4 hr±30 min) following treatment with the disclosed composition, Epidiolex, or vehicle at the effective dose (75 mg/kg) determined in the pilot study. At the 15-minute timepoint, all animals from all groups presented with full HLE. Notably, administration of 75 mg/kg of the disclosed composition yielded partial HLE in 37.5% of animals and no HLE in 12.5% of test subjects at 30 minutes compared to 0% in the Epidiolex group and 0% in the vehicle group. At the one-hour timepoint, 75% of animals treated with the disclosed composition did not present with full HLE compared to 50% in the Epidiolex treated group and 0% in the vehicle treated group. At the 2-hour timepoint, treatment with the disclosed composition and Epidiolex were comparable with 50% of test subjects showing full protection and 12.5% with partial protection. At the 4-hour timepoint, Epidiolex exhibited the highest level of protection with 50% of animals presenting with no HLE compared 12.5% of test subjects in the disclosed composition group. It bears mentioning, however, that between the 30-minute and 4-hour timepoints respectively, animals in the vehicle treated group presented with partial (12.5-25%) or full protection (12.5%), but this is likely due to variability stemming from technical, biological (circadian or hormonally induced rhythms), and/or environmental factors. Based on these results, 1-hour was determined to be the time of peak effect for the disclosed composition, although the disclosed composition may potentially have a faster onset of effectiveness as shown by partial protection beginning at 30 minutes post dose.

After the quarantine period and prior to treatment initiation, male Sprague Dawley rats were randomly assigned to their respective treatment groups Table A for the pilot study and Table B for the paired comparison. On the day of study, following treatment with the composition disclosed in Table 4, Example 3, Epidiolex™, or vehicle, HLE was evoked at various timepoints by the MES test delivered by corneal electrodes. For the pilot study and the paired comparison study, the pretreatment times before MES test were based upon published literature of the biological activity of the positive control, Epidiolex (Patra et. al. 2018). Acute clinical signs and suppression of HLE were assessed immediately following MES test. All drugs were administered via oral gavage in mg/kg doses as outlined in Table I and Table II. For the pilot study n=21 and n=28 for the paired comparison study. The following Table 1 provides non-limiting examples of this aspect of the disclosed compositions.

Test Composition

The disclosed composition from Table 4, example 3, was formulated fresh each day of dosing in sterile water to achieve a concentration of 5 mg/mL accounting for potency. Upon reconstitution, the suspension was vortexed thoroughly, then placed in a water bath sonicator for 1 minute to achieve a homogenous formulation. The formulation was held on wet ice while in use and protected from light. Immediately prior to administration, the formulation was briefly mixed by vortexing and/or inversion to ensure homogeneity. The formulation was used within 12 hours and discard at the completion of dosing.

TABLE 4

| Ingredients (mg) | 1 | 2 | 3[1] | 4 | 5 |
|---|---|---|---|---|---|
| CBD oil | 27.6 | 32.8 | 30.5 | 29.5 | 30 |
| High oleic acid sunflower oil | 55.2 | 65.6 | 61.1 | 59 | 60 |
| Gum Arabic | 455.4 | 458.4 | 458.4 | 461.5 | 460 |
| Bile salts | 305.4 | 294.6 | 300 | 300 | 300 |
| NaHCO$_3$ | 156.6 | 148.6 | 150 | 150 | 150 |
| Total | 1000 | 1000 | 1000 | 1000 | 1000 |

[1]CBD Oil contains 89.6% cannabidiol for an effective amount of 27.4 mg.

The composition disclosed in Example 3 of Table 4 was used in the rodent MES epilepsy study disclosed herein below.

Vehicle

The vehicle formulation was devoid of any CBD content and was formulated fresh each day of dosing in sterile water in achieve a 5 mg/mL concentration. Upon reconstitution, the suspension was vortexed thoroughly, then placed in a water bath sonicator for 1 minute to achieve a homogenous formulation. The formulation was held on wet ice while in use and protected from light. Immediately prior to administration, the formulation was briefly mixed by vortexing and/or inversion to ensure homogeneity. The formulation was used within 12 hours and discard at the completion of dosing.

Prescription grade Epidiolex™ was used in the disclosed MES study. Each milliliter of this material contains 100 mg of cannabidiol, 79 mg of anhydrous ethanol, 736 mg of refined sesame oil, sucralose and strawberry flavoring. Epidiolex™ was provided ready to use with CBD content of 100 mg/mL and was used within one month of opening (stored at ambient temperature).

MES Test

Pilot Efficacy Study Design

TABLE A

| Group | Test Article | Dose[1] | Dosing Route/ frequency of TA | Seizure induction | # Animals | Additional Endpoints |
|---|---|---|---|---|---|---|
| 1 | vehicle | N/A | PO/single | MES | 7 | MSS |
| 2 | Composition Table 1, example 3 | Up to 100 mg/kg | PO/single | MES | 7 | |
| 3 | Epidiolex | Up to 100 mg/kg | PO/single | MES | 7 | |

1. Dosing began at 50 mg/kg and increased in 25 mg/kg increments up to 100 mg/kg until an effective dose is determined.
2. PO=oral gavage.
3. MES=maximum electroshock. MES was performed 1.5 hours #30 mins after oral administration of test article.
4. MSS=maximal seizure severity.

TABLE B

| Group | Test Article | Dose[1] | Dosing Route/ frequency of TA | Seizure induction | # Animals | Additional Endpoints |
|---|---|---|---|---|---|---|
| 1 | vehicle | N/A | PO/single | MES | 8 | Clinical observations and MSS |
| 2 | Composition Table 1, example 3 | 75 mg/kg | PO/single | MES | 8 | |
| 3 | Epidiolex | 75 mg/kg | PO/single | MES | 8 | |

1. Effective dose determined in Pilot study.
2. PO=oral gavage.
3. MES=was conducted at 5 timepoints (25 mins±5 mins, 30 mins±10 mins, 1 hr±15 mins, 2 hr±20 mins, and 4 hr±30 mins) post oral administration of test article.
4. MSS=maximal seizure severity.

The following terms in Tables I-VIII are used to describe the results of the experiments in the data disclosed herein below.

TABLE I

| Term | Definition |
|---|---|
| HLE | Hind limb extension |
| Stage 1 | myoclonic jerks with sudden and repetitive movement of the head and neck with or without stiffening of the tail |
| Stage 2 | atypical (unilateral or incomplete) clonic seizure |
| Stage 3 | clonic seizure with bilateral forelimb clonus and rearing |
| Stage 4 | tonic-clonic seizure with an initial wild run and subsequent loss of righting reflex |
| Stage 5 | tonic-clonic seizure with full extension of fore- and hind-limbs |

Results of the Pilot Study

TABLE II

VEHICLE CONTROL

| Animal No. | Dose (mg/kg) | MES-baseline | MES post-dose |
|---|---|---|---|
| 1001 | 50 | HLE | HLE with stage 2 seizure severity |
| 1002 | 75 | HLE | HLE with stage 2 seizure severity |
| 1003 | 100 | HLE with stage 2 seizure severity | Partial HLE with stage 3 seizure severity |
| 1004 | 100 | HLE with stage 3 seizure severity | HLE with stage 3 seizure severity |
| 1005 | 75 | HLE with stage 2 seizure severity | HLE with stage 3 seizure severity |
| 1006 | 100 | HLE with stage 2 seizure severity | HLE with stage 2 seizure severity |
| 1007 | 100 | HLE with stage 3 seizure severity | HLE with stage 3 seizure severity |

TABLE III

DISCLOSED COMPOSITION*

| Animal No. | Dose (mg/kg) | MES-baseline | MES post-dose |
|---|---|---|---|
| 2001 | 50 | HLE slow recovery | Partial HLE with stage 2 seizure severity |
| 2002 | 75 | HLE with stage 4 seizure severity | No HLE with stage 3 seizure severity |
| 2003 | 75 | Partial HLE with stage 3 seizure severity | No HLE or seizure activity observed. Some splaying of the left hindlimb |
| 2004 | 100 | Partial HLE with stage 2 seizure severity | No HLE, stage 2 seizure severity (quick recovery) |
| 2005 | 75 | HLE with stage 2 seizure severity. tail stiffening | HLE with stage 2 seizure severity (quick recovery) |
| 2006 | 100 | HLE with stage 2 seizure severity | HLE with stage 3 seizure severity |
| 2007 | 100 | HLE with stage 3 seizure severity | HLE with stage 2 seizure severity that progressed to stage 4 (prolonged tonic seizure lasting approximately 12 mins) |

*Composition from Table 1, Example 3

TABLE IV

EPIDIOLEX ™

| Animal No. | Dose (mg/kg) | MES-baseline | MES post-dose |
|---|---|---|---|
| 3001 | 50 | Partial HLE with stage 2 seizure severity | No HLE with stage 3 seizure severity |
| 3002 | 75 | HLE with stage 2 seizure severity | Partial HLE with stage 2 seizure severity |
| 3003 | 75 | HLE with stage 3 seizure severity | HLE with stage 2 seizure severity |
| 3004 | 100 | HLE with stage 3 seizure severity. Wild run observed after stimulation | Partial HLE with stage 3 seizure severity, quick recovery |
| 3005 | 75 | Partial HLE with stage 3-4 seizure severity (running/bouncing seizures) | No HLE, reactive to stimulation (briefly remained in state of shock) |
| 3006 | 100 | Partial HLE with stage 3 seizure severity | No HLE with stage 2 seizure severity |
| 3007 | 100 | HLE with stage 2 seizure severity, left ear bending/stiffening | No HLE with stage 3 seizure severity |

The pilots study determined that the amount of the disclosed composition that would be used for the paired comparison Main Study was 75 mg/kg.

Results of Paired Comparison Main Study (Time of Peak Efficiency)

TABLE V

VEHICLE CONTROL

| Animal No. | Animal mass (g) | Time | MES Results |
|---|---|---|---|
| 1008 | 158.1 | 15 min. | HLE, tonic state ~40 sec |
| | | 30 min. | Partial HLE, stage 3 seizure, tonic state ~30 sec |
| | | 1 hour | HLE, stage 3, tonic state, ~40 sec |
| | | 2 hours | HLE, stage 3, tonic state ~30 sec, tail stiffening |
| | | 4 hours | HLE, stage 3, tail stiffening, tonic state ~30 sec |
| 1009 | 163.1 | 15 min. | HLE, stage 3, tonic state ~60 sec |
| | | 30 min. | HLE, stage 3, twitching with rearing, tonic state ~40 sec |
| | | 1 hour | HLE, stage 2, tonic state ~30 sec |
| | | 2 hours | HLE, stage 2, tonic state ~20 sec |
| | | 4 hours | HLE, stage 2, tonic state ~35 sec |
| 1010 | 219.4 | 15 min. | HLE, stage 3, tail stiffening, tonic state ~80 sec |
| | | 30 min. | Partial HLE, stage 3, twitching with rearing, tonic state ~30 sec |
| | | 1 hour | HLE, stage 3, tail stiffening, tonic state ~40 sec |
| | | 2 hours | HLE, stage 3, tail stiffening, tonic state ~30 sec |
| | | 4 hours | HLE, stage 3, tail stiffening, tonic state ~40 sec |
| 1011 | 179.4 | 15 min. | HLE, stage 3, tail stiffening, tonic state ~40 sec |
| | | 30 min. | HLE, stage 3, tail stiffening, tonic state ~30 sec |
| | | 1 hour | HLE, stage 2, tonic state ~25 sec |
| | | 2 hours | HLE, stage 2, tail stiffening, tonic state ~30 sec |
| | | 4 hours | HLE, stage 3, tonic state ~10 sec |
| 1012 | 250.6 | 15 min. | HLE, stage 3, tail stiffening, tonic state ~30 sec |
| | | 30 min. | HLE, stage 3, shaking/twitching body, tonic state ~40 sec |
| | | 1 hour | HLE, stage 2, tail stiffening, tonic state ~30 sec |

TABLE V-continued

VEHICLE CONTROL

| Animal No. | Animal mass (g) | Time | MES Results |
|---|---|---|---|
| | | 2 hours | No HLE, no seizure activity, tonic state ~10 sec |
| | | 4 hours | Partial HLE, stage 2, tonic state ~30 sec |
| 1013 | 247.7 | 15 min. | HLE, stage 3 seizure, tonic state ~30 sec |
| | | 30 min. | HLE, stage 3 seizure, tonic state ~20 sec |
| | | 1 hour | HLE, stage 1 seizure, tonic state ~20 sec |
| | | 2 hours | HLE, stage 3, tail stiffening, tonic state ~40 sec |
| | | 4 hours | Partial HLE, stage 1, tail stiffening, tonic state ~40 sec |
| 1014 | 218.7 | 15 min. | HLE, stage 3, tail stiffening, tonic state ~30 sec |
| | | 30 min. | HLE, stage 3, tail stiffening, tonic state ~45 sec |
| | | 1 hour | HLE, stage 1/5 (forelimb extension), tonic state ~30 sec |
| | | 2 hours | HLE, stage 3, tonic state ~30 sec |
| | | 4 hours | HLE, stage 2, tail stiffening, tonic state ~40 sec |
| 1015 | 242.8 | 15 min. | HLE, stage 3, tail stiffening, tonic state ~30 sec |
| | | 30 min. | HLE, stage 2, tail stiffening, tonic state ~40 sec |
| | | 1 hour | Partial HLE, stage 2, tonic state ~25 sec |
| | | 2 hours | HLE, stage 3, tonic state ~30 sec |
| | | 4 hours | HLE, stage 1, tonic state ~30 sec |

TABLE VII

DISCLOSED COMPOSITION*

| Animal No. | Animal mass (g) | Time | MES Results |
|---|---|---|---|
| 2008 | 230.2 | 15 min. | HLE, stage 2, tonic state ~30 sec |
| | | 30 min. | Partial HLE, stage 3, tonic state ~20 sec |
| | | 1 hour | No HLE, no seizure, tonic state ~15 sec |
| | | 2 hours | Partial HLE, stage 2, tonic state ~40 sec |
| | | 4 hours | HLE, stage 2, tail stiffening, tonic state ~30 sec |
| 2009 | 174.1 | 15 min. | HLE, stage 3-5, tonic state ~30 sec |
| | | 30 min. | Partial HLE, stage 3, tonic state ~30 sec |
| | | 1 hour | No HLE, no seizure, tonic state ~40 sec |
| | | 2 hours | HLE, stage 2, tail stiffening |
| | | 4 hours | HLE, stage 2, tonic state ~40 sec |
| 2010 | 221.2 | 15 min. | HLE stage 3, tonic state ~45 sec |
| | | 30 min. | HLE, stage 3, tail stiffening, tonic state ~25 sec |
| | | 1 hour | No HLE, quick recovery, no seizure activity |
| | | 2 hours | No HLE, no seizure, tonic state ~10 sec |
| | | 4 hours | HLE, stage 2, tonic state ~20 sec |
| 2011 | 199.7 | 15 min. | HLE, stage 1-2, tail stiffening, tonic seizure ~30 sec |
| | | 30 min. | HLE, stage 2, tail stiffening, body shaking/twitching, tonic state ~35 sec |
| | | 1 hour | No HLE, no seizure, tonic state ~15 sec |
| | | 2 hours | HLE, stage 2, tail stiffening, tonic state ~30 sec |
| | | 4 hours | HLE, stage 1-2, tonic state ~30 sec |
| 2012 | 180.3 | 15 min. | HLE, stage 5, tonic state ~30 sec. |
| | | 30 min. | HLE, stage 3, tonic state ~25 sec |
| | | 1 hour | HLE, stage 3, shaking/twitching body, tonic state ~35 sec |
| | | 2 hours | HLE, stage 1-2, tail stiffening, tonic seizure ~30 sec |
| | | 4 hours | HLE, stage 2, tail stiffening, tonic state ~30 sec |
| 2013 | 244.1 | 15 min. | HLE, stage 2, tail stiffening, tonic state ~30 sec |
| | | 30 min. | HLE, no seizure activity, tonic state ~20 sec |

TABLE VII-continued

DISCLOSED COMPOSITION*

| Animal No. | Animal mass (g) | Time | MES Results |
|---|---|---|---|
| | | 1 hour | Partial HLE, stage 3, tail stiffening, tonic state ~40 sec |
| | | 2 hours | No HLE, no seizure activity, tonic state ~35 sec |
| | | 4 hours | HLE, stage 2, tail stiffening, tonic state ~30 sec |
| 2014 | 237.2 | 15 min. | HLE, stage 2, tonic state ~30 sec |
| | | 30 min. | No HLE, stage 2, tonic state ~30 sec |
| | | 1 hour | No HLE, no seizure activity, shaking/twitching body, tonic state ~15 sec |
| | | 2 hours | No HLE, no seizure activity, tonic state ~15 sec |
| | | 4 hours | No HLE, no seizure activity, tonic state ~10 sec |
| 2015 | 181.6 | 15 min. | HLE, stage 3, tail stiffening, tonic state ~30 sec |
| | | 30 min. | Partial HLE, stage 3, tail stiffening, tonic state ~50 sec |
| | | 1 hour | No HLE, stage 3, tonic state ~30 sec |
| | | 2 hours | No HLE, stage 3, tonic state ~40 sec |
| | | 4 hours | HLE, stage 3, tail stiffening, tonic state ~35 sec |

*Composition from Table 1, Example 3

TABLE VIII

EPIDIOLEX ™ COMPOSITION

| Animal No. | Animal mass (g) | Time | MES Results |
|---|---|---|---|
| 3008 | 220.9 | 15 min. | HLE, stage 3, tonic seizure ~40 sec, stiff head/arms |
| | | 30 min. | HLE, stage 2, tail stiffening, tonic state ~40 sec |
| | | 1 hour | No HLE, no seizure activity |
| | | 2 hours | Partial HLE, stage 3, tonic state ~30 sec |
| | | 4 hours | No HLE, no seizure activity, tonic state ~10 sec |
| 3009 | 225.8 | 15 min. | HLE, stage 3, tonic state ~30 sec |
| | | 30 min. | HLE stage 3, tonic state ~30 sec |
| | | 1 hour | No HLE, stage 2-3, quick recovery |
| | | 2 hours | No HLE, tonic state ~20 sec |
| | | 4 hours | No HLE, tonic state ~15 sec |
| 3010 | 236.8 | 15 min. | HLE, stage 4, running bouncing seizures, tonic state 2.5 mins |
| | | 30 min. | HLE, stage 3, twitching with rearing, tonic state ~30 sec |
| | | 1 hour | Partial HLE, tonic state ~45 sec |
| | | 2 hours | No HLE, twitching with rearing, tonic state ~20 sec |
| | | 4 hours | HLE, stage 3, tonic state ~40 sec |
| 3011 | 179.2 | 15 min. | HLE, stage 3, tail stiffening, tonic state ~45 sec |
| | | 30 min. | HLE, stage 5, tonic state ~45 sec |
| | | 1 hour | HLE, stage 5, tonic state ~30 sec |
| | | 2 hours | HLE, stage 3, tonic state ~35 sec |
| | | 4 hours | HLE, stage 3, tonic state ~35 sec |
| 3012 | 220.7 | 15 min. | HLE, stage 2, tail stiffening, tonic state ~50 sec |
| | | 30 min. | HLE, stage 2-3, twitching with rearing, tonic state ~40 sec |
| | | 1 hour | HLE, stage 2, tail stiffening, tonic state ~30 sec |
| | | 2 hours | HLE, stage 3, tonic state ~35 sec |
| | | 4 hours | HLE, stage 3, tail stiffening, tonic state ~40 sec |
| 3013 | 229.2 | 15 min. | HLE, stage 3, tail stiffening, tonic state ~30 sec |
| | | 30 min. | HLE, stage 3, tonic state ~30 sec |
| | | 1 hour | No HLE, no seizure activity, tonic state ~10 sec |

TABLE VIII-continued

EPIDIOLEX ™ COMPOSITION

| Animal No. | Animal mass (g) | Time | MES Results |
|---|---|---|---|
|  |  | 2 hours | No HLE, no seizure activity, tonic state ~10 sec |
|  |  | 4 hours | No HLE, no seizure activity, tonic state ~5 sec |
| 3014 | 200.0 | 15 min. | HLE, stage 2, tail stiffening, tonic state ~50 sec |
|  |  | 30 min. | HLE, stage 3, tonic state ~45 sec |
|  |  | 1 hour | No HLE, no seizure activity, tonic state ~50 sec |
|  |  | 2 hours | No HLE, no seizure activity, tonic state ~45 sec |
|  |  | 4 hours | No HLE, no seizure activity, tonic state ~30 sec |
| 3015 | 202.0 | 15 min. | HLE, stage 2, tail stiffening, tonic state ~40 sec |
|  |  | 30 min. | HLE, stage 2, tonic state ~30 sec |
|  |  | 1 hour | HLE, stage 3, tonic state ~30 sec |
|  |  | 2 hours | HLE, stage 2, tonic state ~30 sec |
|  |  | 4 hours | HLE, stage 2-3, tonic state ~30 sec |

Summary

The disclosed composition enhanced effectiveness, based on the rapidity of action. At the 30-minute timepoint, 50% of the animals dosed with the disclosed composition showed partial reduction or full elimination of seizure activity whereas 100% of the Epidiolex™-dosed animals exhibited full seizure activity at 30 minutes. At the 60-minute timepoint 87.5% of the animals dosed with the disclosed composition showed partial reduction or full elimination of seizure activity compared to 62.5% of the Epidiolex™-dosed animals showing partial reduction or full elimination of seizure activity. Epidiolex™ showed some enhanced seizure reduction capabilities at later time points in the study.

Pharmacokinetic Studies

Studies Comparing Epidiolex™ with the Disclosed Compositions in Humans

Disclosed Composition Pharmacokinetic Studies

Pharmacokinetic studies were conducted in humans to test the amount of cannabidiol present in plasma levels at various doses. The disclosed composition from was dosed in the patients that enrolled in the study at a dose of 3.28 mg/kg/day achieving a pre-dose plasma level of 33.3 ng/mL after the first 2.5 weeks (i.e., Period 1), then increased to a dose of 4.46 mg/kg/day achieving a pre-dose plasma level of 53.7 ng/ml after the last 2.5 weeks of the study (i.e., Period 2).

The results of this pharmacokinetic study in humans are summarized in Table 5 below.

TABLE 5

| Dosage (mg) | No. of patients | Period 1 mg/kg/day | Period 2 mg/kg/day | Mean level mg/kg/day |
|---|---|---|---|---|
| 225-375 | 9 | 3.33 | 5.56 | 4.45 |
| 300-375 | 41 | 3.46 | 4.32 | 3.89 |
| 300-450 | 16 | 2.8 | 4.2 | 3.5 |
| weighted mean | 66 | 3.28 | 4.46 | 3.87 |
| mean pCBD ng/ml | — | 33.3 | 53.7 | — |

Pharmacokinetic Study Using Disclosed Composition

The present disclosed composition pharmacokinetic studies were designed as a triple blind (Participant, Investigator, Outcomes Assessor), placebo-controlled, crossover pilot study in which 70 volunteers (aged 40-70 years) received either the composition disclosed in Table 1, No. 3 or a placebo in a cross-over manner. The study protocol was registered at the ClinicalTrials.gov (accessed on 7 Apr. 2022) (NCT05346562). The sequence of conditions the participant received was generated by a research randomizer web-service and participants completed: (1) placebo-control and (2) Composition from Table 1, No. 3 (225 to 300 mg split over three times daily for the initial 2.5 weeks equating to 3.28 mg/Kg/day, and 375 to 450 mg split over three times for the following 2.5 weeks equating to 4.46 mg/Kg/day). Following a two-week washout, participants then repeated testing for another five weeks under different conditions. Participants visited the laboratory on 6 occasions in total (3 in each study arm), each time following an overnight fast. The complete course of the study was performed at the Department for Integrative Physiology, University of Split School of Medicine, Split, Croatia. The study design, implementation, and reporting followed the CONSORT guidelines, including the 25-item checklist and a flow diagram. The study was conducted according to the guidelines of the Declaration of Helsinki and was approved by the Ethics Committee of University of Split School of Medicine on 15 Dec. 2021 (Class: 003-08/21-03/0003; Reg. No.: 2181-198-03-04-21-0091). Prior to enrollment in the study, every participant was informed about the procedures, course, and purpose of the research and each of them individually signed an informed written consent.

Each patient visited the laboratory 6 times in total. During each visit, a sample of venous blood was taken from forearm following an overnight fast and sample of urine was obtained. All blood and urine samples were analyzed in the same certified institutional biochemical laboratory, using the standard operating procedures.

Each subject conducted a diary to confirm the timing of CBD and placebo daily dose administration. In addition, during each visit, physical activity and food intake diaries (24 h) were provided for each subject. The participants were instructed to follow the same patterns of food intake and physical activity during all visits. If a participant missed a dose, a maximum of one capsule (75 mg) was added to the next dose. The adherence to intervention was considered satisfactory if >90% of therapy was taken, based on the remaining capsule count and patient's self-reported dosing diary.

Finally, the safety and tolerability profile of the composition from Table 1, No. 3 formulation during 5-week administration was determined via circulating (steady-state) plasma and urinary concentrations of CBD, and adverse event reporting. Hepatic (ALT, AST, ALP, GGT, and total bilirubin) markers were also measured.

Summary of Adverse Events

During the course of the intervention arm of trial (Dose Period 1 and 2), eight participants in total experienced adverse effects (AEs). In the placebo trial, there were six reports of an AE. Based on MedDRA (Version 25.1) and CTCAE V.5.0 terminology, all reported AEs were classified as Grade 1 (mild, intervention not indicated) and were distributed over the first and second dosing periods. No serious AEs were reported, and no participant has discontinued treatment as a result of AEs. AEs reported/observed during dose periods are listed in Table 6 below.

TABLE 6

Incidence of Adverse Effects, n (%)

| Symptom | Disclosed Composition | Placebo |
|---|---|---|
| Diarrhea | 3 (4.3%) | — |
| Bloating | 2 (2.9%) | 2 (2.9%) |
| Headache | 1 (1.4%) | 2 (2.9%) |
| Nausea | 1 (1.4%) | — |
| Vomiting | — | — |
| Hypersomnia | 1 (1.4%) | 1 (1.4%) |
| Constipation | — | 1 (1.4%) |

Liver Enzymes

Figure 3:
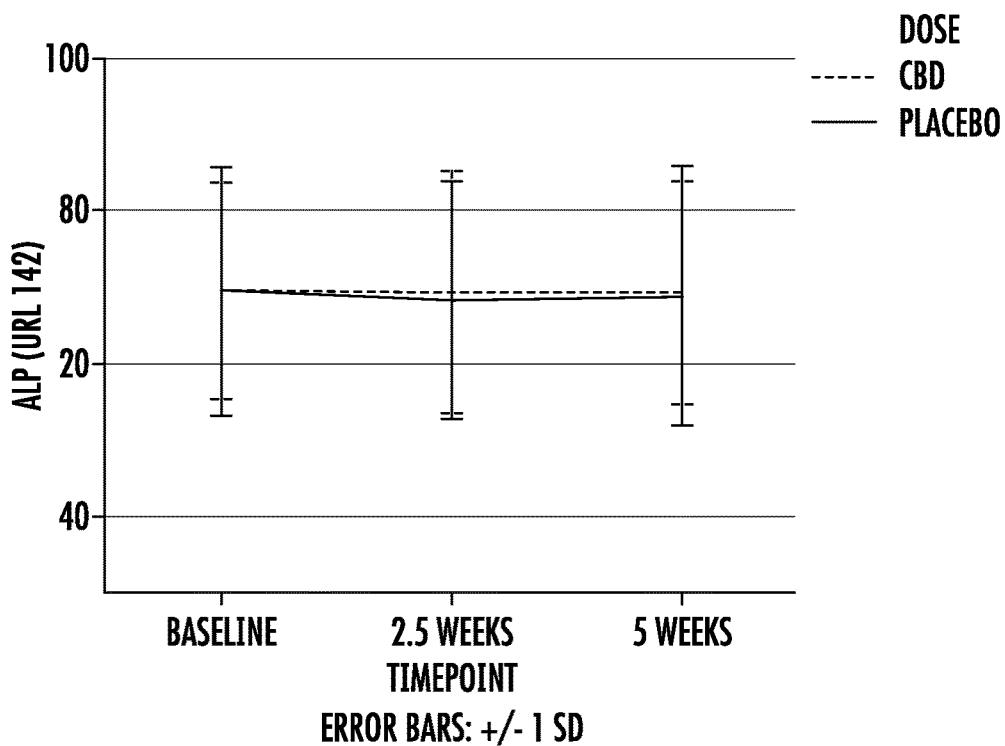
FIG. 3 shows the plasma alkaline phosphatase concentrations for CBD and placebo.
Figure 4:
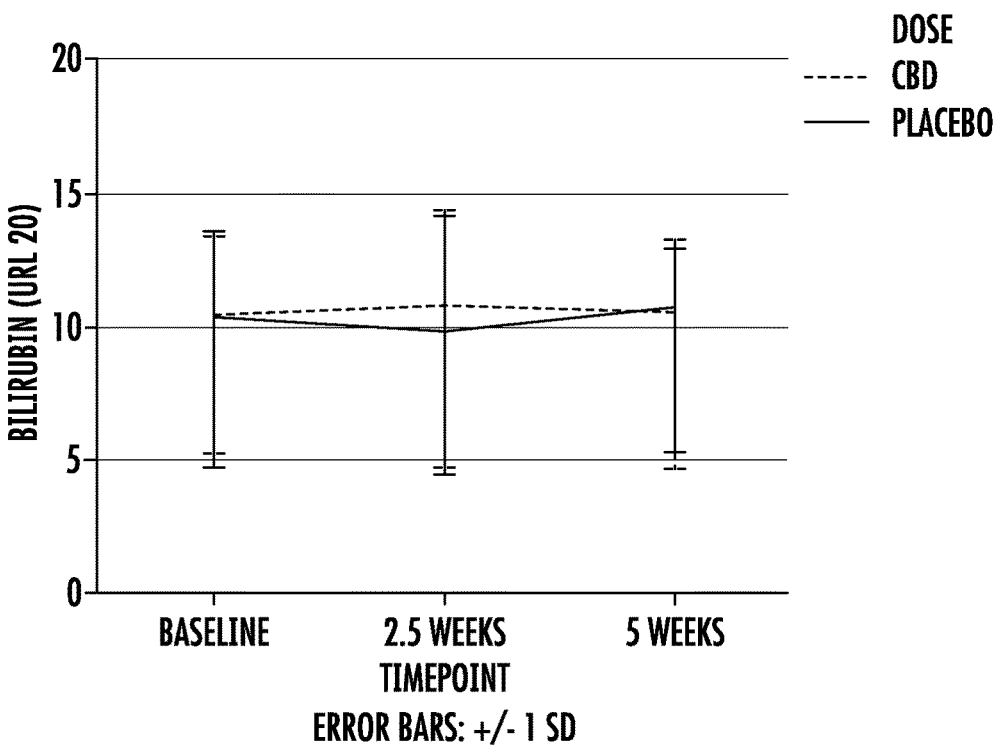
FIG. 4 indicates that the plasma alkaline phosphatase remained effectively unchanged over time.
Figure 5:
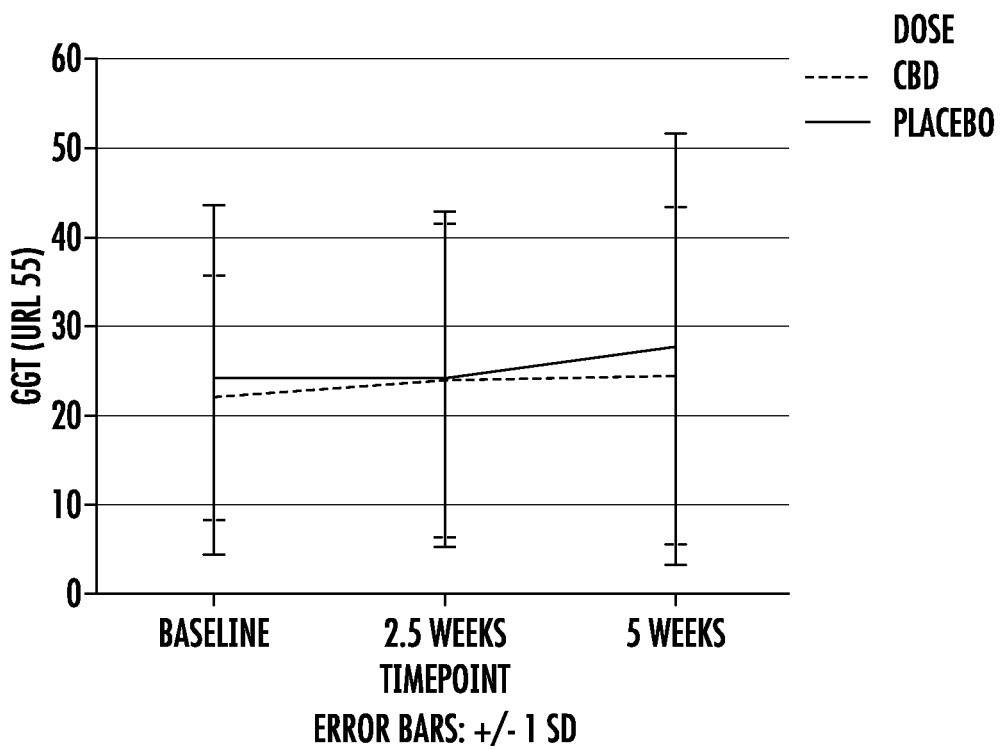
FIG. 5 shows the plasma gamma-glutamyl transferase concentrations for CBD and placebo.

The effect of the Composition from Table 3 dosing upon hepatic enzymes was also assessed. Administration of the composition from Table 2 formulation for 5 weeks did not result in changes in alanine transferase (ALT) (FIG. 1), alkaline phosphatase (ALP) (FIG. 2), or total bilirubin (FIG. 3). Gamma-glutamyl transferase (GGT) (main effect of dose: P=0.038; FIG. 4) was slightly higher during CBD compared to placebo, though there were no interaction effects. In contrast, aspartate transaminase (AST) was higher in the placebo condition (main effect of dose: P=0.047; FIG. 5), again with no interaction effects. Moreover, these changes we<1 standard deviation and therefore viewed as not clinically meaningful. As noted earlier, >3SD over normative values were classified as an AE.

Figure 2:
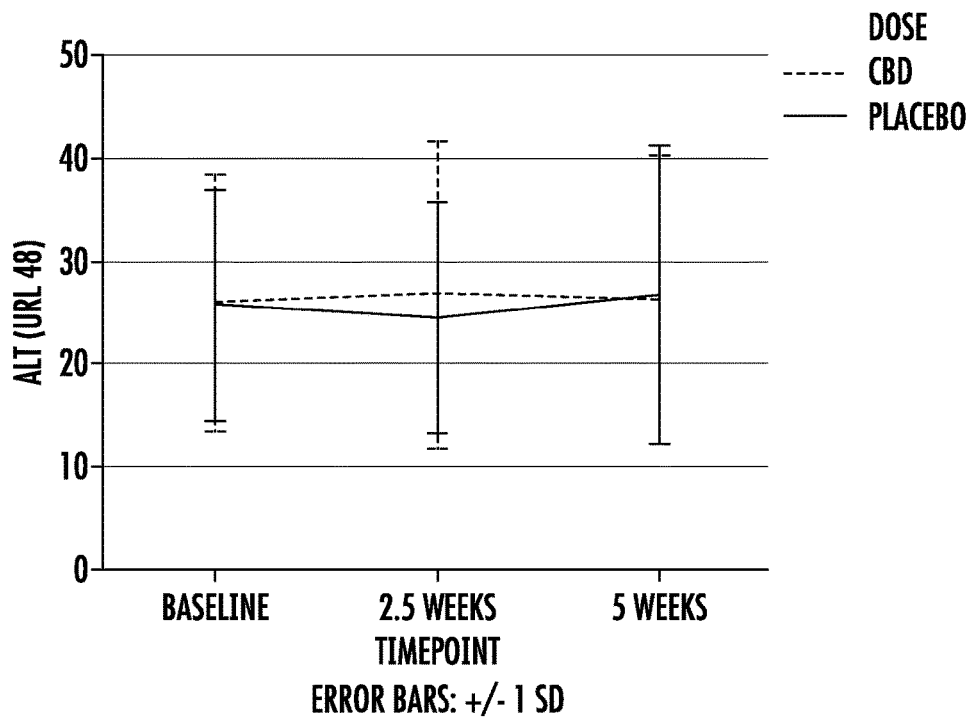
FIG. 2 shows the plasma alanine transaminase concentrations for CBD and placebo.
Figure 6:
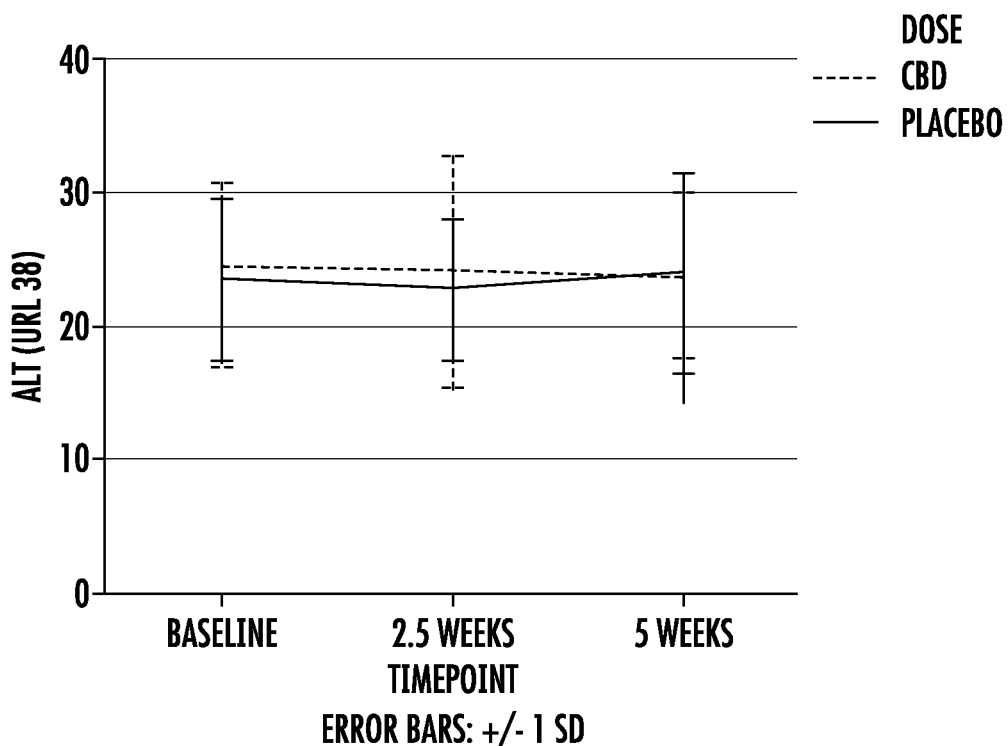
FIG. 6 shows the plasma aspartate transaminase concentrations for CBD and placebo.

FIG. 2 shows the plasma alanine transaminase concentrations for CBD and placebo. FIG. 2 indicates that the plasma alanine transaminase concentration remained effectively unchanged over time. FIG. 3 shows the plasma alkaline phosphatase concentrations for CBD and placebo. FIG. 4 indicates that the plasma alkaline phosphatase remained effectively unchanged over time. FIG. 4 shows the plasma total bilirubin concentrations for CBD and placebo. FIG. 4 indicates that the plasma total bilirubin concentration remained effectively unchanged over time. FIG. 5 shows the plasma gamma-glutamyl transferase concentrations for CBD and placebo. FIG. 5 indicates that the plasma gamma-glutamyl transferase concentration remained effectively unchanged over time. FIG. 6 shows the plasma aspartate transaminase concentrations for CBD and placebo. FIG. 6 indicates that the plasma aspartate transaminase concentration remained effectively unchanged over time.

Prior Art Testing

The above results are compared to a cannabidiol composition, for example, Epidiolex which does not comprise the adjunct ingredients found in Applicant's disclose pharmaceutical and non-pharmaceutical compositions. The following prior art disclosure and results were compared to the human test results as it relates to the plasma concentrations of each sample.

Devinsky (Devinsky, O et al., "Randomized, dose-ranging safety trial of cannabidiol in Dravet syndrome," Neurology 2018, 90; e1204-e1211)) conducted testing to "evaluate the safety and preliminary pharmacokinetic of a pharmaceutical formulation of purified cannabidiol (CBD) in children with Dravet syndrome.

Methodology

Patients aged 4-10 years were randomized 4:1 to CBD (5, 10, or 20 mg/kg/d) or placebo taken twice daily. The double-blind trial comprised 4-week baseline, 3-week treatment (including titration), 10-day taper, and 4-week follow-up periods.#

Results

A total of 34 patients were randomized: 30 patients at 8 sites in the United States and 4 patients at 3 sites in the United Kingdom; 32 patients (94%) completed the treatment period, and of these, 24 (75%) entered an open-label extension trial. Two patients on CBD were withdrawn during the treatment period. All 34 randomized patients were included in the safety analysis set: 10, 8, and 9 patients in the 5, 10, and 20 mg/kg/d CBD groups, respectively, and 7 patients in the placebo group The results are summarized herein below in Table 15.

TABLE 7

| | Cannabidiol dose | | |
|---|---|---|---|
| | 5 mg/kg/day (N = 10) | 10 mg/kg/day (N = 8) | 20 mg/kg/day (N = 9) |
| Parameter time | | Mean (SD) | |
| Plasma concentration on Day 1 at starting CBD dose: ng/ml | | | |
| Pre-dose | 0 | 0 | 0 |
| 2.5 hours | 37.6 (53.7) | 34.4 (32.1) | 29.3 (28.5) |
| 5 hours | 10.0 (5.74) | 11.3 (11.7) | 25.3 (42.4) |
| Plasma concentration on Day 22 at target CBD dose: ng/mL | | | |
| Pre-dose | 23.0 (11.5) | 62.1 (44.7) | 121 (81.3 |
| 2.5 hours | 130 (170) | 242 (159) | 380 (370) |
| 5 hours | 72.1 (49.0) | 288 (345) | 308 (321) |

FIG. 1 compares the results of the cannabidiol pre-dose steady state pharmacokinetic testing performed by Devinsky (sec, Devinsky, O et al., "Randomized, dose-ranging safety trial of cannabidiol in Dravet syndrome," Neurology 2018, 90; e1204-e1211) using a cannabidiol oral solution (GW Pharmaceuticals Ltd.) versus the pre-dose steady state pharmacokinetic testing of a composition disclosed herein in humans at two dose levels examined. The solid black line beginning at Point A connects the blood plasma levels at the two steady state dose levels examined in the present test (i.e., 3.28 mg/kg/day and 4.46 mg/kg/day respectively). The black dotted line extrapolates the results of the present data to the Devinsky point at approximately 5 mg/kg/day showing a blood plasma level greater than 60 ng/ml (Point B) vs about 23 ng/ml (Point D) achieved by Devinsky, evidencing the ability of the disclosed composition to outperform that of Devinsky pharmacokinetically. The plots continue linearly through to comparison of the present data extrapolated prospectively to 10 mg/kg/day versus Devinsky at that same level.

The safety and tolerability profile of Epidiolex™ has also been extensively reviewed (see, Center For Drug Evaluation and Research; Application No. 210365ORIG1S000; "A Combined Clinical and Statistical Review by Natalie Getzoff, MD and Xiang Ling, PhD NDA 210365". Epidiolex™ is approved for up to 25 mg/kg/day given as a divided dose. In controlled trials for Epidiolex™, hepatic (primarily liver enzyme elevations), gastrointestinal (primarily diarrhea), and central nervous system (primarily somnolence and lethargy) side effects were the main adverse events reported. Table 8 below provides a summary of the key safety findings reported for Epidiolex™ per the references provided above.

TABLE 8

| Finding | 5 mg/kg Dose | 10 mg/kg Dose | 20 mg/kg Dose |
|---|---|---|---|
| Laboratory evaluations- elevated transaminases, bilirubin, and alkaline phosphatase | Too few to evaluate | For the 10 and 20 mg/kg/d doses, however, there is an apparent dose-response; nearly all subjects with ALT elevations had received 20 mg/kg/d. Subjects typically received multiple AEDs during controlled studies, and 45% also received valproate, a known hepatotoxin. For subjects taking CBD, concomitant use of valproate increased the likelihood of ALT elevations by a factor of ~7. | |
| Hepatic AEs | Too few to evaluate [a] | 8% | 16% |
| CNS AEs [b] | Somnolence and lethargy were the most frequent of the CNS AEs, reported as SAEs in 2% vs. 0% of subjects in the CBD and placebo groups, respectively. There was an apparent dose-response, but the risk was appreciable even at the 10 mg/kg/d dose. For other CNS AEs, the frequencies were similar at the 10 and 20 mg/kg/d doses in the controlled trials. Based on results of the C-SSRS, no treatment-emergent suicidal ideation or behavior was found in subjects who received CBD during the trials. | | |
| Decreased appetite | Decreased appetite (21% vs. 5%) and weight decreased (4% vs. 1%) in the CBD and placebo groups, respectively, with a dose-response for both (greater frequencies in the 20 mg/kg group than the 10 mg/kg group). | | |
| Weight decreased [c] | 0 (0%) | 7 (9.3%) | 44 (18.5%) |
| GI AEs (non-hepatic) | GI AEs with small differences between the CBD and placebo groups include abdominal pain/distension/ discomfort and gastroenteritis (both 3% vs. 1%, respectively), as well as dry mouth (2% vs. 1%, respectively). | | |
| Diarrhea | Not reported in the SBA | 9% [d] | 20% |
| Renal AEs | Data show a rapid increase in serum creatinine with initiation of treatment, with a return to baseline values after discontinuation. One small study showed return to baseline with continued treatment, but longer experience in controlled trials showed sustained increase at end of treatment. | | |
| ECG | No significant mean effects on the mean QTcB (corrected QT; Bazett's formula), PR, or QRS intervals. | | |
| Anemia | 24% of CBD-treated subjects developed a new laboratory-defined anemia during the course of the study, vs 11% of subjects who received placebo. Anemia was reported only twice as an AE (1 in CBD; 1 in placebo), however, and severity was mild. Thus, it is not known if anemia is drug-related, but the significance was deemed to be small. | | |
| Other hematological | There were no other notable changes in hematological parameters (total leukocytes, lymphocytes, neutrophils, eosinophils, or platelet count) in CBD-treated subjects compared to placebo subjects. | | |
| Chemistry | In the controlled trial database, there were no notable changes in sodium, potassium, random glucose, total protein, albumin, prolactin, or high-density lipoproteins. | | |

[a] The frequency was 10% in this group, but the estimate is difficult to interpret because there were only 10 subjects in this dose group.
[b] These include irritability, agitation, somnolence, sedation, lethargy, disorientation, fatigue, malaise, asthenia, ataxia, tremor, aggression, anger, drooling, hypersalivation, insomnia and other sleep disturbances, falls, dizziness, balance disorders, and gait disturbances.
[c] There were 10 subjects in the 5 mg/kg/d group, 75 subjects in the 25 mg/kg/d group, 238 subjects in the 20 mg/kg/d group. In addition, there were 313 subjects who received 10 + 20 mg/kg/d and 51 (16.3%) of these subjects experienced weight decrease. Of the 227 subjects in the placebo group, 19 (8.4%) experienced weight decrease.
[d] Diarrhea was also reported at a frequency of 9% in the placebo group.
Abbreviations: AE = adverse event; AED = anti-epileptic drug; ALT = alanine transaminase; CBD = cannabidiol; CNS = central nervous system; C-SSRS = Columbia Suicide Severity Rating Scale; ECG = electrocardiogram; GI = gastrointestinal; SAE = serious adverse event.

Summary

As seen in FIG. 1, the amount of the disclosed compositions necessary to achieve the same plasma level concentration of cannabidiol as commercially available Epidiolex™ is greatly reduced. Because of this fact, not only is a lower dosage of the disclosed composition necessary to be administered to achieve therapeutic blood plasma levels relative to Epidiolex™, but such reduced dosage also incorporates a much lower amount of edible oil. Without wishing to be limited by theory, it is believed the about 9:1 ratio of sesame oil to cannabidiol in Epidiolex™ contributes to the gastrointestinal side effects widely reported by Epidiolex™ users, which are significantly lower in the case of, for instance, diarrhea incidence with the disclosed composition at a rate of 4.3% reported in its clinical testing compared to 9% reported with Epidiolex™ and Epidiolex placebo compositions, at dose levels respectively that have been shown to achieve roughly the same blood plasma CBD levels for therapeutic efficacy purposes.

The disclosed compositions are free flowing solids that can be incorporated into any acceptable form, for example, capsule, pill, lozenge, and the like. Wherein each dose of the disclosed composition delivers greater plasma level concentrations of cannabidiol without the excessive dosage of an edible oil carrier.

Other advantages which are obvious and which are inherent to the disclosure will be evident to one skilled in the art. It will be understood that certain features and sub-combinations are of utility and may be employed without reference to other features and sub-combinations. This is contemplated by and is within the scope of the claims. Since many possible embodiments can be made relating to this disclosure without departing from the scope thereof, it is to be understood that all matter herein set forth or shown in the accompanying drawings is to be interpreted as illustrative and not in a limiting sense.

What is claimed is:

1. A method for treating epilepsy in a subject, consisting of administering to the subject a composition consisting of:
   a) from about 30 mg to about 135 mg of CBD oil containing from about 88% to about 91% by weight of cannabidiol;

b) from about 60 mg to about 270 mg of sunflower oil;
c) from about 25 mg to about 65 mg of one or more bile salts wherein the salts contain from about 45% to about 55% by weight of cholic acid, deoxycholic acid, taurocholate, glycocholic acid, and mixtures thereof, and
d) from about 120 mg to about 324 mg of one or more carriers chosen from tapioca starch, colloidal silicon dioxide, and mixtures thereof.

2. The method according to claim 1, wherein the consists of:
a) about 87 mg of CBD oil containing from about 88% to about 91% by weight of cannabidiol;
b) about 174 mg of sunflower oil;
c) about 65 mg of one or more bile salts wherein the salts contain from about 45% to about 55% by weight of cholic acid, deoxycholic acid, taurocholate, glycocholic acid, and mixtures thereof; and
d) about 165 mg of tapioca starch and about 159 mg of colloidal silicon dioxide.

3. The method according to claim 1, wherein the composition consists of:
a) about 30 mg of CBD oil containing from about 88% to about 91% by weight of cannabidiol;
b) about 60 mg of sunflower oil;
c) about 25 mg of one or more bile salts wherein the salts contain from about 45% to about 55% by weight of cholic acid, deoxycholic acid, taurocholate, glycocholic acid, and mixtures thereof; and
d) about 127 mg of tapioca starch and about 122 mg of colloid silicon dioxide.

4. The method according to claim 1, wherein the composition consists of:
a) about 67 mg of CBD oil containing from about 88% to about 91% by weight of cannabidiol;
b) about 134 mg of sunflower oil;
c) about 50 mg of one or more bile salts wherein the salts contain from about 45% to about 55% by weight of cholic acid, deoxycholic acid, taurocholate, glycocholic acid, and mixtures thereof; and
d) about 127 mg of tapioca starch and about 122 mg of colloid silicon dioxide.

5. The method according to claim 1, wherein the composition consists of:
a) about 135 mg of CBD oil containing from about 88% to about 91% by weight of cannabidiol;
b) about 270 mg of sunflower oil;
c) about 100 mg of one or more bile salts wherein the salts contain from about 45% to about 55% by weight-of cholic acid, deoxycholic acid, taurocholate, glycocholic acid, and mixtures thereof; and
d) about 255 mg of tapioca starch and about 245 mg colloidal silicon dioxide.

6. The method according to claim 1, wherein the composition is administered at a dose of from about 2.5 mg/kg/day to about 4.9 mg/kg/day.

7. The method according to claim 1, wherein the composition is administered at a dose of from about 5 mg/kg/day to about 25 mg/kg/day.

8. A method for treating epilepsy in a subject, comprising administering to the subject a composition consisting of:
a) from about 30 mg to about 135 mg of CBD oil containing from about 88% to about 91% by weight-of cannabidiol;
b) from about 60 mg to about 270 mg of sunflower oil;
c) from about 25 mg to about 65 mg of one or more bile salts wherein the salts contain from about 45% to about 55% by weight of cholic acid, deoxycholic acid, taurocholate, glycocholic acid, and mixtures thereof; and
d) from about 120 mg to about 324 mg of one or more carriers chosen from tapioca starch, colloidal silicon dioxide, and mixtures thereof.

9. The method according to claim 8, wherein the composition consists of:
a) about 87 mg of CBD oil containing from about 88% to about 91% by weight of cannabidiol;
b) about 174 mg of sunflower oil;
c) about 65 mg of one or more bile salts wherein the salts contain from about 45% to about 55% by weight-of cholic acid, deoxycholic acid, taurocholate, glycocholic acid, and mixtures thereof; and
d) about 165 mg of tapioca starch and about 159 mg of colloidal silicon dioxide.

10. The method according to claim 8, wherein the composition consists of:
a) about 30 mg of CBD oil containing from about 88% to about 91% by weight of cannabidiol;
b) about 60 mg of sunflower oil;
c) about 25 mg of one or more bile salts wherein the salts contain from about 45% to about 55% by weight-of cholic acid, deoxycholic acid, taurocholate, glycocholic acid, and mixtures thereof; and
d) about 127 mg of tapioca starch and about 122 mg of colloid silicon dioxide.

11. The method according to claim 8, wherein the composition consists of:
a) about 67 mg of CBD oil containing from about 88% to about 91% by weight of cannabidiol;
b) about 134 mg of sunflower oil;
c) about 50 mg of one or more bile salts wherein the salts contain from about 45% to about 55% by weight-of cholic acid, deoxycholic acid, taurocholate, glycocholic acid, and mixtures thereof; and
d) about 127 mg of tapioca starch and about 122 mg of colloid silicon dioxide.

12. The method according to claim 8, wherein the composition consists of:
a) about 135 mg of CBD oil containing from about 88% to about 91% by weight-of cannabidiol;
b) about 270 mg of sunflower oil;
c) about 100 mg of one or more bile salts wherein the salts contain from about 45% to about 55% by weight-of cholic acid, deoxycholic acid, taurocholate, glycocholic acid, and mixtures thereof; and
d) about 255 mg of tapioca starch and about 245 mg colloidal silicon dioxide.

13. The method according to claim 12, wherein the composition is administered at a dose of from about 2.5 mg/kg/day to about 4.9 mg/kg/day.

* * * * *